United States Patent [19]

Fischer

[11] 3,933,460

[45] Jan. 20, 1976

[54] HERBICIDAL MIXTURE OF A BENZOFURANYL METHANESULFONATE AND A SUBSTITUTED PYRIDAZONE

[75] Inventor: Adolf Fischer, Mutterstadt, Germany

[73] Assignee: BASF Aktiengesellschaft, Ludwigshafen (Rhine), Germany

[22] Filed: July 1, 1974

[21] Appl. No.: 484,974

[30] Foreign Application Priority Data
July 9, 1973    Germany............................ 2334787

[52] U.S. Cl. .......................... 71/88; 71/67; 71/92; 71/103; 71/106; 71/111; 71/113; 71/115; 71/121; 71/DIG. 1
[51] Int. Cl.² ........................................... A01N 9/00
[58] Field of Search ................................... 71/88, 92

[56] References Cited
UNITED STATES PATENTS

| | | | |
|---|---|---|---|
| 3,689,507 | 9/1972 | Gates et al. .............................. | 71/92 |
| 3,787,198 | 1/1974 | Hogimato et al. ....................... | 71/93 |
| 3,846,113 | 11/1974 | Fischer .................................... | 71/92 |
| 3,849,107 | 11/1974 | Fischer .................................... | 71/93 |

OTHER PUBLICATIONS

Ebner et al., "Herbicidal 5-(alkylamino), etc.," (1970), CA 72 No, 121567k, (1970).
Badische Anilin et al., "Herbicidal Compositions" (1972), CA 78 No. 12695d, (1973).

*Primary Examiner*—Glennon H. Hollrah
*Attorney, Agent, or Firm*—Johnston, Keil Thompson & Shurtleff

[57] ABSTRACT

New and valuable herbicides containing compositions of different active ingredients.

1 Claim, No Drawings

HERBICIDAL MIXTURE OF A BENZOFURANYL METHANESULFONATE AND A SUBSTITUTED PYRIDAZONE

The present invention relates to new and valuable herbicides containing compositions of active ingredients.

It is known that benzofuranyl methane sulfonates, carbamates, halogen fatty acids, pyridazones, uracils, pyrazole acetamides, pyrazolium sulfates and phenylsulfonyl methane sulfone-o-toluidide have a herbicidal action. However, this action is not always satisfactory.

I have now found that a composition of
a. a compound of the formula

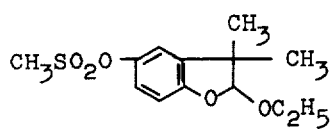

and/or
b. one or more compounds of the formula

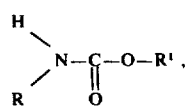

where R denotes alkyl, phenyl which may be substituted by methyl or halogen, nitrobenzenesulfonyl or aminobenzenesulfonyl, and $R^1$ denotes alkyl which may be substituted by halogen, alkenyl which may be substituted by halogen, alkynyl which may be substituted by halogen, phenyl which may be substituted by halogen or alkyl, benzyl which may be substituted by halogen or alkyl, 3-methoxycarbonylaminophenyl or the radical

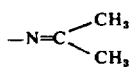

with the proviso that, in a composition of $a+b$, $b+g$ and $b+h$, $R^1$ is not 3-methoxycarbonylaminophenyl, and/or
c. one or more compounds of the formula

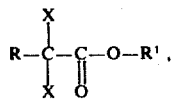

where X denotes hydrogen or halogen, R denotes alkyl, haloalkyl, benzamidooxy, or benzyl which may be substituted by halogen, methyl, methoxy or haloalkyl, and $R^1$ denotes hydrogen, alkyl which may be substituted by halogen, or benzyl which may be substituted by halogen, or a salt of such a compound, and/or
d. a compound of the formula

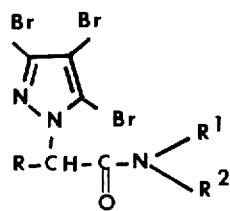

where each of R, $R^1$ and $R^2$ denotes lower alkyl, and/or
e. a compound of the formula

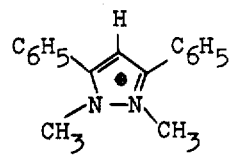 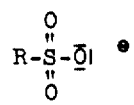

where R denotes alkoxy, or phenyl which may be substituted by halogen or alkyl, and/or
f. a compound of the formula

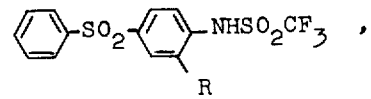

where R denotes lower alkyl, and/or
g. a compound of the formula

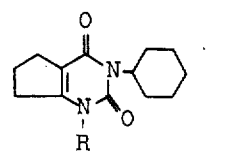

where R denotes hydrogen, α,α-dimethyl-β-acetoxypropionyl or acetyl, and/or
h. a compound of the formula

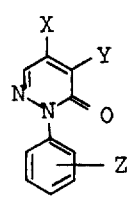

where X denotes amino, α-hydroxy-β,β,β-trichloroethylamino, acetylamino, haloacetylamino, acetoacetylamino, alkylamino, dialkylamino, alkoxyamino, alkoxyalkylamino, dimethylformamidine, an ester of adipamic acid, a dialkyl ester of aminotartronic acid, methoxy, or the radical

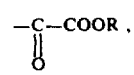

R denoting lower alkyl, phenyl or hydrogen, Y denotes chloro, bromo or methoxy, and Z denotes hydrogen, methyl, trifluoromethyl or halogen, with the proviso that, in a composition of $a+h$, X does not denote amino, α-hydroxy-β,β,β-trichloroethylamino or —NH-COOR, R denoting alkyl of a maximum of 4 carbon atoms, hydrogen, or a salt, when Z is hydrogen and Y is chloro or bromo, and with the proviso that, in a composition of $b+h$, $R^1$ does not denote 3-methoxycarbonylaminophenyl, or a salt of such a compound, e.g., sodium, dimethylamine, diethanolamine and dimethylethanolamine salt, has a better herbicidal action than the individual active ingredients.

The compositions may contain one or more compounds of the formula a and of the formulas b, c, d, e, f, g and h.

The ratio of the active ingredients to each other may be selected at will, and are for instance from 0.1 to 10:1:0.1 to 10 parts (by weight) of the various active ingredients.

The amount used of the agents according to the invention may vary and depends in essence on the type of effect to be achieved; it is generally from 0.1 to 30 (and more), preferably from 0.2 to 6, kg per hectare of active ingredient. The agents according to the invention may be used once or several times before or after planting, before sowing, pre-emergence, during emergence, and postemergence.

The compositions are selective in *Triticum spp.*, *Hordeum spp.*, *Secale spp.*, *Zea mays*, *Oryza sative*, *Gossypium hirsutum*, *Medicago sativa*, *Pisum sativum*, *Phaseolus vulgaris*, *Arachis spp.*, *Beta spp.*, *Brassica napus*, *Solanum tuberosum*, *Saccharum officinarum*, *Tilia spp.*, *Ulmus spp.*, *Pyrus spp.*, *Malus spp.*, *Allium cepa*, *Daucus carota*, *Spinachia oleracea* and other crops.

The compositions may also be used as total herbicides on ditches, aquatic areas, railroad tracks, and barren or waste land, etc.

Preferred compositions according to the invention are: $a+b+c, a+b+d, a+b+e, a+b+f, a+b+g, a+c+d, a+c+e, a+c+f, a+c+g, a+b+h, a+c+h, a+d+e, a+d+f, a+d+g, a+d+h, a+e+f, a+e+g, a+e+h, a+f+g, a+f+h, a+g+h, b+c+d, b+c+e, b+c+f, b+c+g, b+c+h, b+d+e, b+d+f, b+d+g, b+d+h, b+e+f, b+e+g, b+e+h, b+f+g, b+f+h, b+g+h, c+d+e, c+d+f, c+d+g, c+d+h, c+e+f, c+e+g, c+e+h, c+f+g, c+f+h, c+g+h, d+e+f, d+e+g, d+e+h, d+f+g, d+f+h, d+g+h, e+f+g, e+f+h, e+g+h f+g+h, a+b, a+c, a+d, a+e, a+f, h+g, a+h, b+c, b+d, b+e, b+f, b+g, b+h, c+d, c+e, c+f, c+g, c+h, d+e, d+f, d+g, d+h, e+f, e+g, e+h, f+g, f+h$.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenosulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compounds such as substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthio- or -dithiophosphates substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoidenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as

| | |
|---|---|
| Cynodon spp. | Dactylis spp. |
| Digitaria spp. | Avena spp. |
| Echinochloa spp. | Bromus spp. |
| Setaria spp. | Uniola spp. |
| Panicum spp. | Poa spp. |
| Alopecurus spp. | Leptochloa spp. |
| Lolium spp. | Brachiaria spp. |
| Sorghum spp. | Eleusine spp. |
| Agropyron spp. | Cenchrus spp. |
| Phalaris spp. | Eragrostis spp. |
| Apera spp. | Phragmitres communis |
| etc.; | |
| Cyperaceae, such as | |
| Carex spp. | Eleocharis spp. |
| Cyperus spp. | Scirpus spp. |
| etc.; | |
| dicotyledonous weeds, such as | |
| Malvaceae, e.g., | |
| Abutilon theoprasti | Hibiscus spp. |
| Sida spp. | Malva spp. |
| etc.; | |
| Compositae, such as | |
| Ambrosia spp. | Centaurea spp. |
| Lactuca spp. | Tussilago spp. |
| Senecio spp. | Lapsana communis |
| Sonchus spp. | Tagetes spp. |
| Xanthium spp. | Erigeron spp. |
| Iva spp. | Anthemis spp. |
| Galinsoga spp. | Matricaria spp. |
| Taraxacum spp. | Artemisia spp. |
| Chrysanthemum spp. | Bidens spp. |
| Cirsium spp. | etc.; |
| Convolvulaceae, such as | |
| Convolvulus spp. | Cuscuta spp. |
| Ipomoea spp. | Jaquemontia tamnifolia |
| etc.; | |
| Cruciferae, such as | |
| Barbarea vulgaris | Arabidopsis thaliana |
| Brassica spp. | Descurainia spp. |
| Capsella spp. | Draba spp. |
| Sisymbrium spp. | Coronopus didymus |
| Thlaspi spp. | Lepidium spp. |
| Sinapis arvensis | Raphanus spp. |
| etc.; | |
| Geraniaceae, such as | |
| Erodium spp. | Geranium spp. |
| etc.; | |
| Portulacaceae, such as | |
| Portulaca spp. | etc.; |
| Primulaceae, such as | |
| Anagallis arvensis | Lysimachia spp. |
| etc. | |
| Rubiaceae, such as | |
| Richardia spp. | Diodia spp. |
| Galium spp. | etc.; |
| Scrophulariaceae, such as | |
| Linaria spp. | Digitalis spp. |

-continued

| | |
|---|---|
| Veronica spp. | etc.; |
| Solanaceae, such as | |
| Physalis spp. | Nicandra spp. |
| Solanum spp. | Datura spp. |
| etc.; | |
| Urticaceae, such as | |
| Urtica spp. | |
| Violaceae, such as | |
| Viola spp. | etc.; |
| Zygophyllaceae, such as | |
| Tribulus terrestis | etc.; |
| Euphorbiaceae, such as | |
| Mercurialis annua | Euphorbia spp. |
| Umbelliferae, such as | |
| Daucus carota | Ammi majus |
| Aethusa cynapium | etc.; |
| Commelinaeae, such as | |
| Commelina spp. | etc.; |
| Labiatae, such as | |
| Lamium spp. | Galeopsis spp. |
| etc.; | |
| Leguminosae, such as | |
| Medicago spp. | Sesbania exaltata |
| Trifolium spp. | Cassia spp. |
| Vicia spp. | Lathyrus spp. |
| etc.; | |
| Plantaginaceae, such as | |
| Plantago spp. | etc.; |
| Polygonaceae, such as | |
| Polygonum spp. | Fagopyrum spp. |
| Rumex spp. | etc.; |
| Aizoaceae, such as | |
| Mollugo verticillata | etc.; |
| Amaranthaceae, such as | |
| Amaranthus spp. | etc.; |
| Boraginaceae, such as | |
| Amsinckia spp. | Anchusa spp. |
| Myostis spp. | Lithospermum spp. |
| etc.; | |
| Caryophyllaceae, such as | |
| Stellaria spp. | Silene spp. |
| Spergula spp. | Cerastium spp. |
| Saponaria spp. | Agrostemma githago |
| Scleranthus annuus | etc.; |
| Chenopodiaceae, such as | |
| Chenopodium spp. | Atriplex spp. |
| Kochia spp. | Monolepsis nuttalliana |
| Salsola Kali | etc.; |
| Lythraceae, such as | |
| Cuphea spp. | etc.; |
| Oxalidaceae, such as | |
| Oxalis spp. | |
| Ranunculaceae, such as | |
| Ranunculus spp. | Adonis spp. |
| Delphinium spp. | etc.; |
| Papaveraceae, such as | |
| Papaver spp. | Fumaria officinalis |
| etc.; | |
| Onagraceae, such as | |
| Jussiaea spp. | etc.; |
| Rosaceae, such as | |
| Alchemillia spp. | Potentilla spp. |
| etc.; | |
| Potamogetonaceae, such as | |
| Potamogeton spp. | etc.; |
| Najadaceae, such as | |
| Najas spp. | etc.; |
| Equisetaceae | |
| Equisetum spp. | etc.; |
| Marsileaceae, such as | |
| Marsilea quadrifolia | etc.; |
| Polypodiaceae, | |
| Pteridium quilinum | |
| Alismataceae | |
| Alisma spp. | Sagittaria sagittifolia |
| etc. | |

In the greenhouse and in the open, compositions of the following compounds were tested on the above-mentioned plants:
2-ethoxy-2,3-dihydro-3,3-dimethyl-5-benzofuranylmethanesulfonate
3,4-dichlorobenzyl N-methylcarbamate
isopropyl N-phenylcarbamate
methyl N-(4-nitrobenzenesulfonyl)-carbamate
methyl N-(4-aminobenzenesulfonyl)-carbamate
methyl N-3,4-dichlorophenylcarbamate
N-3-chlorophenylcarbamate
4-chlorobutyn-2-yl-1-N-3-chlorophenylcarbamate
butyn-1-yl-3N-3-chlorophenylcarbamate
3-methoxycarbonylaminophenyl-N-(3'-methylphenyl)-carbamate
O-(N-phenyl-carbamoyl)-propanonoxime
trichloroacetic acid, sodium salt
$\alpha,\alpha$-dichloropropionic acid, sodium salt
$\alpha,\alpha,\beta$-trichloropropionic acid, sodium salt
benzyl-$\alpha,\alpha$-dichloropropionate
$\alpha,\alpha,\beta,\beta$-tetrafluoropropionic acid, sodium salt
$\alpha,\alpha$-dichlorobutyric acid, sodium salt
methyl $\alpha$-chloro-$\beta$-(4-chlorophenyl)-propionate
benzamidooxyacetic acid
3-cyclohexyl-5,6-trimethylene uracil
1-$\alpha,\alpha$-dimethyl-$\beta$-acetoxypropionyl-3-cyclohexyl-5,6-trimethylene uracil
3,4,5-tribromo-N,N-$\alpha$-trimethylpyrazole-1-acetamide
3,4,5-tribromo-N,N-dimethyl-$\alpha$-ethylpyrazole acetamide
3,4,5-tribromo-N,N-$\alpha$-triethylpyrazole acetamide
3,4,5-tribromo-N,N-diethyl-$\alpha$-methylpyrazole acetamide
1,1,1-trifluoro-4'-(phenylsulfonyl)-methanesulfone-o-toluidide
1-phenyl-4-amino-5-chloropyridazone-(6)
1-phenyl-4-amino-5-bromopyridazone-(6)
1-phenyl-4-amino-5-methoxypyridazone-(6)
1-m-trifluoromethylphenyl-4-amino-5-chloropyridazone-(6)
1-m-trifluoromethylphenyl-4-amino-5-bromopyridazone-(6)
1-m-methylphenyl-4-amino-5-bromopyridazone-(6)
1-m-methylphenyl-4-amino-5-chloropyridazone-(6)
1-phenyl-4-($\alpha$-hydroxy-$\beta,\beta,\beta$-trichloroethyl)-amino-5-bromopyridazone-(6)
1-m-trifluoromethylphenyl-4-($\alpha$-hydroxy-$\beta,\beta,\beta$-trichloroethyl)-amino-5-chloropyridazone-(6)
1-m-trifluoromethylphenyl-4-($\alpha$-hydroxy-$\beta,\beta,\beta$-trichloroethyl)-amino-5-bromopyridazone-(6)
1-phenyl-4-acetylamino-5-chloropyridazone-(6)
1-phenyl-4-acetylamino-5-bromopyridazone-(6)
1-m-trifluoromethylphenyl-4-acetylamino-5-bromopyridazone-(6)
1-m-trifluoromethylphenyl-4-acetylamino-5-chloropyridazone-(6)
1-m-trifluoromethylphenyl-4-chloroacetylamino-5-chloropyridazone-(6)
1-phenyl-4-bromoacetylamino-5-bromopyridazone-(6)
1-phenyl-4-acetoacetylamino-5-bromopyridazone-(6)
1-m-trifluoromethylphenyl-4-chloroacetylamino-5-bromopyridazone-(6)
1-m-trifluoromethylphenyl-4-diethylamino-5-chloropyridazone-(6)
tert-butyl-N-[m-methylphenyl-5-bromopyridazone-(6)-yl-(4)]-oxamate
1-phenyl-4-methoxy-5-chloropyridazone-(6)
methyl N-[(1-phenyl-5-bromopyridazone-(6)-yl-(4)]-oxamate
phenyl N-[(1-phenyl-5-bromopyridazone-(6)-yl-(4)]-oxamate
ethyl N-[(1-m-trifluoromethylphenyl-5-bromopyridazone-(6)-yl-(4)]-oxamate
N-[(1-m-trifluoromethylphenyl-5-bromopyridazone-(6)-yl-(4)]-oxamic acid N-[(1-m-trifluoromethylphenyl-5-chloropyridazone-(6)-yl-(4)]-oxamic acid
tert-butyl N-[(1-m-trifluoromethylphenyl-5-bromopyridazone-(6)-yl-(4)]-oxamate
N-[(1-m-trifluoromethylphenyl-5-bromopyridazone-(6)-yl-(4)]-oxamic acid
N-[(1-m-trifluoromethylphenyl)-4-dichloroacetylamino-5-bromopyridazone-(6)]
N-[(1-phenyl-5-bromopyridazone-(6)-yl-(4)]-oxamic acid, sodium salt
N-[(1-phenyl-5-bromopyridazone-(6)-yl-(4)]-oxamic acid, dimethylethanolamine salt
isopropyl N-[(1-phenyl-5-bromopyridazone-(6)-yl-(4)]-oxamate
1-phenyl-4-dichloroacetylamino-5-bromopyridazone-(6)
N-[(1-phenyl-5-bromopyridazone-(6)-yl-(4)]-adipamic acid, methylester
N-[(1-m-trifluoromethylphenyl-5-bromopyridazone-(6)-yl-(4)]-dimethylformamidine
1-m-trifluoromethylphenyl-4-methylamino-5-chloropyridazone-(6)
1-m-trifluoromethylphenyl-4-methylamino-5-bromopyridazone-(6)
1-m-trifluoromethylphenyl-4-dimethylamino-5-chloropyridazone-(6)
1-m-trifluoromethylphenyl-4-dimethylamino-5-bromopyridazone-(6)
diethyl N-[4-(1-phenyl-5-bromopyridazone)-yl]-aminotartrate
1-m-trifluoromethylphenyl-4-methoxy-5-chloropyridazone-(6)
1-m-trifluoromethylphenyl-4-methoxy-5-bromopyridazone-(6)
1-m-trifluoromethylphenyl-4,5-dimethoxypyridazone-(6)
1-m-methylphenyl-4-methoxy-5-bromopyridazone-(6)
1-m-methylphenyl-4-methoxy-5-chloropyridazone-(6)
1-m-methylphenyl-4-methoxy-5-methoxypyridazone-(6)
1-phenyl-4,5-dimethoxypyridazone-(6)
1-phenyl-4-methoxy-5-bromopyridazone-(6)
1-m-trifluoromethylphenyl-4-methoxyamino-5-chloropyridazone-(6)
1-m-trifluoromethylphenyl-4-methylmethoxyamino-5-chloropyridazone-(6)
β-chloroethyl 2,2-dichloropropionate
1,2-dimethyl-3,5-diphenylpyrazolium methyl sulfate
1,2-dimethyl-3,5-diphenylpyrazolium tolyl sulfonate
1-phenyl-4-chloroacetyl-5-bromopyridazone-(6).

The application rates in the abovementioned tests were from 0.1 to 5 and more kg per hectare. The action of compositions of the above agents corresponds to that of the compositions in Examples 1 to 34.

EXAMPLE 1

An agricultural plot was sown with various seeds. The soil prepared in this manner was then immediately treated with the following individual active ingredients and compositions thereof in granular form, the granules being incorporated into the soil:

I. 2-ethoxy-2,3-dihydro-3,3-dimethyl-5-benzofuranyl methane sulfonate, 0.15, 1.5 and 1.8 kg/ha;
II. isopropyl N-phenylcarbamate, 0.15, 1.5 and 1.8 kg/ha;
III. isopropyl N-3-chlorophenylcarbamate, 0.15, 1.5 and 1.8 kg/ha;
IV. butyn-1-yl-3 N-3-chlorophenylcarbamate, 0.15, 1.5 and 1.8 kg/ha;
V. O-(N-phenylcarbamoyl)-propanonoxime, 0.15, 1.5 and 1.8 kg/ha;
XII. 1-phenyl-4-amino-5-chloropyridazone-(6), 0.15, 1.5 and 1.8 kg/ha;
I + II + XII: 0.15+0.15+1.5, 0.15+1.5+0.15 and 1.5+0.15+0.15 kg/ha;
I + III + XII: 0.15+0.15+1.5, 0.15+1.5+0.15 and 1.5+0.15+0.15 kg/ha;
I + IV + XII: 0.15+0.15+1.5, 0.15+1.5+0.15 and 1.5+0.15+0.15 kg/ha;
I + V + XII: 0.15+0.15+1.5, 0.15+1.5+0.15 and 1.5+0.15+0.15 kg/ha.

After 3 to 4 weeks it was ascertained that the compositions had a better herbicidal action than their components, combined with the same good crop plant compatibility.

The results are given below:

| Active ingredient kg/ha | I | | | II | | | III | | |
|---|---|---|---|---|---|---|---|---|---|
| | 0.15 | 1.5 | 1.8 | 0.15 | 1.5 | 1.8 | 0.15 | 1.5 | 1.8 |
| Crop plants: | | | | | | | | | |
| Beta vulgaris | 0 | 5 | 7 | 0 | 0 | 0 | 0 | 0 | 0 |
| Allium cepa | 0 | 0 | 0 | 0 | 0 | 0 | 0 | 0 | 0 |
| Unwanted plants: | | | | | | | | | |
| Avena fatua | 5 | 60 | 70 | 5 | 42 | 49 | 4 | 41 | 48 |
| Echinochloa crus-galli | 10 | 70 | 80 | 0 | 30 | 37 | 0 | 20 | 26 |
| Matricaria chamomilla | 0 | 30 | 38 | 7 | 63 | 75 | 6 | 61 | 73 |
| Active Ingredient | IV | | | V | | | XII | | |
| Beta vulgaris | 0 | 0 | 0 | 0 | 0 | 0 | 0 | 0 | 0 |
| Allium cepa | 0 | 0 | 0 | 0 | 0 | 0 | 0 | 0 | 0 |
| Avena fatua | 3 | 40 | 46 | 3 | 41 | 56 | 0 | 15 | 19 |
| Echinochloa crus-galli | 0 | 18 | 25 | 0 | 25 | 30 | 2 | 20 | 26 |
| Matricaria chamomilla | 4 | 59 | 69 | 5 | 60 | 64 | 7 | 60 | 77 |

0 = no damage
100 = complete destruction

| Active ingredient kg/ha | I + II + XII | | | I + III + XII | | |
|---|---|---|---|---|---|---|
| | 0.15+<br>0.15+<br>1.5 | 0.15+<br>1.5+<br>0.15 | 1.5+<br>0.15+<br>0.15 | 0.15+<br>0.15+<br>1.5 | 0.15+<br>1.5+<br>0.15 | 1.5+<br>0.15+<br>0.15 |
| Crop plants: | | | | | | |
| *Beta vulgaris* | 0 | 0 | 5 | 0 | 0 | 5 |
| *Allium cepa* | 0 | 0 | 0 | 0 | 0 | 0 |
| Unwanted plants: | | | | | | |
| *Avena fatua* | 68 | 83 | 98 | 60 | 82 | 96 |
| *Echinochloa crus-galli* | 70 | 79 | 100 | 67 | 70 | 100 |
| *Matricaria chamomilla* | 98 | 100 | 80 | 100 | 100 | 81 |

| Active ingredient | I + IV + XII | | | I + V + XII | | |
|---|---|---|---|---|---|---|
| Beta vulgaris | 0 | 0 | 5 | 0 | 0 | 5 |
| Allium cepa | 0 | 0 | 0 | 0 | 0 | 0 |
| Avena fatua | 61 | 81 | 95 | 60 | 83 | 93 |
| Echinochloa crus-galli | 67 | 70 | 100 | 69 | 75 | 100 |
| Matricaria chamomilla | 97 | 100 | 86 | 98 | 100 | 79 |

0 = no damage
100 = complete destruction

EXAMPLE 2

In the greenhouse, loamy sandy soil was filled into pots and sown with the seeds of various plants. The soil prepared in this manner was subsequently treated with the following amounts of the following individual active ingredients and compositions thereof as dispersions:

II. isopropyl N-phenylcarbamate, 0.5, 1, 1.5 and 2 kg/ha;
IV. butyn-1-yl-3 N-3-chlorophenylcarbamate, 0.5, 1, 1.5 and 2 kg/ha;
V. O-(N-phenylcarbamoyl)-propanonoxime, 0.5, 1, 1.5 and 2 kg/ha;
VI. α,α-dichloropropionic acid, sodium salt, 0.5, 1, 1.5 and 2 kg/ha;
VII. trichloroacetic acid, sodium salt, 0.5, 1, 1.5 and 2 kg/ha;
II + VI: 0.5+1.5, 1.5+0.5 and 1+1 kg/ha;
IV + VI: 0.5+1.5, 1.5+0.5 and 1+1 kg/ha;
V + VI: 0.5+1.5, 1.5+0.5 and 1+1 kg/ha;
II + VII: 0.5+1.5, 1.5+0.5 and 1+1 kg/ha.

After 3 to 4 weeks it was ascertained that the compositions had a better herbicidal action than their components, combined with the same good crop plant compatibility.

The results are given below:

| Active ingredient kg/ha | II | | | | IV | | | | V | | | |
|---|---|---|---|---|---|---|---|---|---|---|---|---|
| | 0.5 | 1 | 1.5 | 2 | 0.5 | 1 | 1.5 | 2 | 0.5 | 1 | 1.5 | 2 |
| Crop plant: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 12 | 30 | 42 | 53 | 15 | 30 | 40 | 50 | 15 | 27 | 41 | 56 |
| *Echinochloa crus-galli* | 11 | 18 | 30 | 40 | 6 | 12 | 18 | 30 | 10 | 12 | 25 | 30 |
| *Matricaria chamomilla* | 18 | 40 | 63 | 78 | 20 | 45 | 59 | 70 | 18 | 35 | 59 | 76 |

| Active ingredient kg/ha | VI | | | | VII | | | |
|---|---|---|---|---|---|---|---|---|
| | 0.5 | 1 | 1.5 | 2 | 0.5 | 1 | 1.5 | 2 |
| Beta vulgaris | 0 | 0 | 0 | 0 | 0 | 0 | 0 | 0 |
| Avena fatua | 15 | 27 | 60 | 76 | 10 | 24 | 45 | 56 |
| Echinochloa crus-galli | 10 | 23 | 35 | 44 | 10 | 17 | 30 | 40 |
| Matricaria chamomilla | 0 | 0 | 3 | 5 | 0 | 0 | 2 | 7 |

0 = no damage
100 = complete destruction

| Active ingredient kg/ha | II + VI | | | IV + VI | | | V + VI | | |
|---|---|---|---|---|---|---|---|---|---|
| | 0.5+<br>1.5 | 1.5+<br>0.5 | 1+1 | 0.5+<br>1.5 | 1.5+<br>0.5 | 1+1 | 0.5+<br>1.5 | 1.5+<br>0.5 | 1+1 |
| Crop plant: | | | | | | | | | |
| *Beta vulgaris* | 0 | 0 | 0 | 0 | 0 | 0 | 0 | 0 | 0 |
| Unwanted plants: | | | | | | | | | |
| *Avena fatua* | 100 | 90 | 90 | 100 | 92 | 90 | 100 | 90 | 92 |
| *Echinochloa crus-galli* | 83 | 78 | 80 | 79 | 65 | 73 | 82 | 72 | 83 |
| *Matricaria chamomilla* | 60 | 94 | 77 | 61 | 93 | 82 | 45 | 93 | 73 |

| Active ingredient kg/ha | II + VII | | |
|---|---|---|---|
| | 0.5+<br>1.5 | 1.5+<br>0.5 | 1+1 |
| Beta vulgaris | 0 | 0 | 0 |
| Avena fatua | 90 | 89 | 91 |
| Echinochloa crus-galli | 79 | 74 | 73 |

| Active ingredient kg/ha | II + VI 0.5+1.5 | II + VI 1.5+0.5 | II + VI 1+1 | IV + VI 0.5+1.5 | IV + VI 1.5+0.5 | IV + VI 1+1 | V + VI 0.5+1.5 | V + VI 1.5+0.5 | V + VI 1+1 |
|---|---|---|---|---|---|---|---|---|---|
| *Matricaria chamomilla* | 60 | 96 | 78 | | | | | | |

0 = no damage
100 = complete destruction

EXAMPLE 3

In the greenhouse, loamy sandy soil was filled into pots and sown with the seeds of various plants. The soil prepared in this manner was subsequently treated with the following amounts of the following individual active ingredients and compositions thereof as emulsions:

I. 2-ethoxy-2,3-dihydro-3,3-dimethyl-5-benzofuranyl methanesulfate, 0.25, 0.5, 0.75 and 1 kg/ha;
IX. 1,1,1-trifluoro-4'-(phenylsulfonyl)-methanesulfone-o-toluidide, 0.25, 0.5, 0.75 and 1 kg/ha;
X. 3,4,5-tribromo-N,N,α-trimethylpyrazole-1-acetamide, 0.25, 0.5, 0.75 and 1 kg/ha;
I + IX: 0.25+0.75, 0.75+0.25 and 0.25+0.25 kg/ha;
I + X: 0.25+0.75, 0.75+0.25 and 0.25+0.25 kg/ha;
IX + X: 0.25+0.75, 0.75+0.25 and 0.25+0.25 kg/ha;
I + IX + X: 0.25+0.25+0.5, 0.25+0.5+0.25 and 0.5+0.25+0.25 kg/ha.

After 3 to 4 weeks it was ascertained that the compositions had a better herbicidal action than their components, combined with the same good crop plant compatibility.

The results are given below:

the following amounts of the following individual active ingredients and compositions thereof as dispersions:

I. 2-ethoxy-2,3-dihydro-3,3-dimethyl-5-benzofuranyl methane sulfonate, 0.15, 1.5 and 1.8 kg/ha;
II. isopropyl N-phenylcarbamate, 0.15, 1.5 and 1.8 kg/ha;
III. isopropyl N-3-chlorophenylcarbamate, 0.15, 1.5 and 1.8 kg/ha;
IV. butyn-1-yl-3 N-3-chlorophenylcarbmate, 0.15, 1.5 and 1.8 kg/ha;
V. O-(N-phenylcarbamoyl)-propanonoxime, 0.15, 1.5 and 1.8 kg/ha;
VI. α,α-dichloropropionic acid, sodium salt, 0.15, 1.5 and 1.8 kg/ha;
VII. trichloroacetic acid, sodium salt, 0.15, 1.5 and 1.8 kg/ha;
VIII. α,α,β,β-tetrafluoropropionic acid, sodium salt, 0.15, 1.5 and 1.8 kg/ha;
I + II + VI: 0.15+0.15+1.5, 0.15+1.5+0.15 and 1.5+0.15+0.15 kg/ha;
I + II + VII: 0.15+0.15+1.5, 0.15+1.5+0.15 and 1.5+0.15+0.15 kg/ha;
I + III + VI: 0.15+0.15+1.5, 0.15+1.5+0.15 and 1.5+0.15+0.15 kg/ha;

| Active ingredient kg/ha | I 0.25 | I 0.5 | I 0.75 | I 1 | IX 0.25 | IX 0.5 | IX 0.75 | IX 1 | X 0.25 | X 0.5 | X 0.75 | X 1 |
|---|---|---|---|---|---|---|---|---|---|---|---|---|
| Crop plants: | | | | | | | | | | | | |
| *Brassica napus* | 0 | 0 | 0 | 0 | 0 | 0 | 0 | 0 | 0 | 0 | 0 | 0 |
| *Soja max.* | 0 | 0 | 0 | 0 | 0 | 0 | 0 | 0 | 0 | 0 | 0 | 0 |
| *Gossypium hirsutum* | 0 | 0 | 0 | 0 | 0 | 0 | 0 | 0 | 0 | 0 | 0 | 0 |
| *Arachis hypogaea* | 0 | 0 | 0 | 0 | 0 | 0 | 0 | 0 | 0 | 0 | 0 | 0 |
| Unwanted plants: | | | | | | | | | | | | |
| *Avena fatua* | 10 | 16 | 30 | 40 | 0 | 10 | 15 | 25 | 20 | 30 | 56 | 67 |
| *Lolium multiflorum* | 0 | 4 | 10 | 14 | 8 | 30 | 70 | 75 | 17 | 31 | 90 | 95 |
| *Echinochloa crus-galli* | 15 | 30 | 40 | 50 | 17 | 40 | 80 | 90 | 15 | 25 | 40 | 56 |
| Active ingredient kg/ha | I + IX 0.25+0.75 | I + IX 0.75+0.25 | I + IX 0.25+0.25 | 0.25+0.75 | I + X 0.75+0.25 | I + X 0.25+0.25 | 0.25+0.75 | IX + X 0.75+0.25 | IX + X 0.25+0.25 | | | |
| *Brassica napus* | 0 | 0 | 0 | 0 | 0 | 0 | 0 | 0 | 0 | | | |
| *Soja max.* | 0 | 0 | 0 | 0 | 0 | 0 | 0 | 0 | 0 | | | |
| *Gossypium hirsutum* | 0 | 0 | 0 | 0 | 0 | 0 | 0 | 0 | 0 | | | |
| *Arachis hypogaea* | 0 | 0 | 0 | 0 | 0 | 0 | 0 | 0 | 0 | | | |
| *Avena fatua* | 65 | 68 | 50 | 100 | 83 | 67 | 100 | 72 | 58 | | | |
| *Lolium multiflorum* | 100 | 56 | 48 | 100 | 65 | 55 | 100 | 100 | 63 | | | |
| *Echinochloa crus-galli* | 100 | 93 | 70 | 92 | 94 | 69 | 93 | 100 | 70 | | | |
| Active ingredient kg/ha | I + IX + X 0.25+0.25+0.5 | I + IX + X 0.25+0.5+0.25 | I + IX + X 0.5+0.25+0.25 | | | | | | | | | |
| Crop plants: | | | | | | | | | | | | |
| *Brassica napus* | 0 | 0 | 0 | | | | | | | | | |
| *Soja max.* | 0 | 0 | 0 | | | | | | | | | |
| *Gossypium hirsutum* | 0 | 0 | 0 | | | | | | | | | |
| *Arachis hypogaea* | 0 | 0 | 0 | | | | | | | | | |
| Unwanted plants: | | | | | | | | | | | | |
| *Avena fatua* | 93 | 78 | 75 | | | | | | | | | |
| *Lolium multiflorum* | 77 | 84 | 65 | | | | | | | | | |
| *Echinochloa crus-galli* | 90 | 100 | 89 | | | | | | | | | |

0 = no damage
100 = complete destruction

EXAMPLE 4

In the greenhouse, loamy sandy soil was filled into pots and sown with the seeds of various plants. The soil prepared in this manner was subsequently treated with I + IV + VI: 0.15+0.15+1.5, 0.15+1.5+0.15 and 1.5+0.15+0.15 kg/ha;
I + IV + VII: 0.15+0.15+1.5, 0.15+1.5+0.15 and 1.5+0.15+0.15 kg/ha;
I + V + VI: 0.15+0.15+1.5, 0.15+1.5+0.15 and 1.5+0.15+0.15 kg/ha;

I + V + VII: 0.15+0.15+1.5, 0.15+1.5+0.15 and 1.5+0.15+0.15 kg/ha;
I + II + VII: 0.15+0.15+1.5, 0.15+1.5+0.15 and 1.5+0.15+0.15 kg/ha.

After 3 to 4 weeks it was ascertained that the compositions had a better herbicidal action than their components, combined with the same good crop plant compatibility. The results are given below:

IV. butyn-1-yl-3- N-3-chlorophenylcarbamate, 1, 2 and 4 kg/ha;
V. O-(N-phenylcarbamoyl)-propanonoxime, 1, 2 and 4 kg/ha;
XII. 1-phenyl-4-amino-5-chloropyridazone-(6), 1, 2 and 4 kg/ha;
I + II + XII: 1+1+2, 1+2+1 and 2+1+1 kg/ha;
I + III + XII: 1+1+2, 1+2+1 and 2+1+1 kg/ha;

| Active ingredient kg/ha | I | | | II | | | III | | | IV | | |
|---|---|---|---|---|---|---|---|---|---|---|---|---|
| | 0.5 | 1.5 | 1.8 | 0.5 | 1.5 | 1.8 | 0.5 | 1.5 | 1.8 | 0.5 | 1.5 | 1.8 |
| Crop plants: | | | | | | | | | | | | |
| Beta vulgaris | 0 | 5 | 7 | 0 | 0 | 0 | 0 | 0 | 0 | 0 | 0 | 0 |
| Brassica napus | 0 | 0 | 0 | 0 | 0 | 0 | 0 | 0 | 0 | 0 | 0 | 0 |
| Unwanted plants: | | | | | | | | | | | | |
| Avena fatua | 5 | 60 | 70 | 5 | 42 | 49 | 4 | 41 | 48 | 3 | 40 | 46 |
| Echinochloa crus-galli | 10 | 70 | 80 | 0 | 30 | 37 | 0 | 20 | 26 | 0 | 18 | 25 |
| Lolium multiflorum | 0 | 20 | 27 | 15 | 60 | 76 | 10 | 43 | 54 | 13 | 50 | 63 |

| Active ingredient kg/ha | V | | | VI | | | VII | | | VIII | | |
|---|---|---|---|---|---|---|---|---|---|---|---|---|
| | 0.5 | 1.5 | 1.8 | 0.5 | 1.5 | 1.8 | 0.5 | 1.5 | 1.8 | 0.5 | 1.5 | 1.8 |
| Beta vulgaris | 0 | 0 | 0 | 0 | 0 | 0 | 0 | 0 | 0 | 0 | 0 | 0 |
| Brassica napus | 0 | 0 | 0 | 0 | 0 | 0 | 0 | 0 | 0 | 0 | 0 | 0 |
| Avena fatua | 3 | 41 | 56 | 7 | 60 | 70 | 5 | 45 | 50 | 5 | 50 | 60 |
| Echinochloa crus-galli | 0 | 25 | 30 | 3 | 35 | 40 | 3 | 30 | 40 | 5 | 48 | 56 |
| Lolium multiflorum | 16 | 63 | 67 | 5 | 35 | 42 | 3 | 24 | 30 | 8 | 52 | 60 |

0 = no damage
100 = complete destruction

| Active ingredient kg/ha | I + II + VI | | | I + II + VII | | | I + III + VI | | |
|---|---|---|---|---|---|---|---|---|---|
| | 0.15+0.15+1.5 | 0.15+1.5+0.15 | 1.5+0.15+0.15 | 0.15+0.15+1.5 | 0.15+1.5+0.15 | 1.5+0.15+0.15 | 0.15+0.15+1.5 | 0.15+1.5+0.15 | 1.5+0.15+0.15 |
| Crop plants: | | | | | | | | | |
| Beta vulgaris | 0 | 0 | 5 | 0 | 0 | 5 | 0 | 0 | 5 |
| Brassica napus | 0 | 0 | 0 | 0 | 0 | 0 | 0 | 0 | 0 |
| Unwanted plants: | | | | | | | | | |
| Avena fatua | 100 | 90 | 100 | 88 | 92 | 100 | 100 | 85 | 100 |
| Echinochloa crus-galli | 85 | 80 | 100 | 82 | 80 | 100 | 86 | 70 | 100 |
| Lolium multiflorum | 87 | 97 | 77 | 85 | 97 | 100 | 82 | 84 | 70 |
| Active ingredient | I + IV + VI | | | I + IV + VII | | | I + V + VI | | |
| Beta vulgaris | 0 | 0 | 5 | 0 | 0 | 5 | 0 | 0 | 5 |
| Brassica napus | 0 | 0 | 0 | 0 | 0 | 0 | 0 | 0 | 0 |
| Avena fatua | 98 | 90 | 100 | 89 | 88 | 100 | 100 | 89 | 100 |
| Echinochloa crus-galli | 87 | 70 | 100 | 82 | 68 | 100 | 87 | 75 | 100 |
| Lolium multiflorum | 83 | 92 | 73 | 76 | 90 | 70 | 89 | 100 | 77 |
| Active ingredient | I + V + VII | | | I + II + VIII | | | | | |
| Beta vulgaris | 0 | 0 | 5 | 0 | 0 | 5 | | | |
| Brassica napus | 0 | 0 | 0 | 0 | 0 | 0 | | | |
| Avena fatua | 100 | 90 | 100 | 93 | 88 | 100 | | | |
| Echinochloa crus-galli | 78 | 75 | 100 | 97 | 100 | 100 | | | |
| Lolium multiflorum | 88 | 100 | 76 | 99 | 100 | 100 | | | |

0 = no damage
100 = complete destruction

EXAMPLE 5

An agricultural plot was sown with the seeds of various plants. The soil prepared in this manner was then treated with the following amounts of the following individual active ingredients and compositions thereof as dusts:

I. 2-ethoxy-2,3-dihydro-3,3-dimethyl-5-benzofuranyl methane sulfonate, 1, 2 and 4 kg/ha;
II. isopropyl N-phenylcarbamate, 1, 2 and 4 kg/ha;
III. isopropyl N-3-chlorophenylcarbamate, 1, 2 and 4 kg/ha;

I + IV + XII: 1+1+2, 1+2+1 and 2+1+1 kg/ha;
I + V + XII: 1+1+2, 1+2+1 and 2+1+1 hg/ha;
and, for comparison,
XI N-p-chlorophenyl-N',N'-dimethylurea, 1, 2 and 4 kg/ha;
I + XI + XII: 1+2+1 kg/ha;
I + XI + II: 1+2+1 kg/ha.

After 3 to 4 weeks it was ascertained that the compositions had the same herbicidal action as their components and the compositions I+XI+XII and I+XI+II, combined with superior crop plant compatibility.
The results are given below:

| Active ingredient kg/ha | I | | | II | | | III | | |
|---|---|---|---|---|---|---|---|---|---|
| | 1 | 2 | 4 | 1 | 2 | 4 | 1 | 2 | 4 |
| Crop plants: | | | | | | | | | |

-continued

| Active ingredient | I | | | II | | | III | | |
|---|---|---|---|---|---|---|---|---|---|
| kg/ha | 1 | 2 | 4 | 1 | 2 | 4 | 1 | 2 | 4 |
| Beta vulgaris | 4 | 10 | 30 | 0 | 0 | 10 | 0 | 0 | 10 |
| Allium cepa | 0 | 0 | 5 | 0 | 0 | 0 | 0 | 0 | 0 |
| Unwanted plants: | | | | | | | | | |
| Avena fatua | 40 | 80 | 100 | 30 | 53 | 100 | 33 | 54 | 95 |
| Echinochloa crus-galli | 50 | 85 | 100 | 18 | 40 | 70 | 10 | 30 | 67 |
| Matricaria chamomilla | 22 | 40 | 70 | 40 | 78 | 100 | 38 | 80 | 100 |

| Active ingredient | IV | | | V | | | XI | | | XII | | |
|---|---|---|---|---|---|---|---|---|---|---|---|---|
| kg/ha | 1 | 2 | 4 | 1 | 2 | 4 | 1 | 2 | 4 | 1 | 2 | 4 |
| Beta vulgaris | 0 | 0 | 5 | 0 | 0 | 10 | 25 | 100 | 100 | 0 | 0 | 10 |
| Allium cepa | 0 | 0 | 0 | 0 | 0 | 0 | 70 | 100 | 100 | 0 | 0 | 5 |
| Avena fatua | 30 | 50 | 100 | 29 | 56 | 100 | 70 | 100 | 100 | 12 | 20 | 75 |
| Echinochloa crus-galli | 12 | 30 | 70 | 12 | 30 | 68 | 95 | 100 | 100 | 13 | 32 | 75 |
| Matricaria chamomilla | 45 | 70 | 100 | 35 | 76 | 100 | 100 | 100 | 100 | 50 | 85 | 100 |

0 = no damage
100 = complete destruction

| Active ingredient | I + II + XII | | | I + III + XII | | | I + IV + XII | | |
|---|---|---|---|---|---|---|---|---|---|
| kg/ha | 1+1+2 | 1+2+1 | 2+1+1 | 1+1+2 | 1+2+1 | 2+1+1 | 1+1+2 | 1+2+1 | 2+1+1 |
| Crop plants: | | | | | | | | | |
| Beta vulgaris | 4 | 4 | 10 | 4 | 4 | 10 | 4 | 4 | 10 |
| Allium cepa | 0 | 0 | 0 | 0 | 0 | 0 | 0 | 0 | 0 |
| Unwanted plants: | | | | | | | | | |
| Avena fatua | 100 | 100 | 100 | 100 | 100 | 100 | 100 | 100 | 100 |
| Echinochloa crus-galli | 100 | 100 | 100 | 100 | 100 | 100 | 100 | 100 | 100 |
| Matricaria chamomilla | 100 | 100 | 100 | 100 | 100 | 100 | 100 | 100 | 100 |

| Active ingredient | I + V + XII | | | I + XI + XII | I + XI + II |
|---|---|---|---|---|---|
| kg/ha | 1+1+2 | 1+2+1 | 2+1+1 | 1+2+1 | 1+2+1 |
| Beta vulgaris | 4 | 4 | 10 | 100 | 100 |
| Allium cepa | 0 | 0 | 0 | 100 | 100 |
| Avena fatua | 100 | 100 | 100 | 100 | 100 |
| Echinochloa crus-galli | 100 | 100 | 100 | 100 | 100 |
| Matricaria chamomilla | 100 | 100 | 100 | 100 | 100 |

0 = no damage
100 = complete destruction

EXAMPLE 6

An agricultural plot was sown with various seeds. The soil prepared in this manner was then immediately treated with the following amounts of the following individual active ingredients and compositions thereof as oil dispersions:

I. 2-ethoxy-2,3-dihydro-3,3-dimethyl-5-benzofuranyl methane sulfonate, 0.25, 1, 1.5, 2 and 4 kg/ha;
VI. α,α-dichloropropionic acid, sodium salt, 0.25, 1, 1.5, 2 and 4 kg/ha;
VII. trichloroacetic acid, sodium salt, 0.25, 1, 1.5, 2 and 4 kg/ha;
VIII. α,α,β,β-tetrafluoropropionic acid, sodium salt, 0.25, 1, 1.5, 2 and 4 kg/ha;
XII. 1-phenyl-4-amino-5-chloropyridazone-(6), 0.25, 1, 1.5, 2 and 4 kg/ha;
I + VI + XII: 0.25+0.25+1, 0.25+1+0.25, 1+0.25+0.25, 1+1+2, 1+2+1 and 2+1+1 kg/ha;
I + VII + XII: 0.25+0.25+1, 0.25+1+0.25, 1+0.25+0.25, 1+1+2, 1+2+1 and 2+1+1 kg/ha;
I + VIII + XII: 0.25+0.25+1, 0.25+1+0.25, 1+0.25+0.25, 1+1+2, 1+2+1 and 2+1+1 kg/ha;
and, for comparison,
XI. N-p-chlorophenyl-N′,N′-dimethylurea, 2 and 4 kg/ha;
XI + XII + I: 2+1+1 kg/ha.

After 3 to 4 weeks it was ascertained that, at a rate of 1.5 kg/ha, the compositions had a better herbicidal action than the individual compounds I, VI, VII, VIII and XII, combined with the same crop plant compatibility, and that they had, at a rate of 4 kg/ha, better crop plant compatibility than XI and the composition XI + XII + I, combined with the same good herbicidal action.

The results are given below:

| Active ingredient | I | | | | | VI | | | | | VII | | | | |
|---|---|---|---|---|---|---|---|---|---|---|---|---|---|---|---|
| kg/ha | 0.25 | 1 | 1.5 | 2 | 4 | 0.25 | 1 | 1.5 | 2 | 4 | 0.25 | 1 | 1.5 | 2 | 4 |
| Crop plant: | | | | | | | | | | | | | | | |
| Beta vulgaris | 0 | 4 | 5 | 10 | 30 | 0 | 0 | 0 | 0 | 5 | 0 | 0 | 0 | 0 | 0 |
| Unwanted plants: | | | | | | | | | | | | | | | |
| Avena fatua | 10 | 40 | 60 | 80 | 100 | 10 | 27 | 60 | 76 | 90 | 10 | 24 | 45 | 56 | 95 |
| Echinochloa crus-galli | 15 | 50 | 70 | 85 | 100 | 10 | 23 | 35 | 44 | 90 | 9 | 17 | 30 | 40 | 52 |
| Matricaria chamomilla | 5 | 22 | 30 | 40 | 70 | 0 | 0 | 3 | 5 | 10 | 0 | 0 | 2 | 7 | 15 |

| Active ingredient | VIII | XII | XI |
|---|---|---|---|

| Active ingredient kg/ha | I | | | | | VI | | | | VII | | | | |
|---|---|---|---|---|---|---|---|---|---|---|---|---|---|---|
| | 0.25 | 1 | 1.5 | 2 | 4 | 0.25 | 1 | 1.5 | 2 | 4 | 0.25 | 1 | 1.5 | 2 | 4 |
| kg/ha | 0.25 | 1 | 1.5 | 2 | 4 | 0.25 | 1 | 1.5 | 2 | 4 | 2 | 4 | | | |
| Beta vulgaris | 0 | 0 | 0 | 0 | 0 | 0 | 0 | 0 | 0 | 10 | 100 | 100 | | | |
| Avena fatua | 8 | 35 | 50 | 67 | 80 | 3 | 12 | 15 | 20 | 75 | 100 | 100 | | | |
| Echinochloa crus-galli | 5 | 30 | 48 | 61 | 100 | 5 | 13 | 20 | 32 | 75 | 100 | 100 | | | |
| Matricaria chamomilla | 0 | 5 | 10 | 17 | 25 | 15 | 50 | 60 | 85 | 100 | 100 | 100 | | | |

0 = no damage
100 = complete destruction

| Active ingredient kg/ha | I + VI + XII | | | I + VII + XII | | | I + VIII + XII | | |
|---|---|---|---|---|---|---|---|---|---|
| | 0.25+ 0.25+ 1 | 0.25+ 1+ 0.25 | 1+ 0.25+ 0.25 | 0.25+ 0.25+ 1 | 0.25+ 1+ 0.25 | 1 0.25+ 0.25 | 0.25+ 0.25+ 1 | 0.25+ 1+ 0.25 | 1+ 0.25+ 0.25 |
| Crop plant: | | | | | | | | | |
| Beta vulgaris | 0 | 0 | 4 | 0 | 0 | 4 | 0 | 0 | 4 |
| Unwanted plants: | | | | | | | | | |
| Avena fatua | 70 | 80 | 89 | 72 | 74 | 90 | 68 | 83 | 87 |
| Echinochloa crus-galli | 75 | 80 | 98 | 75 | 73 | 95 | 70 | 87 | 92 |
| Matricaria chamomilla | 91 | 62 | 74 | 92 | 60 | 75 | 89 | 63 | 76 |

| Active ingredient kg/ha | I + VI + XII | | | I + VII + XII | | | I + VII + XII | | | I+ XII+XI |
|---|---|---|---|---|---|---|---|---|---|---|
| | 1+1+2 | 1+2+1 | 2+1+1 | 1+1+2 | 1+2+1 | 2+1+1 | 1+1+2 | 1+2+1 | 2+1+1 | 1+1+2 |
| Beta vulgaris | 4 | 4 | 10 | 4 | 4 | 10 | 4 | 10 | 100 | |
| Avena fatua | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 |

0 = no damage
100 = complete destruction

EXAMPLE 7

In the greenhouse, loamy sandy soil was filled into pots and sown with the seeds of various plants. The soil prepared in this manner was subsequently treated with the following amounts of the following individual active ingredients and compositions thereof as dispersions:

I. 2-ethoxy-2,3-dihydro-3,3-dimethyl-5-benzofuranyl methane sulfonate, 0.25, 1 and 1.5 kg/ha;

XII. 1-phenyl-4-amino-5-chloropyridazone-(6), 0.25, 1 and 1.5 kg/ha;

XIII. 3-cyclohexyl-5,6-trimethylene uracil, 0.25, 1 and 1.5 kg/ha;

XIV. 1-(α,α-dimethyl-β-acetoxypropionyl)-3-cyclohexyl-5,6-trimethylene uracil, 0.25, 1 and 1.5 kg/ha;

I + XII + XIII: 0.25+0.25+1, 0.25+1+0.25 and 1+0.25+0.25 kg/ha;

I + XII + XIV: 0.25+0.25+1, 0.25+1+0.25 and 1+0.25+0.25 kg/ha.

After 3 to 4 weeks it was ascertained that the compositions had a better herbidical action than their components, combined with the same good crop plant compatibility.

The results are given below:

| Active ingredient kg/ha | I | | | XII | | | XIII | | | XIV | | |
|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 |
| Crop plant: | | | | | | | | | | | | |
| Beta vulgaris | 0 | 4 | 5 | 0 | 0 | 0 | 0 | 0 | 0 | 0 | 0 | 0 |
| Unwanted plants: | | | | | | | | | | | | |
| Avena fatua | 10 | 40 | 60 | 3 | 10 | 15 | 5 | 18 | 20 | 10 | 20 | 25 |
| Echinochloa crus-galli | 15 | 52 | 70 | 5 | 13 | 20 | 15 | 65 | 70 | 17 | 70 | 70 |
| Matricaria chamomilla | 5 | 22 | 30 | 15 | 50 | 60 | 20 | 70 | 75 | 25 | 78 | 85 |

| Active ingredient kg/ha | I + XII + XIII | | | I + XII + XIV | | |
|---|---|---|---|---|---|---|
| | 0.25+ 0.25+ 1 | 0.25+ 1+ 0.25 | 1+ 0.25+ 0.25 | 0.25+ 0.25+ 1 | 0.25+ 1+ 0.25 | 1+ 0.25+ 0.25 |
| Beta vulgaris | 0 | 0 | 4 | 0 | 0 | 4 |
| Avena fatua | 70 | 63 | 84 | 71 | 67 | 90 |
| Echinochloa crus-galli | 100 | 80 | 100 | 100 | 83 | 93 |
| Matricaria chamomilla | 100 | 100 | 90 | 100 | 100 | 91 |

0 = no damage
100 = complete destruction

EXAMPLE 8

In the greenhouse, loamy sandy soil was filled into pots and sown with the seeds of various plants. The soil prepared in this manner was subsequently treated with the following amounts of the following individual active ingredients and compositions thereof as pastes:

I. 2-ethoxy-2,3-dihydro-3,3-dimethyl-5-benzofuranyl methane sulfonate, 0.25, 1.5 and 2 kg/ha;

IX. 1,1,1-trifluoro-4'-(phenylsulfonyl)-methanesulfone-o-toluidide, 0.25, 1.5 and 2 kg/ha;

X. 3,4,5-tribromo-N,N-α-trimethylpyrazole-1-acetamide, 0.25, 1.5 and 2 kg/ha;

XII. 1-phenyl-4-amino-5-chloropyridazone-(6), 0.25, 1.5 and 2 kg/ha;

I + IX + XII: 0.25+0.25+1.5, 0.25+1.5+0.25 and 1.5+0.25+0.25 kg/ha;
I + X + XII: 0.25+0.25+1.5, 0.25+1.5+0.25 and 1.5+0.25+0.25 kg/ha.

After 3 to 4 weeks it was ascertained that the compositions had a better herbicidal action than their components, combined with the same good crop plant compatibility.

The results are given below: -trifluoro-

III. isopropyl N-3-chlorophenylcarbamate, 0.15, 1.5 and 1.8 kg/ha;
IV. butyn-1-yl-3 N-3-chlorophenylcarbamate, 0.15, 1.5 and 1.8 kg/ha;
V. O-(N-phenylcarbamoyl)-propanonoxime, 0.15, 1.5 and 1.8 kg/ha;
XII. 1-phenyl-4-amino-5-chloropyridazone-(6), 0.15, 1.5 and 1.8 kg/ha;
I + II + XII: 0.15+0.15+1.5, 0.15+1.5+0.15 and

| Active ingredient kg/ha | I | | | IX | | | X | | | XII | | |
|---|---|---|---|---|---|---|---|---|---|---|---|---|
| | 0.25 | 1.5 | 2 | 0.25 | 1.5 | 2 | 0.25 | 1.5 | 2 | 0.25 | 1.5 | 2 |
| Crop plant: | | | | | | | | | | | | |
| Beta vulgaris | 0 | 5 | 10 | 0 | 5 | 10 | 0 | 5 | 7 | 0 | 0 | 0 |
| Unwanted plants: | | | | | | | | | | | | |
| Avena fatua | 10 | 60 | 80 | 0 | 80 | 95 | 20 | 80 | 95 | 3 | 15 | 20 |
| Echinochloa crus-galli | 15 | 70 | 85 | 17 | 78 | 100 | 15 | 75 | 95 | 5 | 20 | 32 |
| Matricaria chamomilla | 5 | 30 | 40 | 10 | 25 | 35 | 5 | 20 | 31 | 15 | 60 | 85 |
| Active ingredient kg/ha | I + XII + IX | | | | | | I + XII + X | | | | | |
| | 0.25+ 0.25+ 1.5 | 0.25+ 1.5+ 0.25 | 1.5+ 0.25+ 0.25 | | | | 0.25+ 0.25+ 1.5 | 0.25+ 1.5+ 0.25 | 1.5+ 0.25+ 0.25 | | | |
| Beta vulgaris | 5 | 0 | 5 | | | | 5 | 0 | 5 | | | |
| Avena fatua | 100 | 70 | 100 | | | | 100 | 80 | 100 | | | |
| Echinochloa crus-galli | 100 | 90 | 100 | | | | 100 | 88 | 100 | | | |
| Matricaria chamomilla | 82 | 100 | 91 | | | | 77 | 100 | 86 | | | |

0 = no damage
100 = complete destruction

EXAMPLE 9

In the greenhouse, various plants were treated at a growth height of from 2 to 10 cm with the following amounts of the following individual active ingredients and compositions thereof as emulsions:

I. 2-ethoxy-2,3-dihydro-3,3-dimethyl-5-benzofuranyl methane sulfonate, 0.15, 1.5 and 1.8 kg/ha;
II. isopropyl N-phenylcarbamate, 0.15, 1.5 and 1.8 kg/ha;

1.5+0.15+0.15 kg/ha;
I + III + XII: 0.15+0.15+1.5, 0.15+1.5+0.15 and 1.5+0.15+0.15 kg/ha;
I + IV + XII: 0.15+0.15+1.5, 0.15+1.5+0.15 and 1.5+0.15+0.15 kg/ha;
I + V + XII: 0.15+0.15+1.5, 0.15+1.5+0.15 and 1.5+0.15+0.15 kg/ha;

After 10 to 14 days it was ascertained that the compositions had a better herbicidal action than their components, combined with the same good crop plant compatibility.

The results are given below:

| Active ingredient kg/ha | I | | | II | | | III | | | IV | | |
|---|---|---|---|---|---|---|---|---|---|---|---|---|
| | 0.15 | 1.5 | 1.8 | 0.15 | 1.5 | 1.8 | 0.15 | 1.5 | 1.8 | 0.15 | 1.5 | 1.8 |
| Crop plants: | | | | | | | | | | | | |
| Beta vulgaris | 0 | 5 | 10 | 0 | 0 | 0 | 0 | 0 | 0 | 0 | 0 | 0 |
| Allium cepa | 0 | 0 | 0 | 0 | 0 | 0 | 0 | 0 | 0 | 0 | 0 | 0 |
| Unwanted plants: | | | | | | | | | | | | |
| Avena fatua | 10 | 60 | 70 | 5 | 47 | 60 | 4 | 43 | 55 | 5 | 38 | 45 |
| Echinochloa crus-galli | 8 | 57 | 66 | 5 | 52 | 62 | 0 | 35 | 40 | 0 | 27 | 35 |
| Matricaria chamomilla | 5 | 50 | 64 | 7 | 48 | 57 | 5 | 40 | 50 | 5 | 35 | 43 |
| Active ingredient kg/ha | V | | | | | | XII | | | | | |
| | 0.15 | 1.5 | 1.8 | | | | 0.15 | 1.5 | 1.8 | | | |
| Beta vulgaris | 0 | 0 | 0 | | | | 0 | 0 | 0 | | | |
| Allium cepa | 0 | 0 | 0 | | | | 0 | 0 | 0 | | | |
| Avena fatua | 4 | 45 | 56 | | | | 0 | 15 | 19 | | | |
| Echinochloa crus-galli | 4 | 49 | 60 | | | | 6 | 40 | 46 | | | |
| Matricaria chamomilla | 5 | 43 | 53 | | | | 8 | 50 | 55 | | | |

0 = no damage
100 = complete destruction

| Active ingredient kg/ha | I + II + XII | | | I + III + XII | | |
|---|---|---|---|---|---|---|
| | 0.15+ 0.15+ 1.5 | 0.15+ 1.5+ 0.15 | 1.5+ 0.15+ 0.15 | 0.15+ 0.15+ 1.5 | 0.15+ 1,5+ 0.15 | 1.5+ 0.15+ 0.15 |
| Crop plants: | | | | | | |
| Beta vulgaris | 0 | 0 | 5 | 0 | 0 | 5 |
| Allium cepa | 0 | 0 | 0 | 0 | 0 | 0 |
| Unwanted plants: | | | | | | |
| Avena fatua | 68 | 92 | 98 | 69 | 90 | 96 |
| Echinochloa crus-galli | 90 | 100 | 100 | 84 | 86 | 94 |
| Matricaria chamomilla | 62 | 92 | 94 | 91 | 83 | 93 |
| Active ingredient | I + IV + XII | | | I + V + XII | | |

-continued

| Active ingredient kg/ha | I + II + XII | | | I + III + XII | | |
|---|---|---|---|---|---|---|
| | 0.15+<br>0.15+<br>1.5 | 0.15+<br>1.5+<br>0.15 | 1.5+<br>0.15+<br>0.15 | 0.15+<br>0.15+<br>1.5 | 0.15+<br>1,5+<br>0.15 | 1.5+<br>0.15+<br>0.15 |
| Beta vulgaris | 0 | 0 | 5 | 0 | 0 | 5 |
| Allium cepa | 0 | 0 | 0 | 0 | 0 | 0 |
| Avena fatua | 70 | 83 | 93 | 65 | 93 | 97 |
| Echinochloa crus-galli | 85 | 79 | 91 | 89 | 96 | 100 |
| Matricaria chamomilla | 91 | 80 | 90 | 93 | 87 | 92 |

0 = no damage
100 = complete destruction

EXAMPLE 10

In the greenhouse, various plants were treated at a growth height of from 2 to 10 cm with the following amounts of the following individual ingredients and compositions thereof as oil dispersions:

II. isopropyl N-phenylcarbamate, 0.25, 0.5, 0.75 and 1 kg/ha;

III. isopropyl N-3-chlorophenylcarbamate, 0.25, 0.5, 0.75 and 1 kg/ha;

IV. butyn-1-yl-3 N-3-chlorophenylcarbamate, 0.25, 0.5, 0.75 and 1 kg/ha;

V. O-(N-phenylcarbamoyl)-propanonoxime, 0.25, 0.5, 0.75 and 1 kg/ha;

VI. α,α-dichloropropionic acid, sodium salt, 0.25, 0.5, 0.75 and 1 kg/ha;

VII. trichloroacetic acid, sodium salt, 0.25, 0.5, 0.75 and 1 kg/ha;

VIII. α,α,β,β-tetrafluoropropionic acid, sodium salt, 0.25, 0.5, 0.75 and 1 kg/ha;

II + VI: 0.25+0.75, 0.75+0.25 and 0.5+0.5 kg/ha;
II + VII: 0.25+0.75, 0.75+0.25 and 0.5+0.5 kg/ha;
III + VI: 0.25+0.75, 0.75+0.25 and 0.5+0.5 kg/ha;
IV + VII: 0.25+0.75, 0.75+0.25 and 0.5+0.5 kg/ha;
V + VI: 0.25+0.75, 0.75+0.25 and 0.5+0.5 kg/ha;
V + VII: 0.25+0.75, 0.75+0.25 and 0.5+0.5 kg/ha;
II + VIII: 0.25+0.75, 0.75+0.25 and 0.5+0.5 kg/ha.

After 12 to 16 days it was ascertained that the compositions had a better herbicidal action than their components, combined with the same good crop plant compatibility.

The results are given below:

| Active ingredient kg/ha | II | | | | III | | | | IV | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 10 | 18 | 25 | 30 | 5 | 12 | 20 | 27 | 8 | 17 | 25 | 30 |
| Echinochloa crus-galli | 8 | 15 | 27 | 35 | 5 | 10 | 14 | 22 | 7 | 11 | 16 | 20 |
| Matricaria chamomilla | 10 | 16 | 25 | 32 | 10 | 16 | 20 | 30 | 8 | 14 | 20 | 26 |
| Active ingredient | | V | | | | VI | | | | VII | | |
| Beta vulgaris | 0 | 0 | 0 | 0 | 0 | 0 | 0 | 0 | 0 | 0 | 0 | 0 |
| Avena fatua | 7 | 15 | 24 | 32 | 11 | 16 | 20 | 27 | 0 | 0 | 3 | 5 |
| Echinochloa crus-galli | 6 | 10 | 20 | 30 | 15 | 22 | 30 | 35 | 0 | 5 | 9 | 10 |
| Matricaria chamomilla | 9 | 15 | 26 | 35 | 6 | 10 | 14 | 15 | 5 | 9 | 13 | 20 |
| Active ingredient | | VIII | | | | | | | | | | |
| Beta vulgaris | 0 | 0 | 0 | 0 | | | | | | | | |
| Avena fatua | 12 | 15 | 20 | 25 | | | | | | | | |
| Echinochloa crus-galli | 10 | 14 | 23 | 30 | | | | | | | | |
| Matricaria chamomilla | 6 | 10 | 17 | 20 | | | | | | | | |

0 = no damage
100 = complete destruction

| Active ingredient kg/ha | II + VI | | | II + VII | | | III + VI | | |
|---|---|---|---|---|---|---|---|---|---|
| | 0.25+<br>0.75 | 0.75+<br>0.25 | 0.5+<br>0.5 | 0.25+<br>0.75 | 0.75+<br>0.25 | 0.5+<br>0.5 | 0.25+<br>0.75 | 0.75+<br>0.25 | 0.5+<br>0.5 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 68 | 75 | 72 | 55 | 62 | 60 | 63 | 60 | 67 |
| Echinochloa crus-galli | 69 | 80 | 75 | 55 | 65 | 58 | 72 | 66 | 70 |
| Matricaria chamomilla | 62 | 70 | 65 | 63 | 69 | 65 | 62 | 63 | 65 |
| Active ingredient | | IV + VII | | | V + VI | | | V + VII | |
| Beta vulgaris | 0 | 0 | 0 | 0 | 0 | 0 | 0 | 0 | 0 |
| Avena fatua | 55 | 58 | 55 | 65 | 73 | 70 | 51 | 63 | 53 |
| Echinochloa crus-galli | 62 | 69 | 65 | 74 | 71 | 69 | 55 | 58 | 55 |
| Matricaria chamomilla | 56 | 60 | 59 | 60 | 70 | 63 | 60 | 70 | 63 |
| Active ingredient | | II + VIII | | | | | | | |
| Beta vulgaris | 0 | 0 | 0 | | | | | | |
| Avena fatua | 68 | 77 | 70 | | | | | | |
| Echinochloa crus-galli | 70 | 74 | 65 | | | | | | |
| Matricaria chamomilla | 65 | 68 | 63 | | | | | | |

0 = no damage
100 = complete destruction

EXAMPLE 11

In the greenhouse, various plants were treated at a growth height of from 2 to 8 cm with the following amounts of the following individual active ingredients and compositions thereof as pastes:

I. 2-ethoxy-2,3-dihydro-3,3-dimethyl-5-benzofuranyl methane sulfonate, 0.25, 0.5, 0.75 and 1 kg/ha;
IX. 1,1,1-trifluor-4'-(phenylsulfonyl)-methanesulfone-o-toluidide, 0.25, 0.5, 0.75 and 1 kg/ha;
X. 3,4,5-tribromo-N,N-α-trimethylpyrazole-1-acetamide, 0.25, 0.5, 0.75 and 1 kg/ha;
I + IX: 0.25+0.75, 0.75+0.25 and 0.25+0.25 kg/ha;
I + X: 0.25+0.75, 0.75+0.25 and 0.25+0.25 kg/ha;
IX + X: 0.25+0.75, 0.75+0.25 and 0.25+0.25 kg/ha;
I + IX + X: 0.25+0.25+0.5, 0.25+0.5+0.25 and 0.5+0.25+0.25 kg/ha.

After 10 to 14 days it was ascertained that the compositions had a better herbicidal action than their components, combined with the same good crop plant compatibility.

The results are given below:

III. isopropyl N-3-chlorophenylcarbamate, 0.15, 1.5 and 1.8 kg/ha;
IV. butyn-1-yl-3 N-3-chlorophenylcarbamate, 0.15, 1.5 and 1.8 kg/ha;
V. O-(N-phenylcaramoyl)-propanonoxime, 0.15, 1.5 and 1.8 kg/ha;
VI. α,α-dichloroprpionic acid, sodium salt, 0.15, 1.5 and 1.8 kg/ha;
VII. trichloropropionic acid, sodium salt, 0.15, 1.5 and 1.8 kg/ha;
VIII. α,α,β,β-tetrafluoropropionic acid, sodium salt, 0.15, 1.5 and 1.8 kg/ha;
I + II + VI: 0.15+0.15+1.5, 0.15+1.5+0.15 and 1.5+0.15+0.15 kg/ha;
I + II + VII: 0.15+0.15+1.5, 0.15+1.5+0.15 and 1.5+0.15+0.15 kg/ha;
I + III + VI: 0.15+0.15+1.5, 0.15+1.5+0.15 and 1.5+0.15+0.15 kg/ha;
I + IV + VI: 0.15+0.15+1.5, 0.15+1.5+0.15 and 1.5+0.15+0.15 kg/ha;
I + IV + VII: 0.15+0.15+1.5, 0.15+1.5+0.15 and 1.5+0.15+0.15 kg/ha;
I + V + VI: 0.15+0.15+1.5, 0.15+1.5+0.15 and 1.5+0.15+0.15 kg/ha;
I + V + VII: 0.15+0.15+1.5, 0.15+1.5+0.15 and 1.5+0.15+0.15 kg/ha;
I + II + VIII: 0.15+0.15+1.5, 0.15+1.5+0.15 and 1.5+0.15+0.15 kg/ha.

After 10 to 15 days it was ascertained that the compositions had a better herbicidal action than their components, combined with the same good crop plant compatibility.

The results are given below:

| Active ingredient kg/ha | I | | | | IX | | | | X | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| Beta vulgaris | 0 | 0 | 0 | 0 | 0 | 0 | 0 | 0 | 0 | 0 | 5 | 7 |
| Unwanted plants: | | | | | | | | | | | | |
| Avena fatua | 17 | 30 | 38 | 55 | 0 | 10 | 38 | 55 | 8 | 17 | 70 | 75 |
| Alopecurus myosuroides | 12 | 27 | 40 | 45 | 12 | 23 | 30 | 34 | 12 | 28 | 35 | 47 |
| Echinochloa crus-galli | 10 | 23 | 30 | 34 | 10 | 20 | 30 | 34 | 9 | 20 | 30 | 50 |
| Active ingredient kg/ha | I + IX | | | I + X | | | IX + X | | |
| | 0.25+0.75 | 0.75+0.25 | 0.25+0.25 | 0.25+0.75 | 0.75+0.25 | 0.25+0.25 | 0.25+0.75 | 0.75+0.25 | 0.25+0.25 |
| Beta vulgaris | 15 | 5 | 5 | 5 | 0 | 0 | 5 | 15 | 5 |
| Avena fatua | 80 | 79 | 60 | 100 | 83 | 63 | 100 | 70 | 50 |
| Alopecurus myosuroides | 70 | 77 | 50 | 80 | 90 | 65 | 71 | 70 | 51 |
| Echinochloa crus-galli | 89 | 87 | 68 | 78 | 77 | 57 | 89 | 87 | 67 |
| Active ingredient kg/ha | I + IX + X | | |
| | 0.25+0.25+0.5 | 0.25+0.5+0.25 | 0.5+0.25+0.25 |
| Beta vulgaris | 5 | 12 | 5 |
| Avena fatua | 75 | 73 | 78 |
| Alopecurus myosuroides | 77 | 74 | 79 |
| Echinochloa crus-galli | 86 | 93 | 90 |

0 = no damage
100 = complete destruction

EXAMPLE 12

In the greenhouse, various plants were treated at a growth height of from 2 to 12 cm with the following amounts of the following individual active ingredients and compositions thereof as dusts:

I. 2-ethoxy-2,3-dihydro-3,3-dimethyl-5-benzofuranyl methane sulfonate, 0.15, 1.5 and 1.8 kg/ha;
II. isopropyl N-phenylcarbamate, 0.15, 1.5 and 1.8 kg/ha;

| Active ingredient kg/ha | I | | | II | | | III | | | IV | | |
|---|---|---|---|---|---|---|---|---|---|---|---|---|
| | 0.15 | 1.5 | 1.8 | 0.15 | 1.5 | 1.8 | 0.15 | 1.5 | 1.8 | 0.15 | 1.5 | 1.8 |
| Crop plant: | | | | | | | | | | | | |
| Beta vulgaris | 0 | 5 | 10 | 0 | 0 | 0 | 0 | 0 | 0 | 0 | 0 | 0 |
| Unwanted plants: | | | | | | | | | | | | |
| Avena fatua | 10 | 60 | 70 | 5 | 47 | 60 | 4 | 43 | 55 | 5 | 38 | 45 |
| Echinochloa crus-galli | 8 | 57 | 66 | 5 | 52 | 62 | 0 | 35 | 40 | 0 | 27 | 35 |
| Alopecurus myosuroides | 12 | 30 | 40 | 10 | 55 | 61 | 10 | 55 | 60 | 13 | 65 | 70 |
| Active ingredient | | V | | | VI | | | VII | | | VIII | |
| Beta vulgaris | 0 | 0 | 0 | 0 | 0 | 0 | 0 | 0 | 0 | 0 | 0 | 0 |
| Avena fatua | 4 | 45 | 56 | 10 | 40 | 50 | 0 | 6 | 8 | 10 | 37 | 45 |
| Echinochloa crus-galli | 4 | 49 | 60 | 12 | 50 | 62 | 0 | 12 | 15 | 5 | 48 | 55 |

-continued

| Active ingredient kg/ha | I 0.15 | I 1.5 | I 1.8 | II 0.15 | II 1.5 | II 1.8 | III 0.15 | III 1.5 | III 1.8 | IV 0.15 | IV 1.5 | IV 1.8 |
|---|---|---|---|---|---|---|---|---|---|---|---|---|
| Alopecurus myosuroides | 8 | 50 | 57 | 10 | 47 | 60 | 7 | 41 | 48 | 9 | 40 | 50 |

0 = no damage
100 = complete destruction

| Active ingredient kg/ha | I + II + VI 0.15+ 0.15+ 1.5 | I + II + VI 0.15+ 1.5+ 0.15 | I + II + VI 1.5+ 0.15+ 0.15 | I + II + VII 0.15+ 0.15+ 1.5 | I + II + VII 0.15+ 1.5+ 0.15 | I + II + VII 1.5+ 0.15+ 0.15 | I + III + VI 0.15+ 0.15+ 1.5 | I + III + VI 0.15+ 1.5+ 0.15 | I + III + VI 1.5+ 0.15+ 0.15 |
|---|---|---|---|---|---|---|---|---|---|
| Crop plant: | | | | | | | | | |
| Beta vulgaris | 0 | 0 | 5 | 0 | 0 | 5 | 0 | 0 | 5 |
| Unwanted plants: | | | | | | | | | |
| Avena fatua | 92 | 100 | 100 | 60 | 94 | 97 | 91 | 96 | 100 |
| Echinochloa crus-galli | 95 | 100 | 100 | 63 | 95 | 93 | 94 | 92 | 100 |
| Alopecurus myosuroides | 100 | 100 | 87 | 96 | 100 | 83 | 100 | 98 | 89 |
| Active ingredient | I + IV + VI | | | I + IV + VII | | | I + V + VI | | |
| Beta vulgaris | 0 | 0 | 5 | 0 | 0 | 5 | 0 | 0 | 5 |
| Avena fatua | 92 | 90 | 100 | 60 | 86 | 98 | 91 | 97 | 100 |
| Echinochloa crus-galli | 93 | 84 | 100 | 68 | 72 | 92 | 93 | 100 | 100 |
| Alopecurus myosuroides | 100 | 100 | 89 | 100 | 100 | 87 | 99 | 100 | 84 |
| Active ingredient | I + V + VII | | | I + II + VIII | | | | | |
| Beta vulgaris | 0 | 0 | 5 | 0 | 0 | 5 | | | |
| Avena fatua | 72 | 92 | 97 | 85 | 100 | 100 | | | |
| Echinochloa crus-galli | 65 | 94 | 95 | 94 | 98 | 100 | | | |
| Alopecurus myosuroides | 94 | 100 | 82 | 96 | 100 | 86 | | | |

0 = no damage
100 = complete destruction

EXAMPLE 13

In the greenhouse, various plants were treated at a growth height of from 2 to 14 cm with the following amounts of the following individual active ingredients and compositions thereof as oil dispersions:

I. 2-ethoxy-2,3-dihydro-3,3-dimethyl-5-benzofuranyl methane sulfonate, 1, 2 and 4 kg/ha;
II. isopropyl N-phenylcarbamate, 1, 2 and 4 kg/ha;
III. isopropyl N-3-chlorophenylcarbamate, 1, 2 and 4 kg/ha;
IV. butyn-1-yl-3 N-3-chlorophenylcarbamate, 1, 2 and 4 kg/ha;
V. O-(N-phenylcarbamoyl)-propanonoxime, 1, 2 and 4 kg/ha;
XII. 1-phenyl-4-amino-5-chloropyridazone-(6), 1, 2 and 4 kg/ha;
I + II + XII: 1+1+2, 1+2+1 and 2+1+1 kg/ha;
I + III + XII: 1+1+2, 1+2+1 and 2+1+1 kg/ha;
I + IV + XII: 1+1+2, 1+2+1 and 2+1+1 kg/ha;
I + V + XII: 1+1+2, 1+2+1 and 2+1+1 kg/ha;
and, for comparison,
XI. N-p-chlorophenyl-N',N'-dimethylurea, 1, 2 and 4 kg/ha;
I + XI + II: 1+2+1 kg/ha;
I + XI + XII: 1+2+1 kg/ha.

After 10 to 14 days it was ascertained that the compositions had better crop plant compatibility than compound XI and the compositions I + XI + II and I + XI + XII, combined with the same good herbicidal action. The results are given below:

| Active ingredient kg/ha | I 1 | I 2 | I 4 | II 1 | II 2 | II 4 | III 1 | III 2 | III 4 | IV 1 | IV 2 | IV 4 |
|---|---|---|---|---|---|---|---|---|---|---|---|---|
| Crop plant: | | | | | | | | | | | | |
| Beta vulgaris | 0 | 20 | 40 | 0 | 0 | 15 | 0 | 0 | 0 | 0 | 0 | 25 |
| Unwanted plants: | | | | | | | | | | | | |
| Avena fatua | 55 | 75 | 100 | 30 | 65 | 98 | 27 | 59 | 98 | 30 | 50 | 98 |
| Echinochloa crus-galli | 45 | 70 | 100 | 35 | 66 | 100 | 22 | 44 | 95 | 20 | 41 | 85 |
| Matricaria chamomilla | 34 | 70 | 100 | 32 | 63 | 97 | 30 | 55 | 96 | 26 | 48 | 98 |
| Active ingredient | V | V | V | XI | XI | XI | XII | XII | XII | | | |
| Beta vulgaris | 0 | 0 | 19 | 100 | 100 | 100 | 0 | 0 | 10 | | | |
| Avena fatua | 32 | 60 | 100 | 70 | 90 | 100 | 12 | 22 | 65 | | | |
| Echinochloa crus-galli | 30 | 67 | 100 | 70 | 90 | 100 | 25 | 53 | 90 | | | |
| Matricaria chamomilla | 35 | 59 | 98 | 90 | 100 | 100 | 45 | 60 | 100 | | | |

0 = no damage
100 = complete destruction

| Active ingredient kg/ha | I + II + XII 1+1+2 | I + II + XII 1+2+1 | I + II + XII 2+1+1 | I + III + XII 1+1+2 | I + III + XII 1+2+1 | I + III + XII 2+1+1 | I + IV + XII 1+1+2 | I + IV + XII 1+2+1 | I + IV + XII 2+1+1 |
|---|---|---|---|---|---|---|---|---|---|
| Crop plant: | | | | | | | | | |
| Beta vulgaris | 0 | 0 | 20 | 0 | 0 | 20 | 0 | 0 | 20 |
| Unwanted plants: | | | | | | | | | |
| Avena fatua | 100 | 100 | 100 | 100 | 100 | 100 | 100 | 100 | 100 |
| Echinochloa crus-galli | 100 | 100 | 100 | 100 | 100 | 100 | 100 | 100 | 100 |

-continued

| Active ingredient kg/ha | I + II + XII | | | I + III + XII | | | I + IV + XII | | |
|---|---|---|---|---|---|---|---|---|---|
| | 1+1+2 | 1+2+1 | 2+1+1 | 1+1+2 | 1+2+1 | 2+1+1 | 1+1+2 | 1+2+1 | 2+1+1 |
| Matricaria chamomilla | 100 | 100 | 100 | 100 | 100 | 100 | 100 | 100 | 100 |
| Active ingredient kg/ha | I + V + XII | | | I + XI + XII | | | I + XI + II | | |
| | 1+1+2 | 1+2+1 | 2+1+1 | | 1+2+1 | | | 1+2+1 | |
| Beta vulgaris | 0 | 0 | 20 | | 100 | | | 100 | |
| Avena fatua | 100 | 100 | 100 | | 100 | | | 100 | |
| Echinochloa crus-galli | 100 | 100 | 100 | | 100 | | | 100 | |
| Matricaria chamomilla | 100 | 100 | 100 | | 100 | | | 100 | |

0 = no damage
100 = complete destruction

EXAMPLE 14

In the open, various plants were treated at a growth height of from 2 to 15 cm with the following amounts of the following individual active ingredients and compositions thereof as oil dispersions:

I. 2-ethoxy-2,3-dihydro-3,3-dimethyl-5-benzofuranyl methane sulfonate, 0.25, 1 and 1.5 kg/ha;
XII. 1-phenyl-4-amino-5-chloropyridazone-(6), 0.25, 1 and 1.5 kg/ha;
XIII. 3-cyclohexyl-5,6-trimethylene uracil, 0.25, 1 and 1.5 kg/ha;
XIV. 1-$\alpha$,$\alpha$-dimethyl-$\beta$-acetoxypropionyl-3-cyclohexyl-5,6-trimethylene uracil, 0.25, 1 and 1.5 kg/ha;
I + XII + XIII: 0.25+0.25+1, 0.25+1+0.25 and 1+0.25+0.25 kg/ha;
I + XII + XIV: 0.25+0.25+1, 0.25+1+0.25 and 1+0.25+0.25 kg/ha;

After 12 to 15 days it was ascertained that the compositions had a better herbicidal action than their components, combined with the same good crop plant compatibility.

The results are given below:

EXAMPLE 15

In the greenhouse, various plants were treated at a growth height of from 3 to 17 cm with the following amounts of the following individual active ingredients and compositions thereof as dispersions:

I. 2-ethoxy-2,3-dihydro-3,3-dimethyl-5-benzofuranyl methane sulfonate, 0.25, 1.5 and 2 kg/ha;
IX. 1,1,1-trifluoro-4'-(phenylsulfonyl)-methanesulfone-o-toluidide, 0.25, 1.5 and 2 kg/ha;
XII. 1-phenyl-4-amino-5-chloropyridazone-(6), 0.25, 1.5 and 2 kg/ha;
I + XII + IX: 0.25+0.25+1.5, 0.25+1.5+0.25 and 1.5+0.25+0.25 kg/ha;
I + XII + X: 0.25+0.25+1.5, 0.25+1.5+0.25 and 1.5+0.25+0.25 kg/ha.

After 10 to 12 days it was ascertained that the compositions had a better herbicidal action than their components, combined with the same good crop plant compatibility.

The results are given below:

| Active ingredient kg/ha | I | | | XII | | | XIII | | | XIV | | |
|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 |
| Crop plant: | | | | | | | | | | | | |
| Beta vulgaris | 0 | 0 | 5 | 0 | 0 | 0 | 0 | 0 | 0 | 0 | 0 | 6 |
| Unwanted plants: | | | | | | | | | | | | |
| Avena fatua | 17 | 55 | 60 | 7 | 12 | 15 | 10 | 35 | 45 | 7 | 36 | 47 |
| Echinochloa crus-galli | 12 | 45 | 57 | 10 | 25 | 40 | 14 | 48 | 60 | 12 | 40 | 60 |
| Matricaria chamomilla | 10 | 34 | 50 | 15 | 40 | 50 | 15 | 45 | 60 | 15 | 40 | 65 |
| Active ingredient kg/ha | I + XII + XIII | | | | | | I + XII + XIV | | | | | |
| | 0.25+ 0.25+ 1 | | 0.25+ 1+ 0.25 | | 1+ 0.25+ 0.25 | | 0.25+ 0.25+ 1 | | 0.25+ 1+ 0.25 | | 1+ 0.25+ 0.25 | |
| Beta vulgaris | 0 | | 0 | | 0 | | 0 | | 0 | | 0 | |
| Avena fatua | 93 | | 77 | | 100 | | 94 | | 72 | | 100 | |
| Echinochloa crus-galli | 100 | | 87 | | 100 | | 93 | | 86 | | 98 | |
| Matricaria chamomilla | 100 | | 100 | | 97 | | 100 | | 100 | | 95 | |

0 = no damage
100 = complete destruction

| Active ingredient kg/ha | I | | | XII | | | IX | | | X | | |
|---|---|---|---|---|---|---|---|---|---|---|---|---|
| | 0.25 | 1.5 | 2 | 0.25 | 1.5 | 2 | 0.25 | 1.5 | 2 | 0.25 | 1.5 | 2 |
| Crop plant: | | | | | | | | | | | | |
| Malus spp. | 0 | 0 | 0 | 0 | 0 | 0 | 0 | 0 | 0 | 0 | 0 | 0 |
| Unwanted plants: | | | | | | | | | | | | |
| Avena fatua | 17 | 60 | 75 | 7 | 15 | 22 | 0 | 35 | 40 | 8 | 70 | 85 |
| Echinochloa crus-galli | 12 | 57 | 70 | 10 | 40 | 53 | 10 | 50 | 56 | 9 | 70 | 80 |
| Matricaria chamomilla | 10 | 50 | 70 | 15 | 50 | 60 | 8 | 25 | 34 | 15 | 65 | 86 |
| Active ingredient kg/ha | I + XII + IX | | | | | | I + XII + X | | | | | |
| | 0.25+ 0.25+ 1.5 | | 0.25+ 1.5+ 0.25 | | 1.5+ 0.25+ 0.25 | | 0.25+ 0.25+ 1.5 | | 0.25+ 1.5+ 0.25 | | 1.5+ 0.25+ 0.25 | |
| Malus spp. | 0 | | 0 | | 0 | | 0 | | 0 | | 0 | |
| Avena fatua | 92 | | 70 | | 100 | | 100 | | 77 | | 100 | |
| Echinochloa crus-galli | 100 | | 94 | | 100 | | 100 | | 94 | | 100 | |
| Matricaria chamomilla | 87 | | 100 | | 100 | | 100 | | 100 | | 100 | |

0 = no damage
100 = complete destruction

EXAMPLE 16

In the greenhouse, various plants were treated at a growth height of from 2 to 16 cm with the following amounts of the following individual active ingredients and compositions thereof as solutions:

I. 2-ethoxy-2,3-dihydro-3,3-dimethyl-5-benzofuranyl methane sulfonate, 0.25, 0.5 and 1 kg/ha;
XII. 1-phenyl-4-amino-5-chloropyridazone-(6), 0.25, 0.5 and 1 kg/ha;
XI. 4-chlorobutyn-2-yl-1 N-3-chlorophenylcarbamate, 0.25, 0.5 and 1 kg/ha;
XVII. methyl α-chloro-β-(4-chlorophenyl)-propionate, 0.25, 0.5 and 1 kg/ha;
XVIII. 1,2-dimethyl-3,5-diphenylpyrazolium methyl sulfate, 0.25, 0.5 and 1 kg/ha;
I + XII + XV: 0.25+0.25+0.5, 0.25+0.5+0.25 and 0.5+0.25+0.25 kg/ha;
I + XII + XVII: 0.25+0.25+0.5, 0.25+0.5+0.25 and 0.5 + 0.25 + 0.25 kg/ha;
I + XII + XVIII: 0.25+0.25+0.5, 0.25+0.5+0.25 and 0.5+0.25+0.25 kg/ha.

After 12 to 15 days it was ascertained that the compositions had a better herbicidal action than their components, combined with the same good crop plant compatibility.

The results are given below:

amounts of the following individual active ingredients and compositions thereof as dispersions:

I. 2-ethoxy-2,3-dihydro-3,3-dimethyl-5-benzofuranyl methane sulfonate, 0.25, 1, 1.5, 2 and 4 kg/ha;
VI. α,α-dichloropropionic acid, sodium salt, 0.25, 1, 1.5, 2 and 4 kg/ha;
VII. trichloroacetic acid, sodium salt, 0.25, 1, 1.5, 2 and 4 kg/ha;
VIII. α,α,β,β-tetrafluoropropionic acid, sodium salt, 0.25, 1, 1.5, 2 and 4 kg/ha;
XII. 1-phenyl-4-amino-5-chloropyridazone-(6), 0.25, 1, 1.5, 2 and 4 kg/ha;
I + VI + XII: 0.25+0.25+1, 0.25+1+0.25, 1+0.25+0.25, 1+1+2, 1+2+1 and 2+1+1 kg/ha;
I + VII + XII: 0.25+0.25+1, 0.25+1+0.25, 1+0.25+0.25, 1+1+2, 1+2+1 and 2+1+1 kg/ha;
I + VIII + XII: 0.25+0.25+1, 0.25+1+0.25, 1+0.25+0.25, 1+1+2, 1+2+1 and 2+1+1 kg/ha;

and, for comparison,

XI. 1-p-chlorophenyl-3,3-dimethylurea, 2 and 4 kg/ha;
I + XII + XI: 1+1+2 kg/ha.

After 10 to 14 days it was ascertained that the compositions I+VI+XII, I+VII+XII and I+VIII+XII had, at a rate of 1.5 kg/ha, a better herbicidal action than their components combined with the same good crop plant compatibility, and, at a rate of 4 kg/ha, better crop plant compatability than XI and the composition I+X-

| Active ingredient kg/ha | I | | | XII | | | XV | | | XVII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 17 | 30 | 55 | 7 | 11 | 12 | 10 | 30 | 70 | 15 | 30 | 45 |
| Echinochloa crus-galli | 12 | 27 | 45 | 10 | 14 | 25 | 0 | 5 | 12 | 0 | 0 | 2 |
| Matricaria chamomilla | 10 | 23 | 34 | 15 | 35 | 45 | 1 | 6 | 10 | 0 | 0 | 2 |
| Active ingredient kg/ha | | | | XVIII 0.25 | 0.5 | 1 | | | | | | |
| Beta vulgaris | | | | 0 | 0 | 0 | | | | | | |
| Avena fatua | | | | 15 | 32 | 49 | | | | | | |
| Echinochloa crus-galli | | | | 0 | 0 | 3 | | | | | | |
| Matricaria chamomilla | | | | 0 | 0 | 5 | | | | | | |

0 = no damage
100 = complete destruction

| Active ingredient kg/ha | I + XII + XV | | | I + XII + XVII | | | I + XII + XVIII | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 91 | 75 | 83 | 91 | 80 | 90 | 90 | 80 | 89 |
| Echinochloa crus-galli | 75 | 65 | 75 | 60 | 64 | 75 | 60 | 63 | 74 |
| Matricaria chamomilla | 70 | 82 | 78 | 63 | 83 | 74 | 62 | 81 | 77 |

0 = no damage
100 = complete destruction

EXAMPLE 17

In the greenhouse, various plants were treated at a growth height of from 2 to 8 cm with the following II+XI, combined with the same good herbicidal action.
The results are given below:

| Active ingredient kg/ha | I | | | | | VI | | | | | VII | | |
|---|---|---|---|---|---|---|---|---|---|---|---|---|---|
| | 0.25 | 1 | 1.5 | 2 | 4 | 0.25 | 1 | 1.5 | 2 | 4 | 0.25 | 1 | 1.5 | 2 |
| Crop plant: | | | | | | | | | | | | | | |
| Beta vulgaris | 0 | 0 | 5 | 20 | 40 | 0 | 0 | 0 | 0 | 10 | 0 | 0 | 0 | 0 |
| Unwanted plants: | | | | | | | | | | | | | | |

-continued

| Active ingredient kg/ha | I 0.25 | 1 | 1.5 | 2 | 4 | VI 0.25 | 1 | 1.5 | 2 | 4 | VII 0.25 | 1 | 1.5 | 2 | 4 |
|---|---|---|---|---|---|---|---|---|---|---|---|---|---|---|---|
| *Avena fatua* | 17 | 55 | 60 | 75 | 100 | 11 | 27 | 40 | 60 | 98 | 0 | 5 | 6 | 15 | 40 |
| *Echinochloa crus-galli* | 12 | 45 | 57 | 70 | 100 | 15 | 35 | 50 | 70 | 100 | 0 | 10 | 12 | 20 | 48 |
| *Matricaria chamomilla* | 10 | 34 | 50 | 70 | 100 | 6 | 15 | 20 | 30 | 70 | 5 | 20 | 30 | 40 | 75 |

| Active ingredient kg/ha | VIII 0.25 | 1 | 1.5 | 2 | 4 | XII 0.25 | 1 | 1.5 | 2 | 4 | XI 2 | 4 |
|---|---|---|---|---|---|---|---|---|---|---|---|---|
| *Beta vulgaris* | 0 | 0 | 0 | 0 | 10 | 0 | 0 | 0 | 0 | 10 | 100 | 100 |
| *Avena fatua* | 12 | 25 | 37 | 55 | 97 | 7 | 15 | 15 | 22 | 65 | 90 | 100 |
| *Echinochloa crus-galli* | 10 | 30 | 48 | 63 | 100 | 10 | 25 | 40 | 63 | 90 | 100 | 100 |
| *Matricaria chamomilla* | 6 | 20 | 30 | 40 | 80 | 15 | 45 | 50 | 60 | 100 | 100 | 100 |

0 = no damage
100 = complete destruction

| Active ingredient kg/ha | I + VI + XII 0.25+ 0.25+ 1 | 0.25+ 1+ 0.25 | 1+ 0.25+ 0.25 | I + VII + XII 0.25+ 0.25+ 1 | 0.25+ 1+ 0.25 | 1+ 0.25+ 0.25 | I + VIII + XII 0.25+ 0.25+ 1 | 0.25+ 1+ 0.25 | 1+ 0.25+ 0.25 |
|---|---|---|---|---|---|---|---|---|---|
| Crop plant: | | | | | | | | | |
| *Beta vulgaris* | 0 | 0 | 0 | 0 | 0 | 0 | 0 | 0 | 0 |
| Unwanted plants: | | | | | | | | | |
| *Avena fatua* | 80 | 84 | 100 | 70 | 62 | 94 | 82 | 87 | 100 |
| *Echinochloa crus-galli* | 90 | 93 | 100 | 74 | 70 | 92 | 83 | 89 | 97 |
| *Matricaria chamomilla* | 93 | 78 | 91 | 95 | 82 | 90 | 93 | 92 | 90 |

| Active ingredient kg/ha | I + VI + XII 1+1+2 | 1+2+1 | 2+1+1 | I + VII + XII 1+1+2 | 1+2+1 | 2+1+1 | I + VIII + XII 1+1+2 | 1+2+1 | 2+1+1 | I+XII+XI 1+1+2 |
|---|---|---|---|---|---|---|---|---|---|---|
| *Beta vulgaris* | 0 | 0 | 20 | 0 | 0 | 20 | 0 | 0 | 20 | 100 |
| *Avena fatua* | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 |
| *Matricaria chamomilla* | 100 | 100 | 100 | 100 | 100 | 100 | 100 | 100 | 100 | 100 |

0 = no damage
100 = complete destruction

EXAMPLE 18

In the open, various plants were treated at a growth height of from 2 to 10 cm with the following amounts of the following individual active ingredients and compositions thereof as dispersions:

I. 2-ethoxy-2,3-dihydro-3,3-dimethyl-5-benzofuranyl methane sulfonate, 0.25, 0.5 and 1 kg/ha;
VI. α,α-dichloropropionic acid, sodium slat, 0.25, 0.5 and 1 kg/ha;
XIII. 3-cyclohexyl-5,6-trimethylene uracil, 0.25, 0.5 and 1 kg/ha;
XV. 4-chlorobutyn-2-yl-1 N-3-chlorophenylcarbamate, 0.25, 0.5 and 1 kg/ha;
XVI. 3-methoxycarbonylaminophenyl-N-(3'-methylphenyl)-carbamate, 0.25, 0.5 and 1 kg/ha;
XVII. methyl α-chloro-β-(4-chlorophenyl)-propionate, 0.25, 0.5 and 1 kg/ha;
I + XIII + XV: 0.25+0.25+0.5, 0.25+0.5+0.25 and 0.5+0.25+0.25 kg/ha;
I + XIII + XVII: 0.25+0.25+0.5, 0.25+0.5+0.25 and 0.5+0.25+0.25 kg/ha;
I + XIII + XVI: 0.25 +0.25+0.5, 0.25+0.5+0.25 and 0.5+0.25+0.25 kg/ha;
I + XIII + VI: 0.25+0.25+0.5, 0.25+0.5+0.25 and 0.5+0.25+0.25 kg/ha;

After 12 to 15 days it was ascertained that the compositions had a better herbicidal action than their components, combined with the same good crop plant compatibility.

The results are given below:

| Active ingredient kg/ha | I 0.25 | 0.5 | 1 | VI 0.25 | 0.5 | 1 | XIII 0.25 | 0.5 | 1 | XV 0.25 | 0.5 | 1 |
|---|---|---|---|---|---|---|---|---|---|---|---|---|
| Crop plant: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 17 | 30 | 35 | 11 | 16 | 27 | 10 | 15 | 35 | 10 | 30 | 70 |
| *Echinochloa crus-galli* | 12 | 27 | 45 | 15 | 22 | 35 | 14 | 28 | 48 | 0 | 5 | 12 |
| *Matricaria chamomilla* | 10 | 23 | 34 | 6 | 10 | 15 | 15 | 24 | 45 | 1 | 6 | 10 |

| Active ingredient kg/ha | XVI 0.25 | 0.5 | 1 | XVII 0.25 | 0.5 | 1 |
|---|---|---|---|---|---|---|
| *Beta vulgaris* | 0 | 0 | 0 | 0 | 0 | 0 |
| *Avena fatua* | 0 | 3 | 20 | 15 | 30 | 45 |
| *Echinochloa crus-galli* | 0 | 10 | 15 | 0 | 0 | 2 |

-continued

| Active ingredient kg/ha | I | | | VI | | | XIII | | | XV | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Matricaria chamomilla | 7 | 20 | 30 | 0 | 0 | 2 | | | | | | |

0 = no damage
100 = complete destruction

| Active ingredient kg/ha | I + XIII + XV | | | I + XIII + XVII | | | I + XIII + XVI | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 95 | 76 | 87 | 88 | 80 | 90 | 76 | 72 | 76 |
| Echinochloa crus-galli | 68 | 80 | 76 | 70 | 75 | 78 | 70 | 74 | 72 |
| Matricaria chamomilla | 65 | 70 | 82 | 82 | 70 | 75 | 87 | 85 | 87 |
| Active ingredient | I + XIII + VI | | | | | | | | |
| Beta vulgaris | 0 | 0 | 0 | | | | | | |
| Avena fatua | 77 | 80 | 87 | | | | | | |
| Echinochloa crus-galli | 85 | 90 | 92 | | | | | | |
| Matricaria chamomilla | 70 | 82 | 85 | | | | | | |

0 = no damage
100 = complete destruction

EXAMPLE 19

In the greenhouse, various plants were treated at a growth height of from 1.5 to 12 cm with the following amounts of the following individual active ingredients and compositions thereof as tankmix emulsions:

I. 2-ethoxy-2,3-dihydro-3,3-dimethyl-5-benzofuranyl methane sulfonate, 0.25, 0.5 and 1 kg/ha;
XII. 1-phenyl-4-amino-5-chloropyridazone-(6), 0.25, 0.5 and 1 kg/ha;
XXI. benzyl α,α-dichloropropionate, 0.25, 0.5 and 1 kg/ha;
XXII. β-chloroethyl α,α-dichloropropionate, 0.25, 0.5 and 1 kg/ha;
I + XII + XXI: 0.25+0.25+0.5, 0.25+0.5+0.25 and 0.5+0.25+0.25 kg/ha;
I + XII + XXII: 0.25+0.25+0.5, 0.25+0.5+0.25 and 0.5+0.25+0.25 kg/ha.

After 12 to 15 days it was ascertained that the compositions had a better herbicidal action than their components, combined with the same good crop plant compatibility.

The results are given below:

EXAMPLE 20

In the greenhouse, various plants were treated at a growth height of from 2 to 17 cm with the following amounts of the following individual active ingredients and compositions thereof as oil dispersions:

I. 2-ethoxy-2,3-dihydro-3,3-dimethyl-5-benzofuranyl methane sulfonate, 0.25, 0.5 and 1 kg/ha;
X. 3,4,5-tribromo-N,N-α-trimethylpyrazole-1-acetamide, 0.25, 0.5 and 1 kg/ha;
XII. 1-phenyl-4-amino-5-chloropyridazone-(6), 0.25, 0.5 and 1 kg/ha;
XIII. 3-cyclohexyl-5,6-trimethylene uracil, 0.5, 0.5 and 1 kg/ha;
XVIII. 1,2-dimethyl-3,5-diphenylpyrazolium methyl sulfate, 0.25, 0.5 and 1 kg/ha;
I + X + XVIII: 0.25+0.25+0.5, 0.25+0.5+0.25 and 0.5+0.25+0.25 kg/ha;
I + XII + XVIII: 0.25+0.25+0.5, 0.25+0.5+0.25 and 0.5+0.25+0.25 kg/ha;
I + XIII + XVIII: 0.25+0.25+0.5, 0.25+0.5+0.25 and 0.5+0.25+0.25 kg/ha.

| Active ingredient kg/ha | I | | | XII | | | XXI | | | XXII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 17 | 30 | 55 | 7 | 11 | 12 | 13 | 19 | 30 | 11 | 16 | 28 |
| Echinochloa crus-galli | 12 | 27 | 45 | 10 | 15 | 25 | 18 | 26 | 38 | 15 | 24 | 35 |
| Matricaria chamomilla | 10 | 23 | 34 | 15 | 35 | 45 | 8 | 14 | 18 | 6 | 13 | 16 |
| Active ingredient kg/ha | I + XII + XXI | | | I + XII + XXII | | | | | | | | |
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | | | | | | |
| Beta vulgaris | 0 | 0 | 0 | 0 | 0 | 0 | | | | | | |
| Avena fatua | 81 | 80 | 87 | 78 | 76 | 84 | | | | | | |
| Echinochloa crus-galli | 86 | 82 | 91 | 83 | 80 | 89 | | | | | | |
| Matricaria chamomilla | 78 | 90 | 83 | 75 | 87 | 82 | | | | | | |

0 = no damage
100 = complete destruction

After 12 to 15 days it was ascertained that the compositions had a better herbicidal action than their components, combined with the same good crop plant compatibility.

The results are given below:

| Active ingredient kg/ha | I | | | X | | | XII | | | XIII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 7 | 0 | 0 | 0 | 0 | 0 | 0 |
| Unwanted plants: | | | | | | | | | | | | |
| Avena fatua | 17 | 30 | 55 | 8 | 17 | 75 | 7 | 11 | 12 | 10 | 15 | 35 |
| Echinochloa crus-galli | 12 | 27 | 45 | 9 | 20 | 50 | 10 | 15 | 25 | 14 | 28 | 48 |
| Matricaria chamomilla | 10 | 23 | 34 | 15 | 24 | 43 | 15 | 35 | 45 | 15 | 24 | 45 |

| Active ingredient kg/ha | XVIII | | |
|---|---|---|---|
| | 0.25 | 0.5 | 1 |
| Beta vulgaris | 0 | 0 | 0 |
| Avena fatua | 15 | 32 | 49 |
| Echinochloa crus-galli | 0 | 0 | 3 |
| Matricaria chamomilla | 0 | 0 | 5 |

0 = no damage
100 = complete destruction

| Active ingredient kg/ha | I + XII + X | | | I + XIII + XVIII | | | I + XII + XVIII | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 83 | 76 | 78 | 95 | 83 | 90 | 98 | 79 | 87 |
| Echinochloa crus-galli | 80 | 72 | 86 | 60 | 74 | 76 | 60 | 62 | 72 |
| Matricaria chamomilla | 87 | 85 | 95 | 76 | 70 | 75 | 62 | 86 | 75 |

0 = no damage
100 = complete destruction

EXAMPLE 21

In the greenhouse, various plants were treated at a growth height of from 2 to 19 cm with the following amounts of the following individual active ingredients and compositions thereof as emulsions:

I. 2-ethoxy-2,3-dihydro-3,3-dimethyl-5-benzofuranyl methane sulfonate, 0.25, 0.5 and 1 kg/ha;
XV. 4-chlorobutyn-2-yl-1 N-3-chlorophenylcarbamate, 0.25, 0.5 and 1 kg/ha;
XVI. 3-methoxycarbonylaminophenyl-N-(3'-methylphenyl)-carbamate, 0.25, 0.5 and 1 kg/ha;
XVIII 1,2-dimethyl-3,5-diphenylpyrazolium methyl sulfate, 0.25, 0.5 and 1 kg/ha;
I + XV + XVIII: 0.25+0.25+0.5, 0.25+0.5+0.25 and 0.5+0.25+0.25 kg/ha;
I + XVI + XVIII: 0.25+0.25+0.5, 0.25+0.5+0.25 and 0.5+0.25+0.25 kg/ha.

After 10 to 14 days it was ascertained that the compositions had a better herbicidal action than their components, combined with the same good crop plant compatibility.

The results are given below:

| Active ingredient kg/ha | I | | | XV | | | XVI | | | XVIII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 17 | 30 | 55 | 10 | 30 | 70 | 0 | 3 | 20 | 15 | 32 | 49 |
| Echinochloa crus-galli | 12 | 27 | 45 | 0 | 5 | 12 | 0 | 10 | 15 | 0 | 0 | 3 |
| Matricaria chamomilla | 10 | 23 | 34 | 1 | 6 | 10 | 7 | 20 | 30 | 0 | 0 | 5 |

| Active ingredient kg/ha | I + XV + XVIII | | | I + XVI + XVIII | | |
|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Beta vulgaris | 0 | 0 | 0 | 0 | 0 | 0 |
| Avena fatua | 97 | 95 | 82 | 87 | 70 | 80 |
| Echinochloa crus-galli | 50 | 53 | 64 | 50 | 60 | 62 |
| Matricaria chamomilla | 47 | 50 | 60 | 55 | 66 | 72 |

0 = no damage
100 = complete destruction

EXAMPLE 22

In the open, various plants were treated at a growth height of from 2 to 10 cm with the following amounts of the following individual active ingredient and compositions thereof as dispersions or emulsions:

I. 2-ethoxy-2,3-dihydro-3,3-dimethyl-5-benzofuranyl methane sulfonate, 0.25, 0.5 and 1 kg/ha;
V. α,α-dichloropropionic acid, sodium salt, 0.25, 0.5 and 1 kg/ha;
VII. trichloroacetic acid, sodium salt, 0.25, 0.5 and 1 kg/ha;
XV. 4-chlorobutyn-2-yl-1 N-3-chlorophenylcarbamate, 0.25, 0.5 and 1 kg/ha;
XVI. 3-methoxycarbonylaminophenyl-N-(3'-methylphenyl)-carbamate, 0.25, 0.5 and 1 kg/ha;
XVII methyl α-chloro-β-(4-chlorophenyl)-propionate, 0.25, 0.5 and 1 kg/ha;
I + XV + VI: 0.25+0.25+0.5, 0.25+0.5+0.25 and 0.5+0.25+0.25 kg/ha;
I + XV + VII: 0.25+0.25+0.5, 0.25+0.5+0.25 and 0.5+0.25+0.25 kg/ha;
I + XV + XVII: 0.25+0.25+0.5, 0.25+0.5+0.25 and 0.5+0.25+0.25 kg/ha;
I + XVI + VI: 0.25+0.25+0.5, 0.25+0.5+0.25 and 0.50+0.25+0.25 kg/ha;
I + XVI + VII: 0.25+0.25+0.5, 0.25+0.5+0.25 and 0.5+0.25+0.25 kg/ha;
I + XVI + XVII: 0.25+0.25+0.5, 0.25+0.5+0.25 and 0.5+0.25+0.25 kg/ha.

After 12 to 15 days it was ascertained that the compositions had a better herbicidal action than their components, combined with the same good crop plant compatibility.

The results are given below:

EXAMPLE 23

In the greenhouse, various plants were treated at a growth height of from 2 to 16 cm with the following amounts of the following individual active ingredients and compositions thereof as pastes:

II. isopropyl N-phenylcarbamate, 0.25, 1, 1.75 and 2 kg/ha;
XII. 1-phenyl-4-amino-5-chloropyridazone-(6), 0.25, 1, 1.75 and 2 kg/ha;
XIII. 3-cyclohexyl-5,6-trimethylene uracil, 0.25, 1, 1.75 and 2 kg/ha;
XV. 4-chlorobutyn-2-yl-1 N-3-chlorophenylcarbamate, 0.25, 1, 1.75 and 2 kg/ha;
XVIII. 1,2-dimethyl-3,5-diphenylpyrazolium methyl sulfate, 0.25, 1, 1.75 and 2 kg/ha;
XII + II: 0.25+1.75, 1.75+0.25 and 1+1 kg/ha;
XII + XV: 0.25+1.75, 1.75+0.25 and 1+1 kg/ha;
XII + XVIII: 0.25+1.75, 1.75+0.25 and 1+1 kg/ha;
XIII+XVIII: 0.25+1.75, 1.75+0.25 and 1+1 kg/ha.

After 12 to 15 days it was ascertained that the compositions had a better herbicidal action than their components, combined with the same good crop plant compatibility.

The results are given below:

| Active ingredient kg/ha | I 0.25 | 0.5 | 1 | VI 0.25 | 0.5 | 1 | VII 0.25 | 0.5 | 1 |
|---|---|---|---|---|---|---|---|---|---|
| Crop plants: | | | | | | | | | |
| Beta vulgaris | 0 | 0 | 0 | 0 | 0 | 0 | 0 | 0 | 0 |
| Solanum tuberosum | 0 | 0 | 0 | 0 | 0 | 0 | 0 | 0 | 0 |
| Unwanted plants: | | | | | | | | | |
| Avena fatua | 17 | 30 | 55 | 11 | 16 | 27 | 0 | 0 | 5 |
| Echinochloa crus-galli | 12 | 27 | 45 | 15 | 22 | 35 | 0 | 5 | 10 |
| Matricaria chamomilla | 10 | 23 | 34 | 6 | 10 | 15 | 5 | 9 | 20 |

| Active ingredient kg/ha | XV 0.25 | 0.5 | 1 | XVI 0.25 | 0.5 | 1 | XVII 0.25 | 0.5 | 1 |
|---|---|---|---|---|---|---|---|---|---|
| Beta vulgaris | 0 | 0 | 0 | 0 | 0 | 0 | 0 | 0 | 0 |
| Solanum tuberosum | 0 | 0 | 0 | 0 | 0 | 0 | 0 | 0 | 0 |
| Avena fatua | 10 | 30 | 70 | 0 | 3 | 20 | 15 | 30 | 45 |
| Echinochloa crus-galli | 0 | 5 | 12 | 0 | 10 | 15 | 0 | 0 | 2 |
| Matricaria chamomilla | 1 | 6 | 10 | 7 | 20 | 30 | 0 | 0 | 2 |

0 = no damage
100 = complete destruction

| Active ingredient kg/ha | I + XV + VI 0.25+ 0.25+ 0.5 | 0.25+ 0.5+ 0.25 | 0.5+ 0.25+ 0.25 | I + XV + VII 0.25+ 0.25+ 0.5 | 0.25+ 0.5+ 0.25 | 0.5+ 0.25+ 0.25 | I + XV + XVII 0.25+ 0.25+ 0.5 | 0.25+ 0.5+ 0.25 | 0.5+ 0.25+ 0.25 |
|---|---|---|---|---|---|---|---|---|---|
| Crop plants: | | | | | | | | | |
| Beta vulgaris | 0 | 0 | 0 | 0 | 0 | 0 | 0 | 0 | 0 |
| Solanum tuberosum | 0 | 0 | 0 | 0 | 0 | 0 | 0 | 0 | 0 |
| Unwanted plants: | | | | | | | | | |
| Avena fatua | 76 | 92 | 86 | 70 | 83 | 74 | 95 | 95 | 80 |
| Echinochloa crus-galli | 70 | 67 | 78 | 54 | 52 | 63 | 48 | 55 | 62 |
| Matricaria chamomilla | 60 | 61 | 67 | 63 | 56 | 65 | 44 | 50 | 60 |

| Active ingredient | I + XVI + VI | | | I + XVI + VII | | | I + XVI + XVII | | |
|---|---|---|---|---|---|---|---|---|---|
| Beta vulgaris | 0 | 0 | 0 | 0 | 0 | 0 | 0 | 0 | 0 |
| Solanum tuberosum | 0 | 0 | 0 | 0 | 0 | 0 | 0 | 0 | 0 |
| Avena fatua | 64 | 67 | 76 | 50 | 55 | 65 | 84 | 70 | 82 |
| Echinochloa crus-galli | 70 | 71 | 80 | 55 | 58 | 62 | 47 | 57 | 64 |
| Matricaria chamomilla | 65 | 74 | 60 | 62 | 70 | 76 | 50 | 70 | 72 |

0 = no damage
100 = complete destruction

| Active ingredient kg/ha | II | | | | XII | | | | XIII | | | |
|---|---|---|---|---|---|---|---|---|---|---|---|---|
| | 0.25 | 1 | 1.75 | 2 | 0.25 | 1 | 1.75 | 2 | 0.25 | 1 | 1.75 | 2 |
| Crop plant: | | | | | | | | | | | | |
| Beta vulgaris | 0 | 0 | 0 | 0 | 0 | 0 | 0 | 0 | 0 | 0 | 10 | 15 |
| Unwanted plants: | | | | | | | | | | | | |
| Avena fatua | 10 | 30 | 60 | 65 | 7 | 12 | 19 | 22 | 10 | 35 | 65 | 75 |
| Echinochloa crus-galli | 8 | 35 | 60 | 66 | 10 | 25 | 45 | 53 | 14 | 48 | 67 | 87 |
| Matricaria chamomilla | 10 | 32 | 55 | 63 | 15 | 45 | 55 | 60 | 15 | 45 | 70 | 90 |

| Active ingredient kg/ha | XV | | | | XVIII | | | |
|---|---|---|---|---|---|---|---|---|
| | 0.25 | 1 | 1.75 | 2 | 0.25 | 1 | 1.75 | 2 |
| Beta vulgaris | 0 | 0 | 0 | 0 | 0 | 0 | 5 | 7 |
| Avena fatua | 10 | 70 | 85 | 90 | 15 | 49 | 80 | 83 |
| Echinochloa crus-galli | 0 | 12 | 24 | 30 | 0 | 3 | 5 | 7 |
| Matricaria chamomilla | 1 | 10 | 19 | 24 | 0 | 5 | 10 | 14 |

0 = no damage
100 = complete destruction

| Active ingredient kg/ha | XII + II | | | XII + XV | | | XII + XVIII | | |
|---|---|---|---|---|---|---|---|---|---|
| | 0.25+1.75 | 1.75+0.25 | 1+1 | 0.25+1.75 | 1.75+0.25 | 1+1 | 0.25+1.75 | 1.75+0.25 | 1+1 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 100 | 65 | 80 | 100 | 67 | 100 | 100 | 72 | 94 |
| Echinochloa crus-galli | 100 | 90 | 92 | 72 | 81 | 74 | 55 | 82 | 75 |
| Matricaria chamomilla | 100 | 97 | 100 | 71 | 93 | 91 | 63 | 92 | 87 |

| Active ingredient kg/ha | XIII + XVIII | | |
|---|---|---|---|
| | 0.25+1.75 | 1.75+0.25 | 1+1 |
| Beta vulgaris | 0 | 0 | 0 |
| Avena fatua | 100 | 100 | 100 |
| Echinochloa crus-galli | 58 | 99 | 88 |
| Matricaria chamomilla | 62 | 100 | 82 |

0 = no damage
100 = complete destruction

EXAMPLE 24

In the greenhouse, various plants were treated at a growth height of from 2 to 8 cm with the following amounts of the following individual active ingredients and compositions thereof as dusts:

II. isopropyl N-phenylcarbamate, 0.25, 0.5, 0.75 and 1 kg/ha;

VI. α,α-dichloropropionic acid, sodium salt, 0.25, 0.5, 0.75 and 1 kg/ha;

VII. trichloroacetic acid, sodium salt, 0.25, 0.5, 0.75 and 1 kg/ha;

XIII. 3-cyclohexyl-5,6-trimethylene uracil, 0.25, 0.5, 0.75 and 1 kg/ha;

XV. 4-chlorobutyn-2-yl-1 N-3e-chlorophenylcarbamate, 0.25, 0.5, 0.75 and 1 kg/ha;

XIII + II: 0.25+0.75, 0.75+0.25 and 0.5+0.5 kg/ha;
XIII + VI: 0.25+0.75, 0.75+0.25 and 0.5+0.5 kg/ha;
XIII + VII: 0.25+0.75, 0.75+0.25 and 0.5+0.5 kg/ha;
XIII + XV: 0.25+0.75, 0.75+0.25 and 0.5+0.5 kg/ha.

After 12 to 15 days it was ascertained that the compositions had a better herbicidal action than their components, combined with the same good crop plant compatibility.

The results are given below:

| Active ingredient kg/ha | II | | | | VI | | | | VII | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 10 | 18 | 25 | 30 | 11 | 16 | 20 | 27 | 0 | 0 | 3 | 5 |
| Echinochloa crus-galli | 8 | 15 | 27 | 35 | 15 | 22 | 30 | 35 | 0 | 5 | 9 | 10 |
| Matricaria chamomilla | 10 | 16 | 25 | 32 | 6 | 10 | 14 | 15 | 5 | 9 | 13 | 20 |

| Active ingredient kg/ha | XV | | | | XIII | | | |
|---|---|---|---|---|---|---|---|---|
| | 0.25 | 0.5 | 0.75 | 1 | 0.25 | 0.5 | 0.75 | 1 |
| Beta vulgaris | 0 | 0 | 0 | 0 | 0 | 0 | 0 | 0 |
| Avena fatua | 10 | 30 | 47 | 70 | 10 | 15 | 26 | 35 |
| Echinochloa crus-galli | 0 | 5 | 10 | 12 | 14 | 28 | 40 | 48 |
| Matricaria chamomilla | 1 | 6 | 6 | 10 | 15 | 24 | 35 | 45 |

0 = no damage
100 = complete destruction

| Active ingredient kg/ha | XIII + II | | | XIII + XV | | | XIII + VI | | |
|---|---|---|---|---|---|---|---|---|---|
| | 0.25+ 0.75 | 0.75+ 0.25 | 0.5+ 0.5 | 0.25+ 0.75 | 0.75+ 0.25 | 0.5+ 0.5 | 0.25+ 0.75 | 0.75+ 0.25 | 0.5+ 0.5 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 70 | 86 | 85 | 98 | 84 | 96 | 75 | 87 | 83 |
| Echinochloa crus-galli | 76 | 91 | 79 | 60 | 77 | 70 | 80 | 92 | 87 |
| Matricaria chamomilla | 84 | 77 | 76 | 55 | 70 | 67 | 61 | 78 | 70 |

| Active ingredient kg/ha | XIII + VII | | |
|---|---|---|---|
| | 0.25+ 0.75 | 0.75+ 0.25 | 0.5+ 0.5 |
| Beta vulgaris | 0 | 0 | 0 |
| Avena fatua | 59 | 75 | 68 |
| Echinochloa crus-galli | 60 | 78 | 81 |
| Matricaria chamomilla | 61 | 72 | 77 |

0 = no damage
100 = complete destruction

EXAMPLE 25

In the greenhouse, loamy sandy soil was filled into pots and sown with the seeds of various plants. The soil prepared in this manner was subsequently treated with the following amounts of the following individual active ingredients and compositions thereof as dispersions:

I. 2-ethoxy-2,3-dihydro-3,3-dimethyl-5-benzofuranyl methane sulfonate, 0.25, 1.5 and 2 kg/ha;

II. isopropyl N-phenylcarbamate, 0.25 1.5 and 2 kg/ha;

VI. α,α-dichloropropionic acid, sodium salt, 0.25, 1.5 and 2 kg/ha;

VII. trichloroacetic acid, sodium salt, 0.25, 1.5 and 2 kg/ha;

X. 3,4,5-tribromo-N,N-α-trimethylpyrazole-1-acetamide, 0.25, 1.5 and 2 kg/ha;

XIX. 1-m-trifluoromethylphenyl-4-methylamino-5-chloropyridazone-(6), 0.25, 1.5 and 2 kg/ha;

XX. 1-m-trifluoromethylphenyl-4-dimethylamino-5-chloropyridazone-(6), 0.25, 1.5 and 2 kg/ha;

I + II + X: 0.25+0.25+1.5, 0.25+1.5+0.25 and 1.5+0.25+0.25 kg/ha;

I + VI + XIX: 0.25+0.25+1.5, 0.25+1.5+0.25 and 1.5+0.25+0.25 kg/ha;

I + VI + XX: 0.25+0.25+1.5, 0.25+1.5+0.25 and 1.5+0.25+0.25 kg/ha;

I + VII + XIX: 0.25+0.25+1.5, 0.25+1.5+0.25 and 1.5+0.25+0.25 kg/ha;

I + VII + XX: 0.25+0.25+1.5, 0.25+1.5+0.25 and 1.5+0.25+0.25 kg/ha.

After 12 to 15 days it was ascertained that the compositions had a better herbicidal action than their components, combined with the same good crop plant compatibility.

The results are given below:

| Active ingredient kg/ha | I | | | II | | | VI | | | VII | | |
|---|---|---|---|---|---|---|---|---|---|---|---|---|
| | 0.25 | 1.5 | 2 | 0.25 | 1.5 | 2 | 0.25 | 1.5 | 2 | 0.25 | 1.5 | 2 |
| Crop plant: | | | | | | | | | | | | |
| Gossypium hirsutum | 0 | 0 | 0 | 0 | 0 | 0 | 0 | 0 | 0 | 0 | 0 | 0 |
| Unwanted plants: | | | | | | | | | | | | |
| Amaranthus retroflexus | 10 | 58 | 70 | 12 | 40 | 58 | 0 | 5 | 10 | 0 | 6 | 10 |
| Echinochloa crus-galli | 15 | 70 | 85 | 10 | 30 | 40 | 10 | 35 | 44 | 9 | 30 | 40 |
| Setaria faberii | 15 | 67 | 80 | 10 | 28 | 37 | 13 | 38 | 53 | 10 | 30 | 35 |

| Active ingredient kg/ha | X | | | XIX | | | XX | | |
|---|---|---|---|---|---|---|---|---|---|
| | 0.25 | 1.5 | 2 | 0.25 | 1.5 | 2 | 0.25 | 1.5 | 2 |
| Gossypium hirsutum | 0 | 0 | 0 | 0 | 0 | 0 | 0 | 0 | 0 |
| Amaranthus retroflexus | 15 | 65 | 80 | 5 | 37 | 46 | 5 | 33 | 45 |
| Echinochloa crus-galli | 15 | 75 | 95 | 10 | 53 | 65 | 5 | 37 | 48 |
| Setaria faberii | 13 | 73 | 92 | 5 | 40 | 50 | 4 | 22 | 31 |

0 = no damage
100 = complete destruction

| Active ingredient kg/ha | I + II + X | | | I + VI + XIX | | | I + VI + XX | | |
|---|---|---|---|---|---|---|---|---|---|
| | 0.25+ 0.25+ 1.5 | 0.25+ 1.5+ 0.25 | 1.5+ 0.25+ 0.25 | 0.25+ 0.25+ 1.5 | 0.25+ 1.5+ 0.25 | 1.5+ 0.25+ 0.25 | 0.25+ 0.25+ 1.5 | 0.25+ 1.5+ 0.25 | 1.5+ 0.25+ 0.25 |
| Crop plant: | | | | | | | | | |
| Gossypium hirsutum | 0 | 0 | 0 | 0 | 0 | 0 | 0 | 0 | 0 |
| Unwanted plants: | | | | | | | | | |
| Amaranthus retroflexus | 100 | 97 | 100 | 84 | 59 | 95 | 80 | 60 | 96 |
| Chinochloa crus-galli | 100 | 93 | 100 | 100 | 95 | 100 | 94 | 90 | 100 |
| Setaria faberii | 100 | 90 | 100 | 98 | 92 | 100 | 87 | 91 | 100 |

| Active ingredient | I + VII + XIX | | | I + VII + XX | | |
|---|---|---|---|---|---|---|
| Gossypium hirsutum | 0 | 0 | 0 | 0 | 0 | 0 |
| Amaranthus retroflexus | 83 | 59 | 97 | 79 | 58 | 95 |
| Echinochloa crus1galli | 100 | 92 | 100 | 94 | 88 | 100 |

-continued

| Active ingredient kg/ha | I + II + X | | | I + VI + XIX | | | I + VI + XX | | |
|---|---|---|---|---|---|---|---|---|---|
| | 0.25+ 0.25+ 1.5 | 0.25+ 1.5+ 0.25 | 1.5+ 0.25+ 0.25 | 0.25+ 0.25+ 1.5 | 0.25+ 1.5+ 0.25 | 1.5+ 0.25+ 0.25 | 0.25+ 0.25+ 1.5 | 0.25+ 1.5+ 0.25 | 1.5+ 0.25+ 0.25 |
| Setaria faberii | 98 | 88 | 100 | 85 | 87 | 100 | | | |

0 = no damage
100 = complete destruction

EXAMPLE 26

In the open, various plants were treated at a growth height of from 2 to 10 cm with the following amounts of the following individual active ingredients and compositions thereof as oil dispersions:

I. 2-ethoxy-2,3-dihydro-3,3-dimethyl-5-benzofuranyl methane sulfonate, 0.25, 0.5 and 1 kg/ha;
II. isopropyl N-phenylcarbamate, 0.25, 0.5 and 1 kg/ha;
VI. α,α-dichloropropionic acid, sodium salt, 0.25, 0.5 and 1 kg/ha;
VII. trichloroacetic acid, sodium salt, 0.25, 0.5 and 1 kg/ha;
VIII. α,αβ,β-tetrafluoropropionic acid, sodium salt, 0.25, 0.5 and 1 kg/ha;
IX. 1,1,1-trifluoro-4′-(phenylsulfonyl)-methanesulfone-o-toluidide, 0.25, 0.5 and 1 kg/ha;
X. 3,4,5-tribromo-N,N-α-trimethylpyrazole-1-acetamide, 0.25, 0.5 and 1 kg/ha;
XII. 1-phenyl-4-amino-5-chloropyridazone-(6), 0.25, 0.5 and 1 kg/ha;
XIII. 3-cyclohexyl-5,6-trimethylene uracil, 0.25, 0.5 and 1 kg/ha;
XV. 4-chlorobutyn-2-yl-1 N-3-chlorophenylcarbamate, 0.25, 0.5 and 1 kg/ha;
XVI. 3-methoxycarbonylaminophenyl-N-(3′-methylphenyl)-carbamate, 0.25, 0.5 and 1 kg/ha;
XVIII. methyl α-chloro-β-(4-chlorophenyl)-propionate, 0.25, 0.5 and 1 kg/ha;
XVIII. 1,2-dimethyl-3,5-diphenylpyrazolium methyl sulfate, 0.25, 0.5 and 1 kg/ha;
XI+VII+XIII, XV+VII+XIII, XV+VII+XIII, XVI+ VI+XVIII, XVI+VII+XVIII, XVI+VIII+XVIII, XVI+XVII+XVIII, XVI+VI+XIII, XVI+VII+XII, XVI+VIII+XIII, XVI+XVII+XIII, II+VIII+XIII, II+VII+XIII, XV+VI+XVIII, XV+VII+XVIII, XV+VIII+XVIII, XV+XVII+XVIII, XV+VI+XIII, II+VI+X, II+VII+X, II+VI+XVIII, II+XVII+XVIII, II+VI+IX, II+VI+XIII, II+XVII+XIII, I+II+XVII, I+II+XVIII, I+VI+XVIII, I+XVII+XII, I+XVII+XVIII, I+X+XVIII, I+IX+XVIII, each of these compositions at rates of 0.25+0.25+0.5, 0.25+0.5+0.25 and 0.5+0.25+0.25 kg/ha.

After 12 to 16 days it was ascertained that the compositions had a better herbicidal action than their components, combined with the same good crop plant compatibility.

The results are given below:

| Active ingredient kg/ha | I | | | II | | | VI | | | VII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 17 | 30 | 55 | 10 | 18 | 30 | 11 | 16 | 27 | 0 | 0 | 5 |
| Echinochloa crus-galli | 12 | 27 | 45 | 8 | 15 | 35 | 15 | 22 | 35 | 0 | 5 | 10 |
| Matricaria chamomilla | 10 | 23 | 34 | 10 | 16 | 32 | 6 | 10 | 15 | 5 | 9 | 20 |
| Active ingredient | VIII | | | IX | | | X | | | XII | | |
| Beta vulgaris | 0 | 0 | 0 | 0 | 0 | 0 | 0 | 7 | 0 | 0 | 0 | 0 |
| Avena fatua | 12 | 15 | 25 | 0 | 10 | 55 | 8 | 17 | 75 | 7 | 11 | 12 |
| Echinochloa crus-galli | 10 | 14 | 30 | 10 | 20 | 34 | 9 | 20 | 50 | 10 | 15 | 25 |
| Matricaria chamomilla | 6 | 10 | 20 | 8 | 15 | 20 | 15 | 24 | 43 | 15 | 35 | 45 |

| Active ingredient kg/ha | XIII | | | XV | | | XVI | | | XVII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 10 | 15 | 35 | 10 | 30 | 70 | 0 | 3 | 20 | 15 | 30 | 45 |
| Echinochloa crus-galli | 14 | 28 | 48 | 0 | 5 | 12 | 0 | 10 | 15 | 0 | 0 | 2 |
| Matricaria chamomilla | 15 | 24 | 40 | 1 | 6 | 10 | 7 | 20 | 30 | 0 | 0 | 2 |
| Active ingredient kg/ha | XVIII | | | | | | | | | | | |
| | 0.25 | 0.5 | 1 | | | | | | | | | |
| Beta vulgaris | 0 | 0 | 0 | | | | | | | | | |
| Avena fatua | 15 | 32 | 49 | | | | | | | | | |
| Echinochloa crus-galli | 0 | 0 | 3 | | | | | | | | | |
| Matricaria chamomilla | 0 | 0 | 5 | | | | | | | | | |

0 = no damage
100 = complete destruction

| Active ingredient kg/ha | I + II + XVII | | | I + II + XVIII | | | I + VI + XVIII | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 95 | 87 | 92 | 97 | 85 | 80 | 96 | 85 | 95 |
| Echinochloa crus-galli | 60 | 65 | 70 | 62 | 66 | 72 | 64 | 72 | 80 |
| Matricaria chamomilla | 65 | 62 | 68 | 65 | 62 | 70 | 55 | 58 | 64 |
| Active ingredient | I + XVII + XII | | | I + XVII + XVIII | | | I + X + XVIII | | |
| Beta vulgaris | 0 | 0 | 0 | 0 | 0 | 0 | 0 | 0 | 0 |
| Avena fatua | 80 | 96 | 90 | 100 | 97 | 100 | 95 | 87 | 90 |
| Echinochloa crus-galli | 65 | 50 | 75 | 50 | 50 | 65 | 60 | 70 | 75 |
| Matricaria chamomilla | 87 | 68 | 80 | 50 | 47 | 60 | 67 | 72 | 80 |
| Active ingredient | I + IX + XVIII | | | II + VI + X | | | II + VII + X | | |
| Beta vulgaris | 0 | 0 | 0 | 0 | 0 | 0 | 0 | 0 | 0 |
| Avena fatua | 87 | 80 | 82 | 79 | 70 | 75 | 70 | 60 | 65 |
| Echinochloa crus-galli | 60 | 70 | 75 | 80 | 76 | 77 | 65 | 60 | 67 |
| Matricaria chamomilla | 55 | 67 | 70 | 85 | 72 | 80 | 80 | 75 | 75 |
| Active ingredient | II + VI + XVIII | | | II + XVII + XVIII | | | II + VI + IX | | |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 97 | 86 | 80 | 95 | 92 | 85 | 70 | 65 | 70 |
| Echinochloa crus-galli | 65 | 70 | 68 | 50 | 45 | 54 | 80 | 77 | 78 |
| Matricaria chamomilla | 60 | 65 | 60 | 52 | 50 | 52 | 70 | 66 | 72 |
| Active ingredient | II + VI + XIII | | | II + VII + XIII | | | II + VIII + XIII | | |
| Beta vulgaris | 0 | 0 | 0 | 0 | 0 | 0 | 0 | 0 | 0 |
| Avena fatua | 73 | 75 | 76 | 60 | 58 | 65 | 75 | 72 | 75 |
| Echinochloa crus-galli | 78 | 80 | 82 | 75 | 65 | 68 | 85 | 75 | 76 |
| Matricaria chamomilla | 82 | 72 | 75 | 80 | 75 | 75 | 80 | 72 | 80 |
| Active ingredient | II + XVII + XIII | | | XV + VI + XVIII | | | XV + VII + XVIII | | |
| Beta vulgaris | 0 | 0 | 0 | 0 | 0 | 0 | 0 | 0 | 0 |
| Avena fatua | 76 | 87 | 80 | 90 | 80 | 92 | 80 | 70 | 80 |
| Echinochloa crus-galli | 72 | 60 | 65 | 60 | 60 | 58 | 20 | 40 | 40 |
| Matricaria chamomilla | 72 | 66 | 70 | 40 | 47 | 50 | 35 | 50 | 47 |
| Active ingredient | XV + VIII + XVIII | | | XV + XVII + XVIII | | | XV + VI + XIII | | |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 90 | 77 | 95 | 95 | 90 | 97 | 70 | 72 | 87 |
| Echinochloa crus-galli | 45 | 50 | 50 | 25 | 22 | 42 | 80 | 70 | 70 |
| Matricaria chamomilla | 40 | 45 | 50 | 30 | 28 | 45 | 70 | 60 | 65 |
| Active ingredient | XV + VII + XIII | | | XV + VIII + XIII | | | XV + XVII + XIII | | |
| Beta vulgaris | 0 | 0 | 0 | 0 | 0 | 0 | 0 | 0 | 0 |
| Avena fatua | 68 | 63 | 78 | 75 | 72 | 90 | 76 | 86 | 90 |
| Echinochloa crus-galli | 65 | 57 | 56 | 75 | 65 | 66 | 65 | 50 | 55 |
| Matricaria chamomilla | 70 | 66 | 68 | 73 | 60 | 65 | 62 | 55 | 60 |
| Active ingredient | XVI + VI + XVIII | | | XVI + VII + XVIII | | | XVI + VIII + XVIII | | |
| Beta vulgaris | 0 | 0 | 0 | 0 | 0 | 0 | 0 | 0 | 0 |
| Avena fatua | 80 | 68 | 65 | 70 | 53 | 63 | 80 | 70 | 69 |
| Echinochloa crus-galli | 50 | 60 | 60 | 18 | 40 | 55 | 50 | 52 | 58 |
| Matricaria chamomilla | 55 | 55 | 68 | 50 | 50 | 72 | 50 | 55 | 63 |
| Active ingredient | XVI + XVII + XVIII | | | XVI + VI + XIII | | | XVI + VII + XIII | | |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 84 | 82 | 70 | 58 | 63 | 60 | 52 | 48 | 50 |
| Echinochloa crus-galli | 30 | 22 | 47 | 80 | 73 | 77 | 65 | 57 | 60 |
| Matricaria chamomilla | 45 | 45 | 56 | 75 | 70 | 78 | 72 | 68 | 78 |
| Active ingredient | XVI + VIII + XIII | | | XVI + XVII + XIII | | | | | |
| Beta vulgaris | 0 | 0 | 0 | 0 | 0 | 0 | | | |
| Avena fatua | 65 | 63 | 62 | 68 | 78 | 64 | | | |
| Echinochloa crus-galli | 75 | 64 | 70 | 66 | 62 | 60 | | | |
| Matricaria chamomilla | 74 | 70 | 79 | 69 | 58 | 73 | | | |

0 = no damage
100 = complete destruction

EXAMPLE 27

In the greenhouse, various plants were treated at a growth height of from 2 to 15 cm with the following amounts of the following individual active ingredients and compositions thereof as emulsions:

II. isopropyl N-phenylcarbamate, 0.25 0.5 and 1 kg/ha;

VI. α,α-dichloropropionic acid, sodium salt, 0.25, 0.5 and 1 kg/ha;

VII. trichloroacetic acid, sodium salt, 0.25, 0.5 and 1 kg/ha;

VIII. α,α,β,β-tetrafluoropropionic acid, sodium salt, 0.25, 0.5 and 1 kg/ha;

IX. 1,1,1-trifluoro-4'-(phenylsulfonyl)-methansulfone-o-toluidide, 0.25, 0.5 and 1 kg/ha;

X. 3,4,5-tribromo-N,N-α-trimethylpyrazole-1-acetamide, 0.25, 0.5 and 1 kg/ha;

XII. 1-phenyl-4-amino-5-chloropyridazone-(6), 0.25, 0.5 and 1 kg/ha;
XIII. 3-cyclohexyl-5,6-trimethylene uracil, 0.25, 0.5 and 1 kg/ha;
XV. 4-chlorobutyn-2yl-1 N-3-chlorophenylcarbamate, 0.25, 0.5 and 1 kg/ha;
XVI. 3-methoxycarbonylaminophenyl-N-(3'-methylphenyl)-carbamate, 0.25, 0.5 and 1 kg/ha;
XVII. methyl α-chloro-β-(4-chlorophenyl)-propionate, 0.25, 0.5 and 1 kg/ha;
XVIII. 1,2-dimethyl-3,5-diphenylpyrazolium methyl sulfate, 0.25, 0.5 and 1 kg/ha;

II+VI+XII, II+VII+XII, II+VIII+XII, II+XVII+XII, VI+X+XII, X+XVII+IX, X+XVIII+XIII, X+XVIII+XII, XV+VI+XII, XV+VII+XII, XV+VII+XII, XV+XVII+XII, XVI+VI+XII, XVI+VII+XII, XVI+VII+XII, XVI+XVII+XII, XVII+X+XVIII, XVIII+IX+XII, XVIII+IX+XIII, each of these compositions at rates of 0.25+0.25+0.5, 0.25+0.5+0.25 and 0.5+0.25+0.25 kg/ha.

After 10 to 14 days it was ascertained that the compositions had a better herbicidal action than their components, combined with the same good crop plant compatibility.

The results are given below:

| Active ingredient kg/ha | II | | | VI | | | VII | | | VIII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 10 | 18 | 30 | 11 | 16 | 27 | 0 | 0 | 5 | 12 | 15 | 25 |
| Echinochloa crus-galli | 8 | 15 | 35 | 15 | 22 | 35 | 0 | 5 | 10 | 10 | 14 | 30 |
| Matricaria chamomilla | 10 | 16 | 31 | 6 | 10 | 15 | 5 | 9 | 20 | 6 | 10 | 20 |

| Active ingredient | IX | | | X | | | XII | | | XIII | | |
|---|---|---|---|---|---|---|---|---|---|---|---|---|
| Beta vulgaris | 0 | 0 | 0 | 0 | 0 | 7 | 0 | 0 | 0 | 0 | 0 | 0 |
| Avena fatua | 0 | 10 | 55 | 8 | 17 | 75 | 7 | 11 | 12 | 10 | 15 | 35 |
| Echinochloa crus-galli | 10 | 20 | 34 | 9 | 20 | 50 | 10 | 15 | 25 | 14 | 28 | 48 |
| Matricaria chamomilla | 8 | 15 | 20 | 15 | 24 | 43 | 15 | 35 | 45 | 15 | 24 | 45 |

| Active ingredient | XV | | | XVI | | | XVII | | | XVIII | | |
|---|---|---|---|---|---|---|---|---|---|---|---|---|
| Beta vulgaris | 0 | 0 | 0 | 0 | 0 | 0 | 0 | 0 | 0 | 0 | 0 | 0 |
| Avena fatua | 10 | 30 | 70 | 0 | 3 | 20 | 15 | 30 | 45 | 15 | 32 | 49 |
| Echinochloa crus-galli | 0 | 5 | 12 | 0 | 10 | 15 | 0 | 0 | 2 | 0 | 0 | 3 |
| Matricaria chamomilla | 1 | 6 | 10 | 7 | 20 | 30 | 0 | 0 | 2 | 0 | 0 | 5 |

0 = no damage
100 = complete destruction

| Active ingredient kg/ha | II + VI + XII | | | II + VII + XII | | | II + VIII + XII | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 60 | 70 | 70 | 60 | 54 | 62 | 70 | 68 | 74 |
| Echinochloa crus-galli | 62 | 76 | 74 | 60 | 60 | 63 | 70 | 70 | 70 |
| Matricaria chamomilla | 90 | 76 | 75 | 87 | 70 | 74 | 90 | 76 | 74 |

| Active ingredient | II + XVII + XII | | | VI + X + XII | | | X + XVIII + IX | | |
|---|---|---|---|---|---|---|---|---|---|
| Beta vulgaris | 0 | 0 | 0 | 0 | 0 | 0 | 0 | 0 | 0 |
| Avena fatua | 73 | 83 | 76 | 66 | 70 | 67 | 70 | 75 | 67 |
| Echinochloa crus-galli | 59 | 55 | 63 | 80 | 80 | 77 | 64 | 55 | 65 |
| Matricaria chamomilla | 83 | 67 | 70 | 93 | 87 | 81 | 68 | 60 | 70 |

| Active ingredient | X + XVIII + XIII | | | X + XVIII + XII | | | XV + VI + XII | | |
|---|---|---|---|---|---|---|---|---|---|
| Beta vulgaris | 0 | 0 | 0 | 0 | 0 | 0 | 0 | 0 | 0 |
| Avena fatua | 75 | 85 | 80 | 70 | 83 | 73 | 68 | 70 | 83 |
| Echinochloa crus-galli | 74 | 60 | 70 | 62 | 55 | 65 | 66 | 69 | 65 |
| Matricaria chamomilla | 80 | 72 | 78 | 87 | 73 | 77 | 85 | 64 | 65 |

| Active ingredient | XV + VII + XII | | | XV + VIII + XII | | | XV + XVII + XII | | |
|---|---|---|---|---|---|---|---|---|---|
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 57 | 53 | 74 | 70 | 69 | 84 | 73 | 82 | 88 |
| Echinochloa crus-galli | 52 | 50 | 52 | 63 | 58 | 60 | 52 | 47 | 49 |
| Matricaria chamomilla | 83 | 67 | 63 | 80 | 63 | 66 | 70 | 55 | 60 |

| Active ingredient | XVI + VI + XII | | | XVI + VII + XII | | | XVI + VIII + XII | | |
|---|---|---|---|---|---|---|---|---|---|
| Beta vulgaris | 0 | 0 | 0 | 0 | 0 | 0 | 0 | 0 | 0 |

| Active ingredient kg/ha | II + VI + XII | | | II + VII + XII | | | II + VIII + XII | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| *Avena fatua* | 58 | 60 | 57 | 46 | 42 | 43 | 55 | 56 | 57 |
| *Echinochloa crus-galli* | 67 | 70 | 72 | 51 | 50 | 56 | 61 | 59 | 66 |
| *Matricaria chamomilla* | 90 | 69 | 80 | 85 | 68 | 76 | 83 | 68 | 79 |

| Active ingredient | XVI + XVII + XII | | | XVII + X + XVIII | | | XVIII + IX + XII | | |
|---|---|---|---|---|---|---|---|---|---|
| *Beta vulgaris* | 0 | 0 | 0 | 0 | 0 | 0 | 0 | 0 | 0 |
| *Avena fatua* | 60 | 75 | 61 | 90 | 84 | 88 | 61 | 68 | 74 |
| *Echinochloa crus-galli* | 50 | 44 | 56 | 42 | 56 | 40 | 59 | 65 | 56 |
| *Matricaria chamomilla* | 78 | 60 | 70 | 53 | 60 | 51 | 80 | 71 | 61 |

| Active ingredient | XVIII + IX + XIII | | | XII + XV + XVI | | |
|---|---|---|---|---|---|---|
| Crop plant: | | | | | | |
| *Beta vulgaris* | 0 | 0 | 0 | 0 | 0 | 0 |
| Unwanted plants: | | | | | | |
| *Avena fatua* | 66 | 71 | 78 | 65 | 80 | 64 |
| *Echinochloa crus-galli* | 75 | 70 | 60 | 63 | 60 | 57 |
| *Matricaria chamomilla* | 70 | 67 | 60 | 80 | 70 | 85 |

0 = no damage
100 = complete destruction

EXAMPLE 28

In the greenhouse, various plants were treated at a growth height of from 2 to 12 cm with the following amounts of the following individual active ingredients and compositions thereof as oil dispersions:

I. 2-ethoxy-2,3-dihydro-3,3-dimethyl-5-benzofuranyl methane sulfonate, 0.25, 0.5, 0.75 and 1 kg/ha;

II. isopropyl N-phenylcarbamate, 0.25, 0.5, 0.75 and 1 kg/ha;

VI. α,α-dichloropropionic acid, sodium salt, 0.25, 0.5, 0.75 and 1 kg/ha;

VII. trichloroacetic acid, sodium salt, 0.25, 0.5, 0.75 and 1 kg/ha;

VIII. α,α,β,β-tetrafluoropropionic acid, sodium salt, 0.25, 0.5, 0.75 and 1 kg/ha;

IX. 1,1,1-trifluoro-4′-(phenylsulfonyl)-methane-sulfone-o-toluidide, 0.25, 0.5, 0.75 and 1 kg/ha;

X. 3,4,5-tribromo-N,N-α-trimethylpyrazole-1-acetamide, 0.25, 0.5, 0.75 and 1 kg/ha;

XII. 1-phenyl-4-amino-5-chloropyridazone-(6), 0.25, 0.5, 0.75 and 1 kg/ha;

XIII. 3-cyclohexyl-5,6-trimethylene uracil, 0.25, 0.5, 0.75 and 1 kg/ha;

XIV. 1-(α,α-dimethyl-β-acetoxypropionyl)-3-cyclohexyl-5,6-trimethylene uracil, 0.25, 0.5, 0.75 and 1 kg/ha;

XV. 4-chlorobutyn-2-yl-1 N-3-chlorophenylcarbamate, 0.25, 0.5, 0.75 and 1 kg/ha;

XVI. 3-methoxycarbonylaminophenyl-N-(3′-methylphenyl)-carbamate, 0.25, 0.5, 0.75 and 1 kg/ha;

XVII. methylα-chloro-β-(4-chlorophenyl)-propionate, 0.25, 0.5, 0.75 and 1 kg/ha;

XVIII. 1,2-dimethyl-3,5-diphenylpyrazolium methyl sulfate, 0.25, 0.5, 0.75 and 1 kg/ha;

I+XVIII, II+XIV, II+XVII, II+XVIII, VI+XII, VI+XIV, VI+XV, VI+XVI, VI+XVIII, VII+XII, VII+XV, VII+XVI, VII+XVIII, VIII+XII, VIII+XIII, VIII+XV, VIII+XVI, VIII+XVIII, IX+XVIII, X+XVIII, XV+XIV, XV+XVII, XV+XVIII, XVI+XVII, XVI+XVIII, XVII+XIII, XVII+XIV, XVII+XVIII, XV+XVI, each of these compositions at rate of 0.25+0.75, 0.75+0.25 and 0.5+0.5 kg/ha.

After 10 to 15 days it was ascertained that the compositions had a better herbicidal action than their components, combined with the same good crop plant compatibility.

The results are given below:

| Active ingredient kg/ha | I | | | | II | | | | VI | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 17 | 30 | 38 | 55 | 10 | 18 | 25 | 30 | 11 | 16 | 20 | 27 |
| *Echinochloa crus-galli* | 12 | 27 | 40 | 45 | 8 | 15 | 27 | 35 | 15 | 22 | 30 | 35 |
| *Matricaria chamomilla* | 10 | 23 | 30 | 34 | 10 | 16 | 25 | 32 | 6 | 10 | 14 | 15 |

| Active ingredient | VII | | | | VIII | | | | IX | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 0 | 0 | 3 | 5 | 13 | 15 | 20 | 25 | 0 | 10 | 38 | 55 |
| *Echinochloa crus-galli* | 0 | 5 | 9 | 10 | 10 | 14 | 23 | 30 | 10 | 20 | 30 | 34 |
| *Matricaria chamomilla* | 5 | 9 | 13 | 20 | 6 | 10 | 17 | 20 | 8 | 15 | 18 | 20 |

| Active ingredient | X | | | | XII | | | | XIII | | | |
|---|---|---|---|---|---|---|---|---|---|---|---|---|
| *Beta vulgaris* | 0 | 0 | 5 | 7 | 0 | 0 | 0 | 0 | 0 | 0 | 0 | 0 |
| *Avena fatua* | 8 | 17 | 70 | 75 | 7 | 11 | 12 | 12 | 10 | 15 | 26 | 35 |
| *Echinochloa crus-galli* | 9 | 20 | 30 | 50 | 10 | 15 | 19 | 25 | 14 | 28 | 40 | 48 |
| *Matricaria chamomilla* | 15 | 24 | 37 | 43 | 15 | 35 | 42 | 45 | 15 | 24 | 35 | 45 |

Active ingredient XIV XV XVI

-continued

| Active ingredient kg/ha | I | | | | II | | | | VI | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 7 | 30 | 32 | 36 | 10 | 30 | 47 | 70 | 0 | 3 | 10 | 20 |
| Echinochloa crus-galli | 12 | 20 | 30 | 40 | 0 | 5 | 10 | 12 | 0 | 10 | 14 | 15 |
| Matricaria chamomilla | 14 | 30 | 40 | 50 | 1 | 6 | 6 | 10 | 7 | 20 | 24 | 30 |

| Active ingredient | XVII | | | | XVIII | | | |
|---|---|---|---|---|---|---|---|---|
| Beta vulgaris | 0 | 0 | 0 | 0 | 0 | 0 | 0 | 0 |
| Avena fatua | 15 | 30 | 38 | 45 | 15 | 32 | 40 | 49 |
| Echinochloa crus-galli | 0 | 0 | 0 | 2 | 0 | 0 | 0 | 3 |
| Matricaria chamomilla | 0 | 0 | 0 | 2 | 0 | 0 | 0 | 9 |

0 = no damage
100 = complete destruction

| Active ingredient kg/ha | I + XVIII | | | II + XIV | | | II + XVII | | |
|---|---|---|---|---|---|---|---|---|---|
| | 0.25+0.75 | 0.75+0.25 | 0.5+0.5 | 0.25+0.75 | 0.75+0.25 | 0.5+0.5 | 0.25+0.75 | 0.75+0.25 | 0.5+0.5 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 93 | 90 | 95 | 94 | 75 | 83 | 85 | 76 | 84 |
| Echinochloa crus-galli | 60 | 74 | 64 | 63 | 65 | 57 | 40 | 63 | 52 |
| Matricaria chamomilla | 52 | 72 | 60 | 55 | 67 | 60 | 45 | 66 | 53 |

| Active ingredient | II + XVIII | | | VI + XII | | | VI + XIV | | |
|---|---|---|---|---|---|---|---|---|---|
| Beta vulgaris | 0 | 0 | 0 | 0 | 0 | 0 | 0 | 0 | 0 |
| Avena fatua | 86 | 73 | 86 | 57 | 64 | 62 | 94 | 65 | 81 |
| Echinochloa crus-galli | 42 | 63 | 49 | 70 | 76 | 74 | 62 | 66 | 66 |
| Matricaria chamomilla | 44 | 65 | 54 | 86 | 70 | 83 | 48 | 52 | 50 |

| Active ingredient | VI + XI | | | VI + XVI | | | VI + XVIII | | |
|---|---|---|---|---|---|---|---|---|---|
| Beta vulgaris | 0 | 0 | 0 | 0 | 0 | 0 | 0 | 0 | 0 |
| Avena fatua | 93 | 70 | 82 | 58 | 57 | 55 | 88 | 70 | 85 |
| Echinochloa crus-galli | 61 | 67 | 63 | 65 | 66 | 67 | 52 | 67 | 60 |
| Matricaria chamomilla | 47 | 65 | 57 | 70 | 60 | 68 | 40 | 51 | 47 |

| Active ingredient | XVII + XIII | | | XVII + XIV | | | XVII + XVIII | | |
|---|---|---|---|---|---|---|---|---|---|
| Crop plant: | | | | | | | | | |
| Beta vulgaris | 0 | 0 | 0 | 0 | 0 | 0 | 0 | 0 | 0 |
| Avena fatua | 77 | 83 | 81 | 96 | 83 | 95 | 90 | 87 | 94 |
| Echinochloa crus-galli | 75 | 50 | 63 | 48 | 19 | 39 | 23 | 17 | 20 |
| Matricaria chamomilla | 72 | 52 | 65 | 40 | 35 | 40 | 29 | 25 | 31 |

| Active ingredient | VIII + XIII | | | VIII + XI | | | VIII + XVI | | |
|---|---|---|---|---|---|---|---|---|---|
| Beta vulgaris | 0 | 0 | 0 | 0 | 0 | 0 | 0 | 0 | 0 |
| Avena fatua | 72 | 65 | 64 | 95 | 66 | 82 | 58 | 57 | 54 |
| Echinochloa crus-galli | 86 | 73 | 76 | 57 | 60 | 56 | 60 | 60 | 59 |
| Matricaria chamomilla | 80 | 70 | 71 | 49 | 53 | 50 | 72 | 61 | 68 |

| Active ingredient | VIII + XVIII | | | IX + XVIII | | | X + XVIII | | |
|---|---|---|---|---|---|---|---|---|---|
| Beta vulgaris | 0 | 0 | 0 | 0 | 0 | 0 | 0 | 0 | 0 |
| Avena fatua | 87 | 70 | 82 | 73 | 87 | 76 | 80 | 100 | 85 |
| Echinochloa crus-galli | 46 | 58 | 50 | 46 | 65 | 54 | 48 | 68 | 55 |
| Matricaria chamomilla | 39 | 53 | 47 | 42 | 53 | 55 | 50 | 73 | 60 |

| Active ingredient | VII + XII | | | VII + XV | | | VII + XVI | | |
|---|---|---|---|---|---|---|---|---|---|
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 48 | 46 | 46 | 83 | 55 | 70 | 46 | 39 | 40 |
| Echinochloa crus-galli | 55 | 55 | 54 | 47 | 43 | 46 | 50 | 44 | 51 |
| Matricaria chamomilla | 80 | 64 | 82 | 45 | 50 | 52 | 70 | 63 | 70 |

| Active ingredient | VII + XVIII | | | VIII + XII | | | XV + XVII | | |
|---|---|---|---|---|---|---|---|---|---|
| Beta vulgaris | 0 | 0 | 0 | 0 | 0 | 0 | 0 | 0 | 0 |
| Avena fatua | 74 | 56 | 68 | 60 | 63 | 60 | 82 | 96 | 94 |
| Echinochloa crus-galli | 20 | 44 | 40 | 64 | 68 | 66 | 22 | 47 | 40 |
| Matricaria chamomilla | 38 | 50 | 46 | 80 | 70 | 84 | 30 | 39 | 42 |

| Active ingredient | XV + XVIII | | | XVI + XVII | | | XVI + XVIII | | |
|---|---|---|---|---|---|---|---|---|---|
| Beta vulgaris | 0 | 0 | 0 | 0 | 0 | 0 | 0 | 0 | 0 |
| Avena fatua | 86 | 96 | 97 | 73 | 61 | 67 | 72 | 61 | 70 |
| Echinochloa crus-galli | 24 | 45 | 40 | 20 | 49 | 46 | 22 | 49 | 43 |
| Matricaria chamomilla | 27 | 43 | 39 | 40 | 60 | 58 | 43 | 60 | 56 |

3,933,460

-continued

| Active ingredient kg/ha | I + XVIII | | | II + XIV | | | II + XVII | | |
|---|---|---|---|---|---|---|---|---|---|
| | 0.25+ 0.75 | 0.75+ 0.25 | 0.5+ 0.5 | 0.25+ 0.75 | 0.75+ 0.25 | 0.5+ 0.5 | 0.25+ 0.75 | 0.75+ 0.25 | 0.5+ 0.5 |

| Active ingredient | XV + XIV | | | XV + XVI | | |
|---|---|---|---|---|---|---|
| Crop plant: | | | | | | |
| Beta vulgaris | 0 | 0 | 0 | 0 | 0 | 0 |
| Unwanted plants: | | | | | | |
| Avena fatua | 95 | 93 | 96 | 60 | 95 | 78 |
| Echinochloa crus-galli | 46 | 47 | 47 | 58 | 52 | 60 |
| Matricaria chamomilla | 40 | 42 | 50 | 67 | 50 | 70 |

0 = no damage
100 = complete destruction

EXAMPLE 29

In the greenhouse, loamy sandy soil was filled into pots and sown with the seeds of various plants. The soil prepared in this manner was subsequently treated with the following amounts of the following individual active ingredients and compositions thereof as granules:

I. 2-ethoxy-2,3-dihydro-3,3-dimethyl-5-benzofuranyl methane sulfonate; 0.25, 0.5 and 1 kg/ha;

II. isopropyl N-phenylcarbamate, 0.25, 0.5 and 1 kg/ha;

VI. α,α-dichloropropionic acid, sodium salt, 0.25, 0.5 and 1 kg/ha;

VII. trichloroacetic acid, sodium salt, 0.25, 0.5 and 1 kg/ha;

VIII. α,α,β,β-tetrafluoropropionic acid, sodium salt, 0.25, 0.5 and 1 kg/ha;

IX. 1,1,1-trifluoro-4'-(phenylsulfonyl)-methanesulfone-o-toluidide, 0.25, 0.5 and 1 kg/ha;

X. 3,4,5-tribromo-N,N-α-trimethylpyrazole-1-acetamide, 0.25, 0.5 and 1 kg/ha;

XII. 1-phenyl-4-amino-5-chloropyridazone-(6), 0.25, 0.5 and 1 kg/ha

XIII. 3-cyclohexyl-5,6-trimethylene uracil, 0.25, 0.5 and 1 kg/ha;

VI+X+XIII, VII+X+XIII, VI+X+XII, IX+XIII+XII, II+VI+XIII, II+VII+XIII, II+VIII+XIII, II+VI+XII, II+VII+XII, II+VIII+XII, VI+X+IX, I+VII+XIII, I+VI+XIII, I+IX+XIII, II+VI+X, II+VII+X, II+X, VI+IX, II+VII+IX, I+II+X, I+II+IX, I+II+XIII, I+VI+X, I+VI+IX, II+XII+XIII, I+VII+IX, each of these compositions at rates of 0.25+0.25+0.5, 0.25+0.5+0.25 and 0.5+0.25+0.25 kg/ha.

After 18 to 24 days it was ascertained that the compositions had a better herbicidal action than their components, combined with the same good crop plant compatibility.

The results are given below:

| Active ingredient kg/ha | I | | | II | | | VI | | | VII | | |
|---|---|---|---|---|---|---|---|---|---|---|---|---|
| | 0.25 | 0.5 | 1 | 0.25 | 0.5 | 1 | 0.25 | 0.5 | 1 | 0.25 | 0.5 | 1 |
| Crop plant: | | | | | | | | | | | | |
| Beta vulgaris | 0 | 2.5 | 4 | 0 | 0 | 0 | 0 | 0 | 0 | 0 | 0 | 0 |
| Unwanted plants: | | | | | | | | | | | | |
| Avena fatua | 10 | 16 | 40 | 7 | 12 | 30 | 10 | 15 | 27 | 10 | 10 | 24 |
| Echinochloa crus-galli | 15 | 30 | 50 | 10 | 11 | 18 | 10 | 10 | 23 | 9 | 10 | 17 |
| Matricaria chamomilla | 5 | 9 | 22 | 7 | 18 | 40 | 0 | 0 | 0 | 0 | 0 | 0 |

| Active ingredient | VIII | | | IX | | | X | | | XII | | |
|---|---|---|---|---|---|---|---|---|---|---|---|---|
| Beta vulgaris | 0 | 0 | 0 | 0 | 0 | 0 | 0 | 0 | 0 | 0 | 0 | 0 |
| Avena fatua | 8 | 18 | 35 | 0 | 10 | 25 | 20 | 30 | 67 | 3 | 5 | 12 |
| Echinochloa crus-galli | 5 | 15 | 30 | 17 | 40 | 90 | 15 | 25 | 56 | 5 | 8 | 13 |
| Matricaria chamomilla | 0 | 0 | 5 | 10 | 14 | 19 | 5 | 9 | 15 | 15 | 30 | 50 |

| Active ingredient | XIII | | |
|---|---|---|---|
| Beta vulgaris | 0 | 0 | 0 |
| Avena fatua | 5 | 10 | 18 |
| Echinochloa crus-galli | 16 | 29 | 65 |
| Matricaria chamomilla | 20 | 40 | 70 |

| Active ingredient kg/ha | VII+ XIII | | | VI + X + XIII | | | VI + X + XII | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 68 | 82 | 78 | 76 | 83 | 73 | 71 | 80 | 75 |
| Echinochloa crus-galli | 93 | 87 | 77 | 89 | 78 | 75 | 70 | 78 | 79 |
| Matricaria chamomilla | 82 | 67 | 62 | 82 | 67 | 62 | 72 | 63 | 58 |

| Active ingredient | IX + XIII + XII | | | II + XII + XIII | | | II + VI + XIII | | |
|---|---|---|---|---|---|---|---|---|---|
| Beta vulgaris | 0 | 0 | 0 | 0 | 0 | 0 | 0 | 0 | 0 |
| Avena fatua | 65 | 60 | 65 | 60 | 62 | 65 | 63 | 62 | 64 |
| Echinochloa crus-galli | 79 | 75 | 86 | 87 | 75 | 72 | 86 | 73 | 75 |
| Matricaria chamomilla | 87 | 82 | 85 | 96 | 98 | 95 | 83 | 64 | 77 |

-continued

| Active ingredient kg/ha | 0.25 | I 0.5 | 1 | 0.25 | II 0.5 | 1 | 0.25 | VI 0.5 | 1 | 0.25 | VII 0.5 | 1 |
|---|---|---|---|---|---|---|---|---|---|---|---|---|
| Active ingredient | | II + VII + XIII | | | II + VIII + XIII | | | II + VI + XII | | | | |
| *Beta vulgaris* | 0 | 0 | 0 | 0 | 0 | 0 | 0 | 0 | 0 | | | |
| *Avena fatua* | 61 | 58 | 65 | 62 | 58 | 60 | 57 | 60 | 63 | | | |
| *Echinochloa crus-galli* | 84 | 70 | 74 | 85 | 90 | 80 | 65 | 62 | 64 | | | |
| *Matricaria chamomilla* | 85 | 64 | 75 | 88 | 100 | 83 | 73 | 61 | 70 | | | |
| Active ingredient | | II + XII + XII | | | II + XIII + XII | | | VI + X + IX | | | | |
| Crop plant: | | | | | | | | | | | | |
| *Beta vulgaris* | 0 | 0 | 0 | 0 | 0 | 0 | 0 | 0 | 0 | | | |
| Unwanted plants: | | | | | | | | | | | | |
| *Avena fatua* | 57 | 60 | 62 | 53 | 65 | 58 | 92 | 83 | 79 | | | |
| *Echinochloa crus-galli* | 65 | 60 | 61 | 71 | 80 | 70 | 98 | 88 | 78 | | | |
| *Matricaria chamomilla* | 74 | 59 | 70 | 90 | 94 | 89 | 60 | 55 | 53 | | | |
| Active ingredient | | I + VII + XIII | | | I + VI + XIII | | | I + IX + XII | | | | |
| *Beta vulgaris* | 0 | 0 | 0 | 0 | 0 | 0 | 0 | 0 | 0 | | | |
| *Avena fatua* | 62 | 57 | 68 | 61 | 62 | 68 | 60 | 68 | 67 | | | |
| *Echinochloa crus-galli* | 87 | 75 | 91 | 90 | 79 | 92 | 96 | 94 | 97 | | | |
| *Matricaria chamomilla* | 81 | 62 | 66 | 82 | 62 | 65 | 90 | 77 | 75 | | | |
| Active ingredient | | II + VI + X | | | II + VII + X | | | II + VI + IX | | | | |
| *Beta vulgaris* | 0 | 0 | 0 | 0 | 0 | 0 | 0 | 0 | 0 | | | |
| *Avena fatua* | 86 | 77 | 79 | 81 | 71 | 78 | 70 | 65 | 67 | | | |
| *Echinochloa crus-galli* | 82 | 72 | 74 | 82 | 70 | 72 | 87 | 73 | 75 | | | |
| *Matricaria chamomilla* | 55 | 50 | 60 | 55 | 50 | 61 | 59 | 55 | 64 | | | |
| Active ingredient | | II + VIII + IX | | | I + II + X | | | I + II + IX | | | | |
| Crop plant: | | | | | | | | | | | | |
| *Beta vulgaris* | 0 | 0 | 0 | 0 | 0 | 0 | 0 | 0 | 0 | | | |
| Unwanted plants: | | | | | | | | | | | | |
| *Avena fatua* | 72 | 73 | 79 | 77 | 74 | 75 | 67 | 64 | 65 | | | |
| *Echinochloa crus-galli* | 85 | 69 | 72 | 86 | 78 | 92 | 90 | 78 | 92 | | | |
| *Matricaria chamomilla* | 58 | 50 | 60 | 60 | 65 | 60 | 65 | 70 | 63 | | | |
| Active ingredient | | I + II + XIII | | | I + VI + X | | | I + VII + X | | | | |
| *Beta vulgaris* | 0 | 0 | 0 | 0 | 0 | 0 | 0 | 0 | 0 | | | |
| *Avena fatua* | 56 | 58 | 60 | 82 | 74 | 82 | 81 | 70 | 82 | | | |
| *Echinochloa crus-galli* | 90 | 77 | 92 | 86 | 75 | 90 | 85 | 72 | 91 | | | |
| *Matricaria chamomilla* | 95 | 88 | 85 | 60 | 48 | 50 | 52 | 48 | 50 | | | |
| Active ingredient | | I + VI + IX | | | I + VII + IX | | | | | | | |
| *Beta vulgaris* | 0 | 0 | 0 | 0 | 0 | 0 | | | | | | |
| *Avena fatua* | 72 | 65 | 60 | 69 | 60 | 71 | | | | | | |
| *Echinochloa crus-galli* | 91 | 80 | 90 | 89 | 76 | 92 | | | | | | |
| *Matricaria chamomilla* | 57 | 53 | 55 | 60 | 52 | 56 | | | | | | |

0 = no damage
100 = complete destruction

EXAMPLE 30

In the greenhouse, loamy sandy soil was filled into pots and sown with the seeds of various plants. The soil prepared in this manner was subsequently treated with the following amounts of the following individual active ingredients and compositions thereof as granules:

II. isopropyl N-phenylcarbamate, 0.25, 0.5, 0.75 and 1 kg/ha;

VI. α,α-dichloropropionic acid, sodium salt, 0.25, 0.5, 0.75 and 1 kg/ha;

VII. trichloroacetic acid, sodium salt, 0.25, 0.5, 0.75 and 1 kg/ha;

VIII. α,α,β,β-tetrafluoropropionic acid, sodium salt, 0.25, 0.5, 0.75 and 1 kg/ha;

IX. 1,1,1-trifluoro-4'-(phenylsulfonyl)-methanesulfone-o-toluidide, 0.25, 0.5, 0.75 and 1 kg/ha;

X. 3,4,5-tribromo-N,N-α-trimethylpyrazole-1-acetamide, 0.25, 0.5, 0.75 and 1 kg/ha;

XII. 1-phenyl-4-amino-5-chloropyridazone-(6), 0.25, 0.5, 0.75 and 1 kg/ha;

XIII. 3-cyclohexyl-5,6-trimethylene uracil, 0.25, 0.5, 0.75 and 1 kg/ha;

XIV. 1-(α,α-dimethyl-β-acetoxypropionyl)-3-cyclohexyl-5,6-trimethylene uracil, 0.25, 0.5, 0.75 and 1 kg/ha;

I+XIII, VI+XII, VI+XIII, VI+XIV, VII+IX, VII+X, VII+XII, VII+XIII, II+IX, II+X, VIII+XII, II+XII, II+XIII, II+XIV, VI+IX, VI+X, VIII+IX, VIII+X, VIII+XIII, IX+XII, IX+XIII, and X+XII, each of these compositions at rates of 0.25+0.75, 0.75+0.25 and 0.5+0.5 kg/ha.

After 3 to 4 weeks it was ascertained that the compositions had a better herbicidal action than their components, combined with the same good crop plant compatibility.

The results are given below:

| Active ingredient kg/ha | II | | | | VI | | | | VII | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 7 | 12 | 20 | 30 | 10 | 15 | 21 | 27 | 10 | 10 | 15 | 24 |
| Echinochloa crus-galli | 10 | 11 | 14 | 18 | 10 | 10 | 13 | 23 | 9 | 10 | 11 | 17 |
| Matricaria chamomilla | 7 | 18 | 29 | 40 | 0 | 0 | 0 | 0 | 0 | 0 | 0 | 0 |
| Active ingredient | VIII | | | | IX | | | | X | | | |
| Beta vulgaris | 0 | 0 | 0 | 0 | 0 | 0 | 0 | 0 | 0 | 0 | 0 | 0 |
| Avena fatua | 8 | 18 | 25 | 35 | 0 | 10 | 15 | 25 | 20 | 30 | 56 | 67 |
| Echinochloa crus-galli | 5 | 15 | 20 | 30 | 17 | 40 | 80 | 90 | 15 | 25 | 38 | 56 |
| Matricaria chamomilla | 0 | 0 | 2 | 5 | 10 | 14 | 15 | 19 | 5 | 9 | 12 | 15 |
| Active ingredient | XII | | | | XIII | | | | XIV | | | |
| Beta vulgaris | 0 | 0 | 0 | 0 | 0 | 0 | 0 | 0 | 0 | 0 | 0 | 0 |
| Avena fatua | 3 | 5 | 8 | 12 | 5 | 10 | 15 | 18 | 10 | 12 | 15 | 20 |
| Echinochloa crus-galli | 5 | 8 | 10 | 13 | 16 | 29 | 48 | 65 | 17 | 45 | 60 | 70 |
| Matricaria chamomilla | 15 | 30 | 40 | 50 | 20 | 40 | 56 | 70 | 25 | 40 | 68 | 90 |

0 = no damage
100 = complete destruction

| Active ingredient kg/ha | X + XIII | | | VI + XII | | | VI + XIII | | |
|---|---|---|---|---|---|---|---|---|---|
| | 0.25+ 0.75 | 0.75+ 0.25 | 0.5+ 0.5 | 0.25+ 0.75 | 0.75+ 0.25 | 0.5+ 0.5 | 0.25+ 0.75 | 0.75+ 0.25 | 0.5+ 0.5 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 72 | 95 | 77 | 65 | 63 | 59 | 62 | 63 | 64 |
| Echinochloa crus-galli | 96 | 90 | 91 | 58 | 60 | 55 | 92 | 68 | 76 |
| Matricaria chamomilla | 94 | 70 | 87 | 78 | 52 | 79 | 90 | 59 | 78 |
| Active ingredient | VI + XIV | | | VII + IX | | | VII + X | | |
| Beta vulgaris | 0 | 0 | 0 | 0 | 0 | 0 | 0 | 0 | 0 |
| Avena fatua | 62 | 70 | 65 | 78 | 60 | 70 | 100 | 72 | 78 |
| Echinochloa crus-galli | 100 | 67 | 91 | 90 | 64 | 76 | 83 | 63 | 70 |
| Matricaria chamomilla | 100 | 64 | 77 | 53 | 50 | 52 | 51 | 43 | 46 |
| Active ingredient | VII + XII | | | VII + XIII | | | II + IX | | |
| Beta vulgaris | 0 | 0 | 0 | 0 | 0 | 0 | 0 | 0 | 0 |
| Avena fatua | 60 | 55 | 53 | 63 | 57 | 58 | 74 | 65 | 79 |
| Echinochloa crus-galli | 58 | 55 | 55 | 93 | 65 | 83 | 89 | 69 | 80 |
| Matricaria chamomilla | 79 | 52 | 77 | 91 | 59 | 78 | 60 | 75 | 70 |

0 = no damage
100 = complete destruction

| Active ingredient kg/ha | II + X | | | II + XII | | | II + XIII | | |
|---|---|---|---|---|---|---|---|---|---|
| | 0.25+ 0.75 | 0.75+ 0.25 | 0.5+ 0.5 | 0.25+ 0.75 | 0.75+ 0.25 | 0.5+ 0.5 | 0.25+ 0.75 | 0.75+ 0.25 | 0.5+ 0.5 |
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 97 | 78 | 80 | 60 | 61 | 65 | 60 | 61 | 39 |
| Echinochloa crus-galli | 85 | 67 | 73 | 60 | 56 | 60 | 91 | 69 | 78 |
| Matricaria chamomilla | 65 | 71 | 65 | 83 | 81 | 85 | 100 | 86 | 92 |
| Active ingredient | II + XIV | | | VI + IX | | | VI + X | | |
| Beta vulgaris | 0 | 0 | 0 | 0 | 0 | 0 | 0 | 0 | 0 |
| Avena fatua | 60 | 69 | 62 | 77 | 65 | 72 | 98 | 79 | 80 |
| Echinochloa crus-galli | 100 | 68 | 90 | 89 | 68 | 77 | 83 | 65 | 72 |
| Matricaria chamomilla | 100 | 90 | 93 | 63 | 50 | 52 | 51 | 43 | 47 |
| Active ingredient | VIII + IX | | | VII + X | | | VIII + XII | | |
| Beta vulgaris | 0 | 0 | 0 | 0 | 0 | 0 | 0 | 0 | 0 |
| Avena fatua | 68 | 70 | 75 | 92 | 82 | 84 | 45 | 65 | 60 |
| Echinochloa crus-galli | 85 | 75 | 82 | 80 | 73 | 78 | 53 | 62 | 60 |
| Matricaria chamomilla | 60 | 50 | 51 | 50 | 45 | 46 | 79 | 60 | 70 |

0 = no damage
100 = complete destruction

| Active ingredient kg/ha | VIII + XIII 0.25+ 0.75 | 0.75+ 0.25 | 0.5+ 0.5 | IX + XII 0.25+ 0.75 | 0.75+ 0.25 | 0.5+ 0.5 | IX + XIII 0.25+ 0.75 | 0.75+ 0.25 | 0.5+ 0.5 |
|---|---|---|---|---|---|---|---|---|---|
| Crop plant: | | | | | | | | | |
| Beta vulgaris | 0 | 0 | 0 | 0 | 0 | 0 | 0 | 0 | 0 |
| Unwanted plants: | | | | | | | | | |
| Avena fatua | 53 | 77 | 65 | 60 | 71 | 62 | 61 | 72 | 68 |
| Echinochloa crus-galli | 90 | 73 | 81 | 65 | 85 | 75 | 98 | 93 | 94 |
| Matricaria chamomilla | 93 | 60 | 77 | 87 | 70 | 81 | 100 | 73 | 91 |

| Active ingredient | X + XII | | |
|---|---|---|---|
| Beta vulgaris | 0 | 0 | 0 |
| Avena fatua | 65 | 94 | 73 |
| Echinochloa crus-galli | 61 | 80 | 70 |
| Matricaria chamomilla | 82 | 64 | 76 |

0 = no damage
100 = complete destruction

EXAMPLE 31

An agricultural plot was sown with the seeds of various plants. The soil prepared in this manner was subsequently treated with the following amounts of the following individual active ingredients and compositions thereof as dispersions:

I. 2-ethoxy-2,3-dihydro-3,3-dimethyl-5-benzofuranyl methane sulfonate, 0.25, 1.5 and 2 kg/ha;
II. isopropyl N-phenylcarbamate, 0.25, 1.5 and 2 kg/ha;
VI. α,α-dichloropropionic acid, sodium salt, 0.25, 1.5 and 2 kg/ha;
VII. trichloroacetic acid, sodium salt, 0.25, 1.5 and 2 kg/ha;
X. 3,4,5-tribromo-N,N-α-trimethylpyrazole-1-acetamide, 0.25, 1.5 and 2 kg/ha;
XIX. 1-m-trifluoromethylphenyl-4-methylamino-5-chloropyridazone-(6), 0,25. 1.5 and 2 kg/ha;
XX. 1-m-trifluoromethylphenyl-4-dimethylamino-5-chloropyridazone-(6), 0.25, 1.5 and 2 kg/ha;
I + II + XX: 0.25+0.25+1.5, 0.25+1.5+0.25 and 1.5+0.25+0.25 kg/ha;
II + VI + XIX: 0.25+0.25+1.5, 0.25+1.5+0.25 and 1.5+0.25+0.25 kg/ha;
II + VI + XX: 0.25+0.25+1.5, 0.25+1.5+0.25 and 1.5+0.25+0.25 kg/ha;
II + VII + XIX: 0.25+0.25+1.5, 0.25+1.5+0.25 and 1.5+0.25+0.25 kg/ha;
VI + X + XIX: 0.25+0.25+1.5, 0.25+1.5+0.25 and 1.5+0.25+0.25 kg/ha;
VI + X + XX: 0.25+0.25+1.5, 0.25+1.5+0.25 and 1.5+0.25+0.25 kg/ha.

After 3 to 4 weeks it was ascertained that the compositions had a better herbicidal action than their components, combined with the same good crop plant compatibility.

The results are given below:

| Active ingredient kg/ha | I 0.25 | 1.5 | 2 | II 0.25 | 1.5 | 2 | VI 0.25 | 1.5 | 2 | VII 0.25 | 1.5 | 2 |
|---|---|---|---|---|---|---|---|---|---|---|---|---|
| Crop plant: | | | | | | | | | | | | |
| Gossypium hirsutum | 0 | 0 | 0 | 0 | 0 | 0 | 0 | 0 | 0 | 0 | 0 | 0 |
| Unwanted plants: | | | | | | | | | | | | |
| Amaranthus retroflexus | 10 | 58 | 70 | 12 | 40 | 58 | 0 | 5 | 10 | 0 | 6 | 10 |
| Echinochloa crus-galli | 15 | 70 | 85 | 10 | 30 | 40 | 10 | 35 | 48 | 9 | 30 | 40 |
| Setaria faberii | 15 | 67 | 80 | 10 | 28 | 37 | 15 | 38 | 53 | 10 | 30 | 35 |

| Active ingredient | X | | | XIX | | | XX | | |
|---|---|---|---|---|---|---|---|---|---|
| Gossypium hirsutum | 0 | 0 | 0 | 0 | 0 | 0 | 0 | 0 | 0 |
| Amaranthus retroflexus | 15 | 65 | 80 | 5 | 37 | 46 | 5 | 33 | 45 |
| Echinochloa crus-galli | 15 | 75 | 95 | 10 | 53 | 65 | 5 | 37 | 48 |
| Setaria faberii | 13 | 73 | 92 | 5 | 40 | 50 | 22 | 3 | 31 |

0 = no damage
100 = complete destruction

| Active ingredient kg/ha | I + II + XX 0.25+ 0.25+ 1.5 | 0.25+ 1.5+ 0.25 | 1.5+ 0.25+ 0.25 | II + VI + XIX 0.25+ 0.25+ 1.5 | 0.25+ 1.5+ 0.25 | 1.5+ 0.25+ 0.25 | II + VI + XX 0.25+ 0.25+ 1.5 | 0.25+ 1.5+ 0.25 | 1.5+ 0.25+ 0.25 |
|---|---|---|---|---|---|---|---|---|---|
| Crop plant: | | | | | | | | | |
| Gossypium hirsutum | 0 | 0 | 0 | 0 | 0 | 0 | 0 | 0 | 0 |
| Unwanted plants: | | | | | | | | | |
| Amaranthus retroflexus | 93 | 91 | 100 | 86 | 59 | 81 | 83 | 60 | 82 |
| Echinochloa crus-galli | 95 | 87 | 100 | 100 | 92 | 88 | 92 | 87 | 81 |
| Setaria faberii | 87 | 83 | 100 | 98 | 90 | 85 | 84 | 88 | 88 |

| Active ingredient | II + VII + XIX | | | II + VII + XIX | | | VI + X + XIX | | |
|---|---|---|---|---|---|---|---|---|---|
| Gossypium hirsutum | 0 | 0 | 0 | 0 | 0 | 0 | 0 | 0 | 0 |
| Amaranthus retroflexus | 86 | 61 | 82 | 80 | 61 | 81 | 90 | 100 | 62 |
| Echinochloa crus-galli | 100 | 86 | 92 | 91 | 83 | 80 | 100 | 100 | 95 |
| Setaria faberii | 94 | 82 | 95 | 79 | 81 | 80 | 100 | 100 | 91 |

-continued

| Active ingredient kg/ha | I + II + XX | | | II + VI + XIX | | | II + VI + XX | | |
|---|---|---|---|---|---|---|---|---|---|
| | 0.25+ 0.25+ 1.5 | 0.25+ 1.5+ 0.25 | 1.5+ 0.25+ 0.25 | 0.25+ 0.25+ 1.5 | 0.25+ 1.5+ 0.25 | 1.5+ 0.25+ 0.25 | 0.25+ 0.25+ 1.5 | 0.25+ 1.5+ 0.25 | 1.5+ 0.25+ 0.25 |

| Active ingredient | VI + X + XX | | |
|---|---|---|---|
| Gossypium hirsutum | 0 | 0 | 0 |
| Amaranthus retroflexus | 85 | 100 | 58 |
| Echinochloa crus-galli | 96 | 100 | 92 |
| Setaria faberii | 97 | 100 | 90 |

0 = no damage
100 = complete destruction

EXAMPLE 32

An agricultural plot was sown with the seeds of various plants. The soil prepared in this manner was subsequently treated with the following amounts of the following individual active ingredients and compositions thereof as dispersions:

I. 2-ethoxy-2,3-dihydro-3,3-dimethyl-5-benzofuranyl methane sulfonate, 0.5, 1, 1.5 and 2 kg/ha;
II. isopropyl N-phenylcarbamate, 0.5, 1, 1.5 and 2 kg/ha;
VI. α,α-dichlorpropionic acid, sodium salt, 0.5, 1, 1.5 and 2 kg/ha;
VII. trichloroacetic acid, sodium salt, 0.5, 1, 1.5 and 2 kg/ha;
X. 3,4,5-tribromo-N,N-α-trimethylpyrazole-1-acetamide, 0.5, 1, 1.5 and 2 kg/ha;
XIX. 1-m-trifluoromethylphenyl-4-methylamino-5-chloropyridazone-(6), 0.5, 1, 1.5 and 2 kg/ha;
XX. 1-m-trifluoromethylphenyl-4-dimethylamino-5-chloropyridazone-(6), 0.5, 1, 1.5 and 2 kg/ha;
I + XIX: 0.5+1.5, 1.5+0.5 and 1+1 kg/ha;
I + XX: 0.5 + 1.5, 1.5 + 0.5 and 1 + 1 kg/ha;
II + IX: 0.5+1.5, 1.5+0.5 and 1+1 kg/ha;
II + XX: 0.5+1.5, 1.5+0.5 and 1+1 kg/ha;
VI + XIX: 0.5+1.5, 1.5+0.5 and 1+1 kg/ha;
VII + XIX: 0.5+1.5, 1.5+0.5 and 1+1 kg/ha;
VI + XX: 0.5+1.5, 1.5+0.5 and 1+1 kg/ha;
VII + XX: 0.5+1.5, 1.5+0.5 and 1+1 kg/ha;
X + XX: 0.5+1.5, 1.5+0.5 and 1+1 kg/ha;
X + XIX: 0.5+1.5, 1.5+0.5 and 1+1 kg/ha.

After 3 to 4 weeks it was ascertained that the compositions had a better herbicidal action than their components, combined with the same good crop plant compatibility.

The results are given below:

| Active ingredient kg/ha | I | | | | II | | | | VI | | | |
|---|---|---|---|---|---|---|---|---|---|---|---|---|
| | 0.5 | 1 | 1.5 | 2 | 0.5 | 1 | 1.5 | 2 | 0.5 | 1 | 1.5 | 2 |
| Crop plant: | | | | | | | | | | | | |
| Gossypium hirsutum | 0 | 0 | 0 | 0 | 0 | 0 | 0 | 0 | 0 | 0 | 0 | 0 |
| Unwanted plants: | | | | | | | | | | | | |
| Amaranthus retroflexus | 17 | 30 | 58 | 70 | 20 | 30 | 40 | 58 | 0 | 0 | 5 | 10 |
| Echinochloa crus-galli | 30 | 50 | 70 | 85 | 11 | 18 | 30 | 40 | 10 | 23 | 35 | 48 |
| Setaria faberii | 28 | 52 | 67 | 80 | 18 | 24 | 28 | 37 | 20 | 29 | 38 | 53 |

| Active ingredient kg/ha | VII | | | | X | | | | XIX | | | | XX | | | |
|---|---|---|---|---|---|---|---|---|---|---|---|---|---|---|---|---|
| | 0.5 | 1 | 1.5 | 2 | 0.5 | 1 | 1.5 | 2 | 0.5 | 1 | 1.5 | 2 | 0.5 | 1 | 1.5 | 2 |
| Gossypium hirsutum | 0 | 0 | 0 | 0 | 0 | 0 | 0 | 0 | 0 | 0 | 0 | 0 | 0 | 0 | 0 | 0 |
| Amaranthus retroflexus | 0 | 0 | 6 | 10 | 26 | 42 | 65 | 80 | 12 | 20 | 37 | 46 | 10 | 23 | 33 | 45 |
| Echinochloa crus-galli | 10 | 17 | 30 | 40 | 25 | 56 | 75 | 95 | 15 | 27 | 53 | 65 | 13 | 25 | 37 | 48 |
| Setaria faberii | 14 | 22 | 30 | 35 | 20 | 48 | 73 | 92 | 10 | 24 | 40 | 50 | 8 | 18 | 22 | 31 |

0 = no damage
100 = complete destruction

| Active ingredient kg/ha | I + XIX | | | I + XX | | | II + XIX | | | II + XX | | |
|---|---|---|---|---|---|---|---|---|---|---|---|---|
| | 0.5+ 1.5 | 1.5+ 0.5 | 1+1 | 0.5+ 1.5 | 1.5+ 0.5 | 1+1 | 0.5+ 1.5 | 1.5+ 0.5 | 1+1 | 0.5+ 1.5 | 1.5+ 0.5 | 1+1 |
| Crop plant: | | | | | | | | | | | | |
| Gossypium hirsutum | 0 | 0 | 0 | 0 | 0 | 0 | 0 | 0 | 0 | 0 | 0 | 0 |
| Unwanted plants: | | | | | | | | | | | | |
| Amaranthus retroflexus | 89 | 100 | 87 | 88 | 100 | 90 | 91 | 88 | 86 | 89 | 86 | 89 |
| Echinochloa crus-galli | 100 | 100 | 100 | 99 | 100 | 100 | 96 | 82 | 81 | 85 | 80 | 81 |
| Setaria faberii | 98 | 100 | 100 | 87 | 100 | 100 | 93 | 75 | 84 | 78 | 73 | 79 |

| Active ingredient | VI + XIX | | | VII + XIX | | | VI + XX | | | VII + XX | | |
|---|---|---|---|---|---|---|---|---|---|---|---|---|
| Gossypium hirsutum | 0 | 0 | 0 | 0 | 0 | 0 | 0 | 0 | 0 | 0 | 0 | 0 |
| Amaranthus retroflexus | 74 | 60 | 58 | 75 | 65 | 57 | 70 | 55 | 60 | 70 | 55 | 60 |
| Echinochloa crus-galli | 95 | 86 | 87 | 95 | 81 | 80 | 83 | 85 | 85 | 82 | 80 | 81 |
| Setaria faberii | 93 | 84 | 89 | 90 | 78 | 83 | 80 | 82 | 83 | 73 | 76 | 77 |

| Active ingredient | X + XIX | | | X + XX | | |
|---|---|---|---|---|---|---|
| Gossypium hirsutum | 0 | 0 | 0 | 0 | 0 | 0 |

-continued

| Active ingredient kg/ha | I + XIX | | | I + XX | | | II + XIX | | | II + XX | | |
|---|---|---|---|---|---|---|---|---|---|---|---|---|
| | 0.5+1.5 | 1.5+0.5 | 1+1 | 0.5+1.5 | 1.5+0.5 | 1+1 | 0.5+1.5 | 1.5+0.5 | 1+1 | 0.5+1.5 | 1.5+0.5 | 1+1 |
| Amaranthus retroflexus | 97 | 100 | 97 | 95 | 100 | 98 | | | | | | |
| Echinochloa crus-galli | 100 | 100 | 100 | 94 | 100 | 100 | | | | | | |
| Setaria faberii | 94 | 100 | 100 | 80 | 100 | 98 | | | | | | |

0 = no damage
100 = complete destruction

EXAMPLE 33

In the greenhouse, various plants were treated at a growth height of from 2 to 12 cm with the following amounts of the following individual active ingredients and compositions thereof as tankmix emulsions or dispersions:

I. 2-ethoxy-2,3-dihydro-3,3-dimethyl-5-benzofuranyl methane sulfonate, 0.25, 0.5, 0.75 and 1 kg/ha;

II. isopropyl N-phenylcarbamate, 0.25, 0.5, 0.75 and 1 kg/ha;

VI. $\alpha,\alpha$-dichloropropionic acid, sodium salt, 0.25, 0.5, 0.75 and 1 kg/ha;

VIII. $\alpha,\alpha, \beta,\beta$-tetrafluoropropionic acid, sodium salt, 0.25, 0.5, 0.75 and 1 kg/ha;

X. 3,4,5-tribromo-N,N-$\alpha$-trimethylpyrazole-1-acetamide, 0.25, 0.5, 0.75 and 1 kg/ha;

XII. 1-phenyl-4-amino-5-chloropyridazone-(6), 0.25, 0.5, 0.75 and 1 kg/ha;

XIII. 3-cyclohexyl-5,6-trimethylene uracil, 0.25, 0.5, 0.75 and 1 kg/ha;

XV. 4-chlorobutyn-2-yl-1 N-3-chlorophenylcarbamate, 0.25, 0.5, 0.75 and 1 kg/ha;

XVI. 3-methoxycarbonylaminophenyl-N-(3'-methylphenyl)carbamate, 0.25, 0.5, 0.75 and 1 kg/ha;

XVII. methyl $\alpha$-chloro-$\beta$-(4-chlorophenyl)-propionate, 0.25, 0.5, 0.75 and 1 kg/ha;

XVIII. 1,2-dimethyl-3,5-diphenylpyrazolium methyl sulfate, 0.25, 0.5, 0.75 and 1 kg/ha;

XV+XVI+X, II+XVII+X, XVI+XVII+X, XV+XVI+X, XV+XVII+X, II+VIII+X, XVI+VIII+X, XV+VIII+X, XVII+XII+X, XVI+XVIII+X, XVI+XIII+X, XVI+XII+X, XV+XII+X, VI+XVIII+X, XVII+XIII+X, I+XIII+X, I+XII+X, II+XVIII+X, II+XIII+X, II+XII+X, XV+XVIII+X, XV+XIII+X, I+XV+X, I+XVII+X, XVI+XVII+X-III, XV+XVII+XVIII, II+VIII+XVIII, II+VIII+XII, XVIII+XIII+XII, VI+XIII+XVII, VIII+XIII+XII, XVI+XVIII+XII, VI+XVIII+XIII, VI+XVIII+XII, XVII+XVIII+XIII, XVII+XVIII+XII, XVII+X-III+XII, II+XVIII+XIII, II+XVIII+XII, XV+XVIII+XIII, XV+XVIII+XII, XVI+XVIII+X-III, I+II+XIII, I+XVI+XII, I+XV+XVI, I+II+XV, I+II+XVI, each of these compositions at a rate of 0.25+0.25+0.5, 0.25+0.5+0.25 and 0.5 + 0.25 + 0.25 kg/ha;

I+II, I+XV, I+VI, I+VIII, I+XVII, XVI+X, XV+VIII, XV+X, VIII+X, XVII+X, X+XIII, X+XII, each of these compositions at a rate of 0.25+0.75, 0.75+0.25 and 0.5+0.5 kg/ha.

After 10 to 14 days it was ascertained that the compositions had a better herbicidal action than their components, combined with the same good crop plant compatibility.

The results are given below:

| Active ingredient kg/ha | I | | | | II | | | | IV | | | |
|---|---|---|---|---|---|---|---|---|---|---|---|---|
| | 0.25 | 0.5 | 0.75 | 1 | 0.25 | 0.5 | 0.75 | 1 | 0.25 | 0.5 | 0.75 | 1 |
| Crop plant: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 17 | 33 | 38 | 55 | 10 | 18 | 25 | 30 | 11 | 16 | 20 | 27 |
| Echinochloa crus-galli | 12 | 27 | 40 | 45 | 8 | 15 | 27 | 35 | 15 | 22 | 30 | 35 |
| Matricaria chamomilla | 10 | 23 | 30 | 34 | 10 | 16 | 25 | 32 | 6 | 10 | 14 | 15 |
| Active ingredient | VIII | | | | X | | | | XII | | | |
| Beta vulgaris | 0 | 0 | 0 | 0 | 0 | 0 | 5 | 7 | 0 | 0 | 0 | 0 |
| Avena fatua | 12 | 15 | 20 | 25 | 8 | 17 | 70 | 75 | 7 | 11 | 12 | 12 |
| Echinochloa crus-galli | 10 | 14 | 23 | 30 | 9 | 20 | 30 | 50 | 10 | 15 | 19 | 25 |
| Matricaria chamomilla | 6 | 10 | 17 | 20 | 15 | 24 | 37 | 43 | 15 | 35 | 42 | 45 |
| Active ingredient | XIII | | | | XV | | | | XVI | | | |
| Beta vulgaris | 0 | 0 | 0 | 0 | 0 | 0 | 0 | 0 | 0 | 0 | 0 | 0 |
| Avena fatua | 10 | 25 | 26 | 35 | 10 | 30 | 47 | 70 | 0 | 3 | 10 | 20 |
| Echinochloa crus-galli | 14 | 28 | 40 | 48 | 0 | 5 | 10 | 12 | 0 | 10 | 14 | 15 |
| Matricaria chamomilla | 15 | 24 | 35 | 45 | 1 | 6 | 6 | 10 | 7 | 20 | 24 | 30 |
| Active ingredient kg/ha | XVII | | | | XVIII | | | | | | | |
| | 0.25 | 0.5 | 0.75 | 1 | 0.25 | 0.5 | 1 | | | | | |
| Crop plant: | | | | | | | | | | | | |
| Beta vulgaris | 0 | 0 | 0 | 0 | 0 | 0 | 0 | | | | | |
| Unwanted plants: | | | | | | | | | | | | |
| Avena fatua | 15 | 30 | 38 | 45 | 15 | 32 | 49 | | | | | |
| Echinochloa crus-galli | 0 | 0 | 0 | 2 | 0 | 0 | 3 | | | | | |
| Matricaria chamomilla | 0 | 0 | 0 | 2 | 0 | 0 | 9 | | | | | |

0 = no damage
100 = complete destruction

| Active ingredient kg/ha | XV + VI + X | | | II + XVII + X | | | XVI + XVII + X | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Crop plant: | | | | | | | | | |
| *Beta vulgaris* | 0 | 0 | 0 | 0 | 0 | 0 | 0 | 0 | 0 |
| Unwanted plants: | | | | | | | | | |
| *Avena fatua* | 76 | 72 | 87 | 80 | 86 | 79 | 70 | 76 | 64 |
| *Echinochloa crus-galli* | 73 | 69 | 67 | 66 | 55 | 62 | 58 | 47 | 57 |
| *Matricaria chamomilla* | 69 | 64 | 65 | 72 | 63 | 69 | 68 | 60 | 73 |
| Active ingredient | XVI + XVII+XIII | | | XV + XVII + X | | | XV + XVII + XVIII | | |
| *Beta vulgaris* | 0 | 0 | 0 | 0 | 0 | 0 | 0 | 0 | 0 |
| *Avena fatua* | 78 | 77 | 66 | 80 | 86 | 91 | 95 | 93 | 97 |
| *Echinochloa crus-galli* | 66 | 52 | 62 | 58 | 47 | 52 | — | — | 43 |
| *Matricaria chamomilla* | 69 | 60 | 73 | 63 | 54 | 59 | 39 | 38 | 44 |
| Active ingredient | II + VIII + X | | | II+VIII+XVIII | | | II+VIII + XII | | |
| *Beta vulgaris* | 0 | 0 | 0 | 0 | 0 | 0 | 0 | 0 | 0 |
| *Avena fatua* | 77 | 71 | 76 | 92 | 78 | 83 | 71 | 70 | 75 |
| *Echinochloa crus-galli* | 76 | 69 | 72 | 56 | 60 | 63 | 70 | 70 | 73 |
| *Matricaria chamomilla* | 78 | 73 | 75 | 54 | 58 | 60 | 89 | 73 | 75 |
| Active ingredient | XVI + VII + X | | | XV + VIII + X | | | XVII + X + XII | | |
| *Beta vulgaris* | 0 | 0 | 0 | 0 | 0 | 0 | 0 | 0 | 0 |
| *Avena fatua* | 67 | 67 | 61 | 77 | 71 | 88 | 83 | 77 | 83 |
| *Echinochloa crus-galli* | 68 | 67 | 67 | 68 | 61 | 62 | 57 | 68 | 57 |
| *Matricaria chamomilla* | 75 | 74 | 89 | 69 | 64 | 65 | 68 | 77 | 68 |
| Active ingredient | XVI + X + XVIII | | | XVI + X + XIII | | | XVI + X + XII | | |
| Beta vulgaris | 0 | 0 | 0 | 0 | 0 | 0 | 0 | 0 | 0 |
| *AVena fatua* | 78 | 70 | 68 | 71 | 65 | 69 | 67 | 62 | 56 |
| *Echinochloa crus-galli* | 47 | 58 | 57 | 75 | 72 | 71 | 62 | 68 | 67 |
| *Matricaria chamomilla* | 60 | 69 | 73 | 84 | 84 | 88 | 95 | 84 | 88 |
| Active ingredient | XV + X + XII | | | XVIII+XIII+XII | | | VI + XIII+XII | | |
| Beta vulgaris | 0 | 0 | 0 | 0 | 0 | 0 | 0 | 0 | 0 |
| *Avena fatua* | 67 | 72 | 83 | 74 | 85 | 87 | 70 | 81 | 71 |
| *Echinochloa crus-galli* | 62 | 68 | 62 | 67 | 76 | 62 | 82 | 90 | 84 |
| *Matricaria chamomilla* | 94 | 78 | 74 | 88 | 77 | 68 | 94 | 83 | 78 |
| Active ingredient | VIII+XIII+XII | | | XVI+XVIII+XII | | | Vi+X+XVIII | | |
| Crop plant: | | | | | | | | | |
| *Beta vulgaris* | 0 | 0 | 0 | 0 | 0 | 0 | 0 | 0 | 0 |
| Unwanted plants: | | | | | | | | | |
| *Avena fatua* | 71 | 82 | 70 | 64 | 77 | 63 | 89 | 81 | 77 |
| *Echinochloa crus-galli* | 77 | 86 | 76 | 53 | 48 | 58 | 62 | 73 | 69 |
| *Matricaria chamomilla* | 94 | 82 | 78 | 80 | 60 | 73 | 59 | 68 | 63 |
| Active ingredient | XVII+X+XIII | | | VI+XVIII+XIII | | | VI+XVIII+XII | | |
| *Beta vulgaris* | 0 | 0 | 0 | 0 | 0 | 0 | 0 | 0 | 0 |
| *Avena fatua* | 86 | 85 | 86 | 89 | 91 | 79 | 75 | 88 | 76 |
| *Echinochloa crus-galli* | 75 | 72 | 61 | 81 | 67 | 74 | 68 | 63 | 70 |
| *Matricaria chamomilla* | 77 | 76 | 68 | 67 | 59 | 63 | 79 | 59 | 63 |
| Active ingredient | XVII+XVIII+XIII | | | XVII+XVIII+XII | | | XVII+XIII+XII | | |
| Beta vulgaris | 0 | 0 | 0 | 0 | 0 | 0 | 1 0 | 0 | 0 |
| *AVena fatua* | 93 | 95 | 92 | 79 | 91 | 90 | 74 | 85 | 85 |
| *Echinochloa crus-galli* | 65 | 52 | 51 | 53 | 48 | 47 | 67 | 76 | 62 |
| *Matricaria chamomilla* | 62 | 53 | 52 | 72 | 53 | 52 | 88 | 77 | 68 |
| Active ingredient | X+XIII+XII | | | II+XVIII+XIII | | | II+XVIII+XII | | |
| Crop plant: | | | | | | | | | |
| *Beta vulgaris* | 0 | 0 | 0 | 0 | 0 | 0 | 0 | 0 | 0 |
| Unwanted plants: | | | | | | | | | |
| *Avena fatua* | 67 | 78 | 72 | 88 | 90 | 81 | 74 | 87 | 78 |
| *Echinochloa crus-galli* | 75 | 85 | 82 | 74 | 60 | 67 | 61 | 56 | 63 |
| *Matricaria chamomilla* | 100 | 92 | 92 | 72 | 63 | 69 | 83 | 63 | 68 |
| Active ingredient | XV+XVIII+XIII | | | XV+XVIII+XII | | | XVI+XVIII+XIII | | |
| *Beta vulgaris* | 0 | 0 | 0 | 0 | 0 | 0 | 0 | 0 | 0 |
| *Avena fatua* | 74 | 90 | 93 | 74 | 87 | 90 | 78 | 80 | 66 |
| *Echinochloa crus-galli* | 53 | 52 | 57 | 53 | 48 | 53 | 66 | 52 | 62 |
| *Matricaria chamomilla* | 74 | 54 | 59 | 74 | 54 | 59 | 69 | 60 | 73 |
| Active ingredient | I + X + XIII | | | I + X + XII | | | II + X + XVIII | | |
| Beta vulgaris | 0 | 0 | 0 | 0 | 0 | 0 | 0 | 0 | 0 |
| *Avena fatua* | 88 | 83 | 88 | 74 | 79 | 86 | 88 | 80 | 79 |
| *Echinochloa crus-galli* | 86 | 84 | 87 | 73 | 80 | 84 | 55 | 66 | 62 |
| *Matricaria chamomilla* | 87 | 86 | 91 | 98 | 87 | 91 | 63 | 72 | 68 |
| Active ingredient | II + X + XIII | | | II + X + XII | | | XV + X + XVIII | | |
| Crop plant: | | | | | | | | | |
| *Beta vulgaris* | 0 | 0 | 0 | 0 | 0 | 0 | 0 | 0 | 0 |
| Unwanted plants: | | | | | | | | | |
| *Avena fatua* | 81 | 75 | 74 | 67 | 72 | 71 | 88 | 80 | 91 |
| *Echinochloa crus-galli* | 83 | 80 | 76 | 70 | 76 | 72 | 47 | 58 | 52 |
| *Matricaria chamomilla* | 87 | 86 | 84 | 98 | 87 | 84 | 54 | 63 | 59 |
| Active ingredient | XV + X + XIII | | | I + II + XIII | | | I + XVI + XII | | |
| Beta vulgaris | 0 | 0 | 0 | 0 | 0 | 0 | 0 | 0 | 0 |
| *Avena fatua* | 81 | 75 | 86 | 90 | 83 | 91 | 65 | 66 | 78 |
| *Echinochloa crus-galli* | 75 | 72 | 61 | 90 | 79 | 87 | 64 | 70 | 74 |
| *Matricaria chamomilla* | 78 | 77 | 69 | 80 | 80 | 85 | 90 | 82 | 83 |

-continued

| Active ingredient kg/ha | XV + VI + X | | | II + XVII + X | | | XVI + XVII + X | | |
|---|---|---|---|---|---|---|---|---|---|
| | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 | 0.25+ 0.25+ 0.5 | 0.25+ 0.5+ 0.25 | 0.5+ 0.25+ 0.25 |
| Active ingredient | I + XV + X | | | I + XV + XVI | | | I + XV + II | | |
| Beta vulgaris | 0 | 0 | 0 | 0 | 0 | 0 | 0 | 0 | 0 |
| Avena fatua | 82 | 92 | 89 | 68 | 85 | 81 | 83 | 95 | 91 |
| Echinochloa crus-galli | 70 | 65 | 74 | 60 | 55 | 65 | 65 | 63 | 72 |
| Matricaria chamomilla | 73 | 69 | 77 | 68 | 61 | 69 | 64 | 64 | 71 |
| Active ingredient | I + XVI + II | | | I + XVII + X | | | | | |
| Crop plant: | | | | | | | | | |
| Beta vulgaris | 0 | 0 | 0 | 0 | 0 | 0 | | | |
| Unwanted plants: | | | | | | | | | |
| Avena fatua | 73 | 68 | 81 | 87 | 82 | 94 | | | |
| Echinochloa crus-galli | 65 | 67 | 72 | 60 | 58 | 74 | | | |
| Matricaria chamomilla | 70 | 78 | 77 | 72 | 63 | 76 | | | |
| Active ingredient | I + II | | | I + XV | | | I + VI | | |
| kg/ha | 0.25+ 0.75 | 0.75+ 0.25 | 0.5+ 0.5 | 0.25+ 0.75 | 0.75+ 0.25 | 0.5+ 0.5 | 0.25+ 0.75 | 0.75+ 0.25 | 0.5+ 0.5 |
| Beta vulgaris | 0 | 0 | 0 | 0 | 0 | 0 | 0 | 0 | 0 |
| Avena fatua | 80 | 86 | 89 | 100 | 86 | 100 | 75 | 87 | 87 |
| Echinochloa crus-galli | 77 | 85 | 80 | 60 | 78 | 70 | 70 | 93 | 87 |
| Matricaria chamomilla | 73 | 78 | 77 | 54 | 69 | 67 | 62 | 74 | 71 |
| Active ingredient | I + VIII | | | I + XVII | | | XVI + X | | |
| Beta vulgaris | 0 | 0 | 0 | 0 | 0 | 0 | 0 | 0 | 0 |
| Avena fatua | 75 | 88 | 86 | 93 | 91 | 100 | 100 | 66 | 68 |
| Echinochloa crus-galli | 73 | 88 | 89 | 50 | 78 | 65 | 68 | 61 | 68 |
| Matricaria chamomilla | 65 | 74 | 71 | 48 | 68 | 61 | 82 | 77 | 82 |
| Active ingredient | XV + VIII | | | XV +0 X | | | VIII + X | | |
| Crop plant: | | | | | | | | | |
| Beta vulgaris | 0 | 0 | 0 | 5 | 0 | 0 | 5 | 0 | 0 |
| Unwanted plants: | | | | | | | | | |
| Avena fatua | 68 | 97 | 83 | 100 | 93 | 85 | 100 | 66 | 80 |
| Echinochloa crus-galli | 61 | 58 | 57 | 68 | 57 | 63 | 78 | 69 | 72 |
| Matricaria chamomilla | 56 | 50 | 54 | 76 | 58 | 68 | 81 | 70 | 72 |
| Active ingredient | XVII + X | | | X +0 XIII | | | X + XII | | |
| Beta vulgaris | 5 | 0 | 0 | 0 | 5 | 0 | 0 | 5 | 0 |
| Avena fatua | 100 | 84 | 85 | 72 | 100 | 80 | 68 | 100 | 68 |
| Echinochloa crus-galli | 68 | 47 | 58 | 87 | 82 | 86 | 66 | 78 | 73 |
| Matricaria chamomilla | 75 | 53 | 62 | 88 | 90 | 86 | 95 | 80 | 97 |

0 = no damage
100 = complete destruction

EXAMPLE 34

In the greenhouse, loamy sandy soil was filled into pots and sown with the seeds of various plants. The soil prepared in this manner was subsequently treated with the following amounts of the following individual active ingredients and compositions thereof as granules:

I. 2-ethoxy-2,3-dihydro-3,3-dimethyl-5-benzofuranyl methane sulfonate, 0.25, 0.5, 1, 1.5 and 2 kg/ha;

II. isopropyl N-phenylcarbamate, 0.25, 0.5, 1, 1.5 and 2 kg/ha;

VI. α,α-dichloropropionic acid, sodium salt, 0.25, 0.5, 1, 1.5 and 2 kg/ha;

VII. trichloroacetic acid, sodium salt, 0.25, 0.5, 1, 1.5 and 2 kg/ha;

VIII. α,α,β,β-tetrafluoropropionic acid, sodium salt, 0.25, 0.5, 1, 1.5 and 2 kg/ha;

IX. 1,1,1-trifluoro-4'-(phenylsulfonyl)-methanesulfone-o-toluidide, 0.25, 0.5, 1, 1.5 and 2 kg/ha;

X. 3,4,5-tribromo-N,N-α-trimethylpyrazole-1-acetamide, 0.25, 0.5, 1, 1.5 and 2 kg/ha;

XII. 1-phenyl-4-amino-5-chloropyridazone-(6), 0.25, 0.5, 1, 1.5 and 2 kg/ha;

XIII. 3-cyclohexyl-5,6-trimethylene uracil, 0.25, 0.5, 1, 1.5 and 2 kg/ha;

I+X+XIII, I+X+XII, II+IX+X, II+X+XIII, II+X+XII, VI+IX+XIII, VI+XIIII+XII, VIII+XIII+XII, IX+X+XIII, IX+X+XII, II+IX+XII, II+IX+XIII, II+VIII+IX, II+VIII+X, each of these compositions at a rate of 0.25+0.25+1.5, 0.25+1.5+0.25 and 1.5+0.25+0.25 kg/ha;

I+II, I+VI, I+VII, I+VIII and II+XII, each of these compositions at a rate of 0.5+1.5, 1.5+0.5 and 1+1 kg/ha.

After 3 to 4 weeks it was ascertained that the compositions had a better herbicidal action than their components, combined with the same good crop plant compatibility.

The results are given below:

| Active ingredient kg/ha | I | | | | | II | | | | | VI | | | | |
|---|---|---|---|---|---|---|---|---|---|---|---|---|---|---|---|
| | 0.25 | 0.5 | 1 | 1.5 | 2 | 0.25 | 0.5 | 1 | 1.5 | 2 | 0.25 | 0.5 | 1 | 1.5 | 2 |
| Crop plant: | | | | | | | | | | | | | | | |
| Beta vulgaris | 0 | 0 | 0 | 0 | 0 | 0 | 0 | 0 | 0 | 0 | 0 | 0 | 0 | 0 | 0 |
| Unwanted plants: | | | | | | | | | | | | | | | |
| Avena fatua | 10 | 16 | 40 | 60 | 80 | 7 | 12 | 30 | 42 | 53 | 10 | 15 | 27 | 60 | 76 |
| Echinochloa crus-galli | 15 | 30 | 58 | 70 | 85 | 10 | 11 | 18 | 30 | 40 | 10 | 10 | 23 | 35 | 44 |
| Matricaria chamomilla | 5 | 9 | 22 | 30 | 40 | 7 | 18 | 40 | 63 | 78 | 0 | 0 | 0 | 3 | 5 |

-continued

| Active ingredient kg/ha | 0.25 | I 0.5 | 1 | 1.5 | 2 | 0.25 | II 0.5 | 1 | 1.5 | 2 | 0.25 | VI 0.5 | 1 | 1.5 | 2 |
|---|---|---|---|---|---|---|---|---|---|---|---|---|---|---|---|

| Active ingredient kg/ha | 0.5 | VII 1 | 1.5 | 2 | 0.25 | VIII 0.5 | 1 | 1.5 | 2 | 0.25 | IX 1.5 | 2 |
|---|---|---|---|---|---|---|---|---|---|---|---|---|
| Beta vulgaris | 0 | 0 | 0 | 0 | 0 | 0 | 0 | 0 | 0 | 0 | 5 | 10 |
| Avena fatua | 10 | 24 | 45 | 56 | 8 | 18 | 35 | 50 | 67 | 0 | 80 | 95 |
| Echinochloa crus-galli | 10 | 17 | 30 | 40 | 5 | 15 | 30 | 48 | 61 | 17 | 78 | 100 |
| Matricaria chamomilla | 0 | 0 | 2 | 7 | 0 | 0 | 5 | 10 | 17 | 10 | 25 | 35 |

| Active ingredient kg/ha | 0.25 | X 1.5 | 2 | 0.25 | XII 0.5 | 1 | 1.5 | 2 | 0.25 | XIII 1.5 | 2 |
|---|---|---|---|---|---|---|---|---|---|---|---|
| Beta vulgaris | 0 | 5 | 7 | 0 | 0 | 0 | 0 | 0 | 0 | 0 | 20 |
| Avena fatua | 20 | 80 | 95 | 3 | 5 | 12 | 15 | 20 | 5 | 20 | 30 |
| Echinochloa crus-galli | 15 | 75 | 95 | 5 | 8 | 13 | 20 | 32 | 16 | 70 | 90 |
| Matricaria chamomilla | 5 | 20 | 31 | 15 | 30 | 50 | 60 | 85 | 20 | 75 | 95 |

| Active ingredient kg/ha | II + XII 0.5+1.5 | 1.5+0.5 | 1+1 | I + II 0.5+1.5 | 1.5+0.5 | 1+1 | I + VI 0.5+1.5 | 1.5+0.5 | 1+1 |
|---|---|---|---|---|---|---|---|---|---|
| Crop plant: | | | | | | | | | |
| Beta vulgaris | 0 | 0 | 0 | 25 | 5 | 4 | 25 | 5 | 4 |
| Unwanted plants: | | | | | | | | | |
| Avena fatua | 67 | 87 | 82 | 98 | 100 | 100 | 100 | 100 | 100 |
| Echinochloa crus-galli | 71 | 78 | 71 | 100 | 100 | 100 | 100 | 100 | 100 |
| Matricaria chamomilla | 100 | 100 | 100 | 100 | 100 | 100 | 52 | 70 | 62 |

| Active ingredient | I + VII | | | I + VIII | | |
|---|---|---|---|---|---|---|
| Beta vulgaris | 25 | 5 | 4 | 25 | 5 | 4 |
| Avena fatua | 100 | 100 | 100 | 100 | 100 | 100 |
| Echinochloa crus-galli | 100 | 100 | 100 | 100 | 100 | 100 |
| Matricaria chamomilla | 51 | 70 | 62 | 59 | 70 | 67 |

| Active ingredient kg/ha | II + VIII + X 0.25+0.25+1.5 | 0.25+1.5+0.25 | 1.5+0.25+0.25 | II + VIII + IX 0.25+0.25+1.5 | 0.25+1.5+0.25 | 1.5+0.25+0.25 | I + X + XIII 0.25+0.25+1.5 | 0.25+1.5+0.25 | 1.5+0.25+0.25 |
|---|---|---|---|---|---|---|---|---|---|
| Crop plant: | | | | | | | | | |
| Beta vulgaris | 5 | 0 | 0 | 5 | 0 | 0 | 0 | 5 | 5 |
| Unwanted plants: | | | | | | | | | |
| Avena fatua | 100 | 100 | 100 | 100 | 97 | 95 | 95 | 100 | 100 |
| Echinochloa crus-galli | 100 | 100 | 97 | 100 | 100 | 98 | 100 | 100 | 100 |
| Matricaria chamomilla | 71 | 70 | 100 | 77 | 72 | 100 | 100 | 100 | 100 |

| Active ingredient | I + X + XII | | | II + X + IX | | | II + X + XIII | | |
|---|---|---|---|---|---|---|---|---|---|
| Beta vulgaris | 0 | 5 | 5 | 5 | 5 | 0 | 0 | 5 | 0 |
| Avena fatua | 87 | 100 | 100 | 100 | 100 | 100 | 92 | 100 | 100 |
| Echinochloa crus-galli | 95 | 100 | 100 | 100 | 100 | 100 | 100 | 100 | 100 |
| Matricaria chamomilla | 100 | 85 | 90 | 77 | 77 | 100 | 100 | 93 | 100 |

| Active ingredient | II + X + XII | | | VI + IX + XIII | | | VI + XIII + XII | | |
|---|---|---|---|---|---|---|---|---|---|
| Beta vulgaris | 0 | 5 | 0 | 0 | 5 | 0 | 0 | 0 | 0 |
| Avena fatua | 82 | 100 | 100 | 70 | 100 | 100 | 70 | 77 | 100 |
| Echinochloa crus-galli | 85 | 100 | 100 | 100 | 100 | 100 | 90 | 100 | 96 |
| Matricaria chamomilla | 100 | 87 | 100 | 100 | 90 | 73 | 100 | 100 | 86 |

| Active ingredient | VIII + XIII + XII | | | X + IX + XIII | | | X + IX + XII | | |
|---|---|---|---|---|---|---|---|---|---|
| Crop plant: | | | | | | | | | |
| Beta vulgaris | 0 | 0 | 0 | 0 | 5 | 5 | 0 | 5 | 5 |
| Unwanted plants: | | | | | | | | | |
| Avena fatua | 68 | 71 | 98 | 86 | 100 | 100 | 80 | 100 | 100 |
| Echinochloa crus-galli | 87 | 100 | 100 | 100 | 100 | 100 | 97 | 100 | 100 |
| Matricaria chamomilla | 100 | 100 | 95 | 100 | 100 | 96 | 100 | 87 | 85 |

| Active ingredient | II + IX + XII | | | II + IX + XIII | | |
|---|---|---|---|---|---|---|
| Beta vulgaris | 0 | 5 | 0 | 0 | 5 | 0 |
| Avena fatua | 68 | 100 | 85 | 70 | 100 | 97 |
| Echinochloa crus-galli | 93 | 100 | 100 | 100 | 100 | 100 |
| Matricaria chamomilla | 100 | 87 | 100 | 100 | 95 | 100 |

0 = no damage
100 = complete destruction

EXAMPLE 35

In the greenhouse, various plants were treated at a growth height of from 3 to 8 cm with the following amounts of the following individual active ingredients and compositions thereof as dispersions or emulsions:

I. 1-phenyl-4-amino-5-chloropyridazone-(6), 1, 1.5, 2 and 3 kg/ha;

II. benzamidooxyacetic acid, 1, 1.5, 2, and 3 kg/ha.

After 18 to 25 days it was ascertained that the composition had a better herbicidal action than its compounds, combined with the same good crop plant compatibility.

The results are given below:

| Active ingredient kg/ha | I |  |  |  | II |  |  |  |
|---|---|---|---|---|---|---|---|---|
|  | 1 | 1.5 | 2 | 3 | 1 | 1.5 | 2 | 3 |
| Crop plant: | | | | | | | | |
| Beta vulgaris | 0 | 0 | 0 | 0 | 0 | 0 | 0 | 10 |
| Unwanted plants: | | | | | | | | |
| Kochia scoparia | 20 | 25 | 40 | 80 | 40 | 65 | 80 | 90 |
| Chenopodium album | 45 | 50 | 65 | 90 | 30 | 40 | 53 | 70 |
| Poa annua | 35 | 45 | 70 | 90 | 15 | 25 | 30 | 40 |
| Active ingredient kg/ha | I + II |  |  |  |  |  |  |  |
|  | 2 + 1 |  | 1 + 2 |  | 1.5 + 1.5 |  | 1 + 1 |  |
| Crop plant: | | | | | | | | |
| Beta vulgaris | 0 |  | 0 |  | 0 |  | 0 |  |
| Unwanted plants: | | | | | | | | |
| Kochia scoparia | 100 |  | 100 |  | 100 |  | 96 |  |
| Chenopodium album | 100 |  | 100 |  | 100 |  | 100 |  |
| Poa annua | 100 |  | 100 |  | 100 |  | 95 |  |

0 = no damage
100 = complete destruction

The action of compositions of I with salts or esters of benzamidooxyacetic acid corresponds to that of I + II.

I claim:

1. A herbicide composition consisting essentially of an inert carrier and a herbicidally effective amount of a mixture of (a) 2-ethoxy-2,3-dihydro-3,3-dimethyl-5-benzofuranyl methane sulfonate and (b) 1-m-trifluoromethylphenyl-4-dimethylamino-5-chloropyridazone-(6) in a weight ratio of (a) to (b) in the range of 3:1 to 1:3.

* * * * *